US005962669A

United States Patent [19]
Prusiner et al.

[11] Patent Number: 5,962,669
[45] Date of Patent: Oct. 5, 1999

[54] NUCLEIC ACID ENCODING PRION PROTEIN VARIANT

[75] Inventors: Stanley B. Prusiner; Fred E. Cohen, both of San Francisco; Thomas L. James, Nicasio; Kiyotoshi Kaneko, San Francisco, all of Calif.

[73] Assignee: The Regents of the University of California, Oakland, Calif.

[21] Appl. No.: 08/868,162

[22] Filed: Jun. 2, 1997

[51] Int. Cl.[6] .................................................... C12N 15/11

[52] U.S. Cl. .................... 536/23.5; 536/23.1; 536/23.72; 435/69.1; 435/252.3; 435/320.1
[58] Field of Search ................................ 536/23.5, 23.1, 536/23.72; 435/69.1, 252.3, 320.1

[56] References Cited

U.S. PATENT DOCUMENTS

| | | | |
|---|---|---|---|
| 5,025,388 | 6/1991 | Cramer, III et al. | 364/496 |
| 5,307,287 | 4/1994 | Cramer, III et al. | 364/496 |
| 5,434,796 | 7/1995 | Weininger | 364/496 |
| 5,526,281 | 6/1996 | Chapman et al. | 364/496 |
| 5,565,186 | 10/1996 | Prusiner et al. | 424/9.2 |
| 5,750,361 | 5/1998 | Prusiner et al. | 435/23 |
| 5,763,740 | 6/1998 | Prusiner et al. | 800/2 |
| 5,789,655 | 8/1998 | Prusiner et al. | 800/2 |
| 5,792,901 | 8/1998 | Prusiner et al. | 800/2 |

FOREIGN PATENT DOCUMENTS

| | | |
|---|---|---|
| WO 91/19810 | 12/1991 | WIPO . |
| WO 93/10227 | 5/1995 | WIPO . |

OTHER PUBLICATIONS

Yokoyama et al. (1996) Archives of Virology 141 (3–4):763–769 (abstract), 1996.
Groschup et al. (1993) Journal of General Virology 74/7:1451–1456 (abstract), 1993.

Baker, H.F., et al. "Aminoacid Polymorphism in Human Prion Protein and Age at Death in Inherited Prion Disease," *Lancet* (1991) 337:1286.

Barry, R.A., et al., "Monoclonal Antibodies to the Cellular and Scrapie Prion Proteins," *J. Infect. Dis.* (1986) 154(3):518–521.

Basler et al., "Scrapie and Cellular PrP Isoforms Are Encoded by the Same Chromosomal Gene," *Cell*, (1986) 46:417–28.

Berger, J.R., et al., "Creutzfeldt–Jakob disease in a physician: A review of the disorder in health care workers", *Neurology*, (1993) 43:205–206.

Bolton et al., "Identification of a Protein That Purifies with the Scrapie Prion," *Science* (1982) 218: 1309–11.

Brown et al., "Friendly Fire' in Medicine: Hormones, Homografts, and Cruetzfeldt–Jakob Disease, " *Lancet* (1992) 340:24–27.

Buchanan et al., "Mortality, Neoplasia, and Creutzfeld–Jakob Disease in Patients Treated with Human Pituitary Growth Hormone in the United Kingdom", *BMJ* (1991) 302:824–828.

Bueler et al., "Mice Devoid of PrP are Resistant to Scrapie," *Cell* (1993) 73:1339–1347.

Bueler et al., "Normal Development and behavior of Mice Lacking the Neuronal Cell–surface PrP Protein," *Nature* (1992) 356:577–582.

Carlson et al., "Linkage of Protein and Scrapie Incubation Time Genes," *Cell* (1986) 46:503–511.

Chandler, "Encephaolpathy in Mice Produced by Inoculation with Scrapie Brain Material," Lancet (1961) 1:1378–79.

Cochius et al, "Creutzfeldt–Jakob Disease in a Recipient of Human Pituitary–Derived Gonadotrophin: A Second Case," *J. Neurol. Neurosurg. Psychiatry* (1992) 55:1094–1095.

Cochius et al., "Creutzfeldt–Jakob Disease in a Recipient of Human Pituitary–Derived Gonadotrophin," *Aust. N.Z. J. Med.* (1990) 20:592–593.

Collinge et al., "Genetic Predisposition to Latrogenic Creutzfeldt–Jakob Disease," *Lancet* (1991) 337:1441–1442.

Cousens, S.N., et al., "Geographical distribution of cases of Creutzfeldt–Jakob disease in England and Wales 1970–84", *J. Neurol. Neurosurg. Psychiatry* (1990) 53:459–465.

Farlie, P.G., et al., "bcl–2 Transgene expression can protect neurons against developmental and induced cell death", *Proc. Natl. Acad. Sci. USA* (1995) 92:4397–4401.

Gabriel et al., "Molecular Cloning of a Candidate Chicken Prion Protein," *Proc. Natl. Acad. Sci. USA* (1992) 89:9097–9101.

Gajdusek, D.C., "Unconventional Viruses and the Origin and Disappearance of Kuru," *Science* (1977) 197:943–960.

Gibbs, Jr. et al., "Creutzfeldt–Jakob Disease Infectivity of Growth Hormone Derived from Human Pituitary Glands," *N.Engl. J. Med.* (1993) 328:358–359.

Goldfarb et al, "Fatal Familial Insomnia and Familial Creutzfeldt–Jakob Disease: Disease Phenotype Determined by a DNA Polymorphism," *Science* (1992) 258:806–808.

(List continued on next page.)

*Primary Examiner*—Robert A. Wax
*Assistant Examiner*—Enrique D. Longton
*Attorney, Agent, or Firm*—Karl Bozicevic; Bozicevic, Field & Francis LLP

[57] ABSTRACT

A protein designated Prion Protein Modulator Factor (PPMF) is disclosed which protein is an auxiliary factor in prion replication. PPMF is primarily characterized by its ability to bind to $PrP^{C}$ and facilitate a conformational change from $PrP^{C}$ to $PrP^{Sc}$. A discontinuous epitope on $PrP^{C}$ comprising residues 172, 215 and 219 of human $PrP^{C}$ binds PPMF which is encoded by a nucleotide sequence derived from an organism selected from the group consisting of cow, sheep, mouse, hamster and human. In converting $PrP^{C}$ to $PrP^{Sc}$ the PPMF forms a $PrP^{C}/PrP^{Sc}$ complex and is a rate limiting compound in the formation of that complex. Molecules, including antibodies, which bind PPMF or its epitope on $PrP^{C}$ are useful in the treatment of prion disease. Pharmacophores of the $PrP^{C}$ epitope are disclosed as are useful therapeutics and pharmacophores of the PPMF surface which binds $PrP^{C}$. Animals resistant to prion disease are taught as are genes for producing such animals. Assay systems are disclosed which use PPMF to amplify $PrP^{Sc}$ is a sample being tested.

7 Claims, 15 Drawing Sheets

OTHER PUBLICATIONS

Goldmann et al., "Two Alleles of a Neural Protein Gene Linked to Scrapie in Sheep," *Proc. Natl. Acad. Sci. USA* (1990) 87:2476–2480.

Goldmann et al., "Different Forms of the Bovine PrP Gene Have Five or Six Copies of a Short, G–C Rich Element within the protein–coding Exon," *J. Gen. Virol.* (1991) 72:201–204.

Harris et al., "A Prion–like Protein from Chicken Brain Copurifies with an Acetylcholine Receptor–Inducing Activity," *Proc. Natl. Acad. Sci. USA* (1991) 88:7664–7668.

Hasty, P., et al., "Introduction of a subtle mutation into the Hox–2.6 locus in embryonic stem cells", *Nature* (1991) 350:243–246.

Healy et al., "Creutzfeldt–Jakob Disease After Pituitary Gonadotrophins: The Prion is the Problem," *BMJ* (1993) 307:517–518.

Hecker et al., "Replication of Distinct Scrapie Prion Isolates is Region Specific in Brains of Transgenic Mice and Hamsters," *Genes Dev.* (1992) 6:1213–1228.

Hsaio et al.,"Linkage of a Prion Protein Missense Variant to Gerstmann–Straussler Syndrome," *Nature* (1989) 383:342–345.

Hsaio et al., "A Prion Protein Variant in a Family with the Telencephalic Form of Gerstmann–Strussler–Scheinker Syndrome," *Neurology* (1991) 41:681–684.

Hsaio et al., "Inherited Human Prion Disease," *Neurology* (1990) 40:1820–1827.

Kascasak, R.J., et al., "Mouse Polyclonal and Monoclonal Antibody to Scrapie–Associated Fibril Proteins," *J. Virol.* (1987) 61(12):3688–3693.

Koch et al.,"Creutzfeldt–Jakob Disease in a Young Adult with Idiopathic Hypopituitarism," *N. Engl. J. Med.* (1985) 313:731–733.

Kretzschmar et al., "Molecular Cloning of a Human Prion Protein cDNA," *DNA* (1986) 5:315–324.

Kretzschmar et al., "Molecular Cloning of a Mink Prion Protein Gene," *J.Gen.Virol.* (1992) 73:2757–2761.

Lasmezas et al.,"Recombinant Human Hormone and Insulin–Like Growth Factor I Induce PRP Gene Expression in PC12 Cell," *Biochem. Biophys. Res.Commun.* (1993) 196:1163–1169.

Locht et al.,"Molecular Cloning and Complete Sequence of Prion Protein cDNA from Mouse Brain Infected with the Scrapie Agent," *Proc. Natl. Acad. Sci. USA* (1986) 83:6372–6376.

Manuelidis et al., "Serial Propagation of Creutzfeldt–Jakob Disease in Guinea Pigs," *Proc. Natl. Acad. Sci. USA* (1976) 73:223–227.

Manuelidis et al., "Interspecies Transmission of Creutzfeldt–Jakob Disease to Syrian Hamsters with Reference to Clinical Syndromes and Strain of Agent," *Proc. Natl. Acad. Sci. USA* (1978) 75:3432–3436.

McKinley et al, "A Protease–Resistant Protein is a Structural Component of the Scrapie Prion," *Cell* (1983) 35:57–62.

Medori et al., "Fatal Familial Insomnia, a Prion Disease with a Mutation at Codon 178 of the Prion Protein Gene," *N. Engl.J. Med.* (1992) 326:444–449.

Muramoto, T., et al., "The Sequential Development of Abnormal Prion Protein Accumulation in Mice with Creuzfeldt–Jakob Disease," *Am. J. Pathol.* (1992) 140(6):1411–1420.

Nisbet et al., "Creutzfeldt–Jakob Disease in a Second Patient Who Received a Cadaveric Dura mater Graft," *J.Am. Med.Assoc.* (1989) 261:1118.

Palmer, M.S., et al., "Homozygous Prion Protein Genotype Predisposes to Sporadic Creutzfeldt–Jakob Disease", *Nature* (1991) 352:340–342.

Patel, "France Reels at Latest Medical Scandal," *New Scientist*, Jul. 31, 1993, p.4.

Patel, "Placenta Donors to be Screened for Brain Disease,"0 *New Scientist*, Nov. 20, 1993, p. 10.

Pan, K.M., et al., "Conversion of β–sheets features in the formation of the scrapie prion proteins", *Proc. Natl. Acad. Sci. USA* (1993) 90:10962–10966.

Prusiner et al., "Measurement of the Scrapie Agent Using an Incubation Time Interval Assay," *Annals. Neurol.* (1982) 11(4):353–358.

Prusiner et al., "Further Purification and Characterization of Scrapie Prions," *Biochemistry* (1982) 21:6942–50.

Prusiner, S.B., et al., "Scrapie Prions Aggregate to Form Amyloid–like Birefringent Rods," *Cell* (1983) 35:349–358.

Prusiner et al., "Transgenic Studies Implicate Interactions Between Homologous PrP Isoforms in Scrapie Prion Replication," *Cell* (1990) 63:673–686.

Prusiner et al., "Molecular Biology of Prion Diseases," *Science* (1991) 252:1515–1522.

Prusiner et al., "Ablation of the Prion Protein (PrP) Gene in Mice Prevents Scrapie and Facilitates Production of Anti–PrP Antibodies," *Proc. Natl. Acad. Sci. USA* (1993) 90:10608–10612.

Prusiner, S.B., et al., "Immunologic and Molecular Biological Studies of Prion Proteins in Bovine Spongiform Encephalopathy," *J. Infect. Dis.* (1993) 167:602–613.

Prusiner et al., "Prion Diseases and Neurodegeneration," *Ann.Rev.Neurosci.* (1994) 17:311–339.

Raeber et al., "Attempts to Convert the Cellular Prion Protein into the Scrapie Isoform in Cell–Free Systems," *J. Virol.* (1992) 66:6155–6163.

Ridley et al., *Lancet* Occupational Risk of Creufeldt–Jakob Disease, (1993) 341:641–2.

Rogers, M. et al., "Epitope Mapping of the Syrian Hamster Prion Protein Utilizing Chimeric and Mutant Genes in a Vaccinia Virus Expression System," *J. immunol.* (1991) 147(10):3568–3574.

Scott, M., et al, "Transgenic Mice Expressing Hamster Prion Protein Produce Species–Specific Infectivity and Amyloid Plaques," *Cell* (1989) 59:847–857.

Scott et al, "Chimeric Prion Protein Expression in Cultured Cells and Transgenic Mice," *Protein Sci.* (1992) 1:986–97.

Scott et al, "Propagation of Prions with Artificial Properties in Transgenic Mice Expressing Chimeric PrP Genes," *Cell* (1993) 73:979–988.

Serban, D., et al. "Rapid detection of Creutzfeldt–Jakob disease and scrapie prion proteins", *Neurology* (1990) 40:110–117.

Stahl et al., "Glycosylinositol Phospholipid Anchors of the Scrapie and Cellular Prion Proteins Contain Sialic Acid," *Biochemistry* (1992) 31:5043–5053.

Taraboulos et al., "Regional Mapping of Prion Proteins in Brain," *Proc. Natl. Acad. Sci. USA* (1992) 89:7620–7624.

Tateishi, J. and Kitamoto, T., "Developments in Diagnosis for Prion Diseases," *Br. Med. Bull.* (1993) 49(4):971–979.

Tateishi et al.,"Transmission of Chronic Spongiform Encephalopathy with Kuru Plaques from Humans to Small Rodents," *Ann.Neurol.* (1979) 5:581–584.

Thadani et al., "Creutzfeldt–Jakob Disease Probably Acquired From a Cadaveric Dura Mater Graft," *J. Neurosurg.* (1988) 69:766–769.

Valancius, V. and Smithies, O., "Testing and "In–Out" Targeting Procedure for Making Subtle Genomic Modifications in Mouse Embryonic Stem Cells", *Mol. Cell Biol.* (1991) 11(3):1402–1408.

Westaway et al., Homozygosity for Prion Protein Alleles Encoding Glutamine–171 Renders Sheep Susceptible to Natural Scrapie,: *Genes Dev.* (1994) 8:959–969.

Westaway et al., "Degeneration of Skeletal Muscle, Peripheral Nerves, and the Central Nervous System in Transgenic Mice Overexpressing Wild–Type Prion Proteins," *Cell* 76:117–129.

Willison et al., "Creutzfeldt–Jakob Disease Following Cadaveric Dura Mater Graft," *Neurosurg. Psychiatric* (1991) 54:940.

Wilesmith, J.W., "The epidemiology of bovine spongiform encephalopathy", *Acad. Press.* (1991) 2:239–245.

Kaneko, K. et al., "Evidence for protein X binding to a discontinuous epitope on the cellular prion protein during scrapie protein propagation," *Proc Natl Acad USA* (Sep. 1977) 94:10069–10074.

Telling, G.C. et al., "Prion Propagation in Mice Expressing Human and Chimeric PrP Transgenes Implicates the Interaction of Cellular PrP with Another Protein," *Cell* (Oct. 6, 1995) 83:79–90.

Prusiner, S.B., et al., "Prion Protein Biology," *Cell* (May 1, 1998) 93:337–348.

Telling, G.C., et al., "Transmission of Creutzfeldt–Jakob disease from humans to transgenic mice expressing chimeric human–mouse prion protein," *Proc Natl Acad Sci USA* (Oct. 1994) 91:9936–9940.

Cohen, F.E., et al., "Structural Clues to Prion Replication," *Science* (Apr. 22, 1994) 264:530–531.

Yehiely, F., et al., "Identification of candidate proteins binding to prion proteins," *Neurobiology of Disease* 3(4):339–355 (1997) (Abstract).

| | | | | | | | | | | | | | | | | |
|---|---|---|---|---|---|---|---|---|---|---|---|---|---|---|---|---|
| Mo | Met | Ala | Asn | Leu | Gly | Tyr | Trp | Leu | Leu | Ala | Leu | Phe | Val | Thr | Met | Trp | 16 |
| Hu | | | | | | | Cys | | Met | | Val | | | | Ala | Thr | |

| | | | | | | | | | | | | | | | | |
|---|---|---|---|---|---|---|---|---|---|---|---|---|---|---|---|---|
| Mo | Thr | Asp | Val | Gly | Leu | Cys | Lys | Lys | Arg | Pro | Lys | Pro | Gly | Gly | Trp | Asn | 32 |
| Hu | Ser | | Leu | | | | | | | | | | | | | | |

| | | | | | | | | | | | | | | | | |
|---|---|---|---|---|---|---|---|---|---|---|---|---|---|---|---|---|
| Mo | Thr | Gly | Gly | Ser | Arg | Tyr | Pro | Gly | Gln | Gly | Ser | Pro | Gly | Gly | Asn | Arg | 48 |
| Hu | | | | | | | | | | | | | | | | | |

| | | | | | | | | | | | | | | | | |
|---|---|---|---|---|---|---|---|---|---|---|---|---|---|---|---|---|
| Mo | Tyr | Pro | Pro | Gln | Gly | Gly | --- | Thr | Trp | Gly | Gln | Pro | His | Gly | Gly | Gly | 63 |
| Hu | | | | | | | Gly | Gly | | | | | | | | | |

| | | | | | | | | | | | | | | | | |
|---|---|---|---|---|---|---|---|---|---|---|---|---|---|---|---|---|
| Mo | Trp | Gly | Gln | Pro | His | Gly | Gly | Ser | Trp | Gly | Gln | Pro | His | Gly | Gly | Ser | 79 |
| Hu | | | | | | | | Gly | | | | | | | | Gly | |

| | | | | | | | | | | | | | | | | |
|---|---|---|---|---|---|---|---|---|---|---|---|---|---|---|---|---|
| Mo | Trp | Gly | Gln | Pro | His | Gly | Gly | Gly | Trp | Gly | Gln | Gly | Gly | Gly | Thr | His | 95 |
| Hu | | | | | | | | | | | | | | | | | |

| | | | | | | | | | | | | | | | | |
|---|---|---|---|---|---|---|---|---|---|---|---|---|---|---|---|---|
| Mo | Asn | Gln | Trp | Asn | Lys | Pro | Ser | Lys | Pro | Lys | Thr | Asn | Leu | Lys | His | Val | 111 |
| Hu | Ser | | | | | | | | | | | | Met | | Met | | |

| | | | | | | | | | | | | | | | | |
|---|---|---|---|---|---|---|---|---|---|---|---|---|---|---|---|---|
| Mo | Ala | Gly | Ala | Ala | Ala | Ala | Gly | Ala | Val | Val | Gly | Gly | Leu | Gly | Gly | Tyr | 127 |
| Hu | | | | | | | | | | | | | | | | | |

| | | | | | | | | | | | | | | | | |
|---|---|---|---|---|---|---|---|---|---|---|---|---|---|---|---|---|
| Mo | Met | Leu | Gly | Ser | Ala | Met | Ser | Arg | Pro | Met | Ile | His | Phe | Gly | Asn | Asp | 143 |
| Hu | | | | | | | | | | | Ile | | | | | Ser | |

| | | | | | | | | | | | | | | | | |
|---|---|---|---|---|---|---|---|---|---|---|---|---|---|---|---|---|
| Mo | Trp | Glu | Asp | Arg | Tyr | Tyr | Arg | Glu | Asn | Met | Tyr | Arg | Tyr | Pro | Asn | Gln | 159 |
| Hu | Tyr | | | | | | | | | | | His | | | | | |

| | | | | | | | | | | | | | | | | |
|---|---|---|---|---|---|---|---|---|---|---|---|---|---|---|---|---|
| Mo | Val | Tyr | Tyr | Arg | Pro | Val | Asp | Gln | Tyr | Ser | Asn | Gln | Asn | Asn | Phe | Val | 175 |
| Hu | | | | | | | Met | | Glu | | | | | | | | |

| | | | | | | | | | | | | | | | | |
|---|---|---|---|---|---|---|---|---|---|---|---|---|---|---|---|---|
| Mo | His | Asp | Cys | Val | Asn | Ile | Thr | Ile | Lys | Gln | His | Thr | Val | Thr | Thr | Thr | 191 |
| Hu | | | | | | | | | | | | | | | | | |

| | | | | | | | | | | | | | | | | |
|---|---|---|---|---|---|---|---|---|---|---|---|---|---|---|---|---|
| Mo | Thr | Lys | Gly | Glu | Asn | Phe | Thr | Glu | Thr | Asp | Val | Lys | Met | Met | Glu | Arg | 207 |
| Hu | | | | | | | | | | | | | | | | | |

| | | | | | | | | | | | | | | | | |
|---|---|---|---|---|---|---|---|---|---|---|---|---|---|---|---|---|
| Mo | Val | Val | Glu | Gln | Met | Cys | Val | Thr | Gln | Tyr | Gln | Lys | Glu | Ser | Gln | Ala | 223 |
| Hu | | | | | | | Ile | | | | | Glu | Arg | | | | |

| | | | | | | | | | | | | | | | | |
|---|---|---|---|---|---|---|---|---|---|---|---|---|---|---|---|---|
| Mo | Tyr | Tyr | Asp | Gly | Arg | Arg | Ser | Ser | Ser | Thr | Val | Leu | Phe | Ser | Ser | Pro | 239 |
| Hu | | | | Gln | --- | --- | | Gly | | Met | | | | | | | |

| | | | | | | | | | | | | | | | |
|---|---|---|---|---|---|---|---|---|---|---|---|---|---|---|---|
| Mo | Pro | Val | Ile | Leu | Leu | Ile | Ser | Phe | Leu | Ile | Phe | Leu | Ile | Val | Gly | 254 |
| Hu | | | | | | | | | | | | | | | | |

Predicted amino acid sequence of mouse PrP and the amino acid differences between mouse and human PrP.

FIG. 3

| Mo | Met | Ala | Asn | Leu | --- | --- | Gly | Tyr | Trp | Leu | Leu | Ala | Leu | Phe | Val | Thr | 14 |
|----|-----|-----|-----|-----|-----|-----|-----|-----|-----|-----|-----|-----|-----|-----|-----|-----|-----|
| Bo |     | Val | Lys | Ser | His | Ile |     | Ser |     | Ile |     | Val |     |     |     | Ala |    |

| Mo | Met | Trp | Thr | Asp | Val | Gly | Leu | Cys | Lys | Lys | Arg | Pro | Lys | Pro | Gly | Gly | 30 |
|----|-----|-----|-----|-----|-----|-----|-----|-----|-----|-----|-----|-----|-----|-----|-----|-----|----|
| Bo |     |     | Ser |     |     |     |     |     |     |     |     |     |     |     |     |     |    |

| Mo | --- | Trp | Asn | Thr | Gly | Gly | Ser | Arg | Tyr | Pro | Gly | Gln | Gly | Ser | Pro | Gly | 45 |
|----|-----|-----|-----|-----|-----|-----|-----|-----|-----|-----|-----|-----|-----|-----|-----|-----|----|
| Bo |     |     |     |     |     |     |     |     |     |     |     |     |     |     |     |     |    |

| Mo | Gly | Asn | Arg | Tyr | Pro | Pro | Gln | Gly | Gly | --- | Thr | Trp | Gly | Gln | Pro | His | 60 |
|----|-----|-----|-----|-----|-----|-----|-----|-----|-----|-----|-----|-----|-----|-----|-----|-----|----|
| Bo |     |     |     |     |     |     |     |     |     | Gly | Gly |     |     |     |     |     |    |

| Mo | Gly | Gly | Gly | Trp | Gly | Gln | Pro | His | Gly | Gly | Ser | Trp | Gly | Gln | Pro | His | 78 |
|----|-----|-----|-----|-----|-----|-----|-----|-----|-----|-----|-----|-----|-----|-----|-----|-----|----|
| Bo |     |     |     |     |     |     |     |     |     |     | Gly |     |     |     |     |     |    |

| Mo | Gly | Gly | Ser | Trp | Gly | Gln | Pro | His | Gly | Gly | Gly | Trp | Gly | Gln | --- | --- | 90 |
|----|-----|-----|-----|-----|-----|-----|-----|-----|-----|-----|-----|-----|-----|-----|-----|-----|----|
| Bo |     |     | Gly |     |     |     |     |     |     |     |     |     |     |     | Pro | His |    |

| Mo | --- | --- | --- | --- | --- | --- | Gly | Gly | Gly | Thr | His | Asn | Gln | Trp | Asn | Lys | 100 |
|----|-----|-----|-----|-----|-----|-----|-----|-----|-----|-----|-----|-----|-----|-----|-----|-----|-----|
| Bo | Gly | Gly | Gly | Gly | Trp | Gly | Gln |     |     |     |     |     | Gly |     |     |     |     |

| Mo | Pro | Ser | Lys | Pro | Lys | Thr | Asn | Leu | Lys | His | Val | Ala | Gly | Ala | Ala | Ala | 116 |
|----|-----|-----|-----|-----|-----|-----|-----|-----|-----|-----|-----|-----|-----|-----|-----|-----|-----|
| Bo |     |     |     |     |     |     |     | Met |     |     |     |     |     |     |     |     |     |

| Mo | Ala | Gly | Ala | Val | Val | Gly | Gly | Leu | Gly | Gly | Tyr | Met | Leu | Gly | Ser | Ala | 132 |
|----|-----|-----|-----|-----|-----|-----|-----|-----|-----|-----|-----|-----|-----|-----|-----|-----|-----|
| Bo |     |     |     |     |     |     |     |     |     |     |     |     |     |     |     |     |     |

| Mo | Met | Ser | Arg | Pro | Met | Ile | His | Phe | Gly | Asn | Asp | Trp | Glu | Asp | Arg | Tyr | 148 |
|----|-----|-----|-----|-----|-----|-----|-----|-----|-----|-----|-----|-----|-----|-----|-----|-----|-----|
| Bo |     |     |     |     | Leu |     |     |     |     |     | Ser |     | Tyr |     |     |     |     |

| Mo | Try | Arg | Glu | Asn | Met | Tyr | Arg | Tyr | Pro | Asn | Gln | Val | Tyr | Tyr | Arg | Pro | 164 |
|----|-----|-----|-----|-----|-----|-----|-----|-----|-----|-----|-----|-----|-----|-----|-----|-----|-----|
| Bo |     |     |     |     |     | His |     |     |     |     |     |     |     |     |     |     |     |

| Mo | Val | Asp | Gln | Tyr | Ser | Asn | Gln | Asn | Asn | Phe | Val | His | Asp | Cys | Val | Asn | 180 |
|----|-----|-----|-----|-----|-----|-----|-----|-----|-----|-----|-----|-----|-----|-----|-----|-----|-----|
| Bo |     |     |     |     |     |     |     |     |     |     |     |     |     |     |     |     |     |

| Mo | Ile | Thr | Ile | Lys | Gln | His | Thr | Val | Thr | Thr | Thr | Thr | Lys | Gly | Glu | Asn | 200 |
|----|-----|-----|-----|-----|-----|-----|-----|-----|-----|-----|-----|-----|-----|-----|-----|-----|-----|
| Bo |     |     |     | Val |     | Glu |     |     |     |     |     |     |     |     |     |     |     |

| Mo | Phe | Thr | Glu | Thr | Asp | Val | Lys | Met | Met | Glu | Arg | Val | Val | Glu | Gln | Met | 212 |
|----|-----|-----|-----|-----|-----|-----|-----|-----|-----|-----|-----|-----|-----|-----|-----|-----|-----|
| Bo |     |     |     |     |     |     |     | Ile |     |     |     |     |     |     |     |     |     |

| Mo | Cys | Val | Thr | Gln | Tyr | Gln | Lys | Glu | Ser | Gln | Ala | Tyr | Tyr | Asp | Gly | Arg | 228 |
|----|-----|-----|-----|-----|-----|-----|-----|-----|-----|-----|-----|-----|-----|-----|-----|-----|-----|
| Bo |     |     |     |     |     |     |     |     |     |     |     |     |     |     | Gln | --- |     |

| Mo | Arg | Ser | Ser | Ser | Thr | Val | Leu | Phe | Ser | Ser | Pro | Pro | Val | Ile | Leu | Leu | 244 |
|----|-----|-----|-----|-----|-----|-----|-----|-----|-----|-----|-----|-----|-----|-----|-----|-----|-----|
| Bo | --- | Gly | Ala |     |     | Val | Ile |     |     |     |     |     |     |     |     |     |     |

| Mo | Ile | Ser | Phe | Leu | Ile | Phe | Leu | Ile | Val | Gly |     |     |     |     |     |     | 254 |
|----|-----|-----|-----|-----|-----|-----|-----|-----|-----|-----|-----|-----|-----|-----|-----|-----|-----|
| Bo |     |     |     |     |     |     |     |     |     |     |     |     |     |     |     |     |     |

Predicted amino acid sequence of mouse PrP and the amino acid differences between mouse and bovine PrP.

*FIG. 4*

| | | | | | | | | | | | | | | | |
|---|---|---|---|---|---|---|---|---|---|---|---|---|---|---|---|
| Mo | Met | Ala | Asn | Leu | --- | --- | Gly | Tyr | Trp | Leu | Leu | Ala | Leu | Phe | Val | Thr | 14 |
| Sh | | Val | Lys | Ser | His | Ile | | Ser | | Ile | | Val | | | | Ala | |

Mo Met Trp Thr Asp Val Gly Leu Cys Lys Lys Arg Pro Lys Pro Gly Gly 30
Sh           Ser

Mo --- Trp Asn Thr Gly Gly Ser Arg Tyr Pro Gly Gln Gly Ser Pro Gly 45
Sh

Mo Gly Asn Arg Tyr Pro Pro Gln Gly Gly --- Thr Trp Gly Gln Pro His 60
Sh                                  Gly Gly

Mo Gly Gly Gly Trp Gly Gln Pro His Gly Gly Ser Trp Gly Gln Pro His 76
Sh                                        Gly

Mo Gly Gly Ser Trp Gly Gln Pro His Gly Gly Gly --- Trp Gly Gln Gly 91
Sh                                            Gly

Mo Gly Gly Thr His Asn Gln Trp Asn Lys Pro Ser Lys Pro Lys Thr Asn 107
Sh       Ser --- His Ser

Mo Leu Lys His Val Ala Gly Ala Ala Ala Ala Gly Ala Val Val Gly Gly 123
Sh Met

Mo Leu Gly Gly Tyr Met Leu Gly Ser Ala Met Ser Arg Pro Met Ile His 139
Sh                                              Leu

Mo Phe Gly Asn Asp Trp Glu Asp Arg Tyr Tyr Arg Glu Asn Met Tyr Arg 155
Sh             Tyr

Mo Tyr Pro Asn Gln Val Tyr Tyr Arg Pro Val Asp Gln Tyr Ser Asn Gln 171
Sh

Mo Asn Asn Phe Val His Asp Cys Val Asn Ile Thr Ile Lys Gln His Thr 187
Sh                                       Val

Mo Val Thr Thr Thr Thr Lys Gly Glu Asn Phe Thr Glu Thr Asp Val Lys 203
Sh                                                        Ile

Mo Met Met Glu Arg Val Val Glu Gln Met Cys Val Thr Gln Tyr Gln Lys 219
Sh Ile                                    Ile                  Arg

Mo Glu Ser Gln Ala Tyr Tyr Asp Gly Arg Arg Ser Ser Ser Thr Val Leu 235
Sh                         Gln --- ---     Gly Ala     Val Ile

Mo Phe Ser Ser Pro Pro Val Ile Leu Leu Ile Ser Phe Leu Ile Phe Leu 251
Sh

Mo Ile Val Gly 254
Sh

Predicted amino acid sequence of mouse PrP and the amino acid
differences between mouse and sheep PrP.

Sequence alignment (positions 200–230):

Consensus: `T D V K M M E R V V E Q M C V T Q Y Q K E S Q A Y Y D G R R - S`

| Clone | 200 T | D | V | K | M(204) | M(205) | E | R | V | V | 210 E | Q | M | C | V(214) | T | Q(216) | Y | Q(218) | K | 220 E | S | Q | A | Y | Y | D | G | R | R | - | 230 S |
|---|---|---|---|---|---|---|---|---|---|---|---|---|---|---|---|---|---|---|---|---|---|---|---|---|---|---|---|---|---|---|---|---|
| Mo | | | | | | | | | | | | | | | | | | | | | | | | | | | | | | | | |
| MH2M | | | | | | | | | | | | | | | | | | | | | | | | | | | | | | | | |
| MH3 | | | | | I | I | | | | | | | | | | | | | | | | | | | | | | | | | | |
| SHa | | | | | I | I | | | | | T | | | | | | | | | | | | | | | | | | | | | |
| Hu | | | | | | | | | | | T | | | | | | | | | | | | | | | | | | | | | |
| MHMHu(A+B) | | | | | | | | | | | I | | | | | | | | | | E | R | | | | | Q | – | – | | | G |
| MHMHuA | | | | | | | | | | | I | | | | | | | | | | E | R | | | | | Q | – | – | | | G |
| M3HuA & MH2HuA | | | | | | | | | | | I | | | | | | | | | | E | R | | | | | | | | | | |
| MH3HuA | | | | | I | I | | | | | I | | | | | | | | | | E | R | | | | | | | | | | |
| MHMHuB | | | | | | I | | | | | I | | | | | | | | | | E | R | | | | | Q | – | – | | | G |
| MHMHuA1 | | | | | | | | | | | I | | | | | | | | | | | | | | | | | | | | | |
| MHMHuA2 | | | | | | | | | | | | | | | | | | | | | E | R | | | | | | | | | | |
| MHMHuA3 | | | | | | | | | | | | | | | | | | | | | E | | | | | | | | | | | |
| MHMHuA4 | | | | | | | | | | | | | | | | | | | | | | R | | | | | | | | | | |
| MHMHuA5 | | | | | | | | | | | I | | | | | | | | | | E | | | | | | | | | | | |
| MHMK218 | | | | | | | | | | | | | | | | | | | K | | | | | | | | | | | | | |
| MHMI218 | | | | | | | | | | | | | | | | | | | I | | | | | | | | | | | | | |
| MHMA218 | | | | | | | | | | | | | | | | | | | A | | | | | | | | | | | | | |
| MHMW218 | | | | | | | | | | | | | | | | | | | W | | | | | | | | | | | | | |
| MHMP218 | | | | | | | | | | | | | | | | | | | P | | | | | | | | | | | | | |
| MHMR216 | | | | | | | | | | | | | | | | | R | | | | | | | | | | | | | | | |
| MHMHuR216 | | | | | | | | | | | | | | | | | R | | | | E | | | | | | | | | | | |
| MHME214 | | | | | | | | | | | | | | | E | | | | | | | | | | | | | | | | | |
| MHMK214 | | | | | | | | | | | | | | | K | | | | | | | | | | | | | | | | | |
| MHMA214 | | | | | | | | | | | | | | | A | | | | | | | | | | | | | | | | | |
| MHMW214 | | | | | | | | | | | | | | | W | | | | | | | | | | | | | | | | | |
| MHMP214 | | | | | | | | | | | | | | | P | | | | | | | | | | | | | | | | | |

Pharmacophore geometrics for the
PPMF binding site of PrP^C

Errors estimated by calculating 3 X r

| FIG. 11A |
| FIG. 11B |

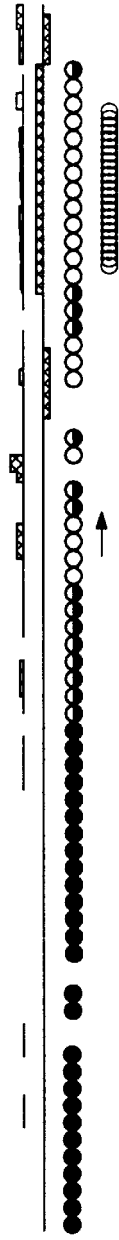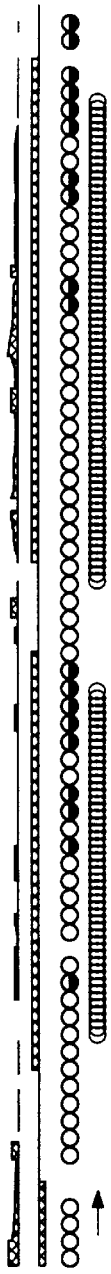
FIG. 15

NUCLEIC ACID ENCODING PRION PROTEIN VARIANT

GOVERNMENT RIGHTS

The United States Government may have certain rights in this application pursuant to Grant Nos. NS14069, AG08967, AG02132, NS22786 and AG10770 awarded by the National Institutes of Health.

FIELD OF THE INVENTION

This invention relates generally to proteins, functionally equivalent pharmacophores and methods of creating a gene to make prion resistant animals. More specifically, this invention relates to (1) a discontinuous epitope of PrP protein, (2) prion protein modulator factor (PPMF) which binds the epitope, (3) functional pharmacophores of (1) and (2) and (4) prion resistant animals and their PrP genes.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") [Bolton et al., *Science* 218:1309–11 (1982); Prusiner et al., *Biochemistry* 21:6942–50 (1982); McKinley et al., *Cell* 35:57–62 (1983)]. Complete prion protein-encoding genes have since been cloned, sequenced and expressed in transgenic animals. $PrP^C$ is encoded by a single-copy host gene [Basler et al., *Cell* 46:417–28 (1986)] and is normally found at the outer surface of neurons. A leading hypothesis is that prion diseases result from conversion of $PrP^C$ into a modified form called $PrP^{Sc}$.

It appears that the scrapie isoform of the prion protein ($PrP^{Sc}$) is necessary for both the transmission and pathogenesis of the transmissible neurodegenerative diseases of animals and humans. See Prusiner, S. B., "Molecular biology of prion disease," *Science* 252:1515–1522 (1991). The most common prion diseases of animals are scrapie of sheep and goats and bovine spongiform encephalopathy (BSE) of cattle [Wilesmith, J. and Wells, *Microbiol. Immunol.* 172:21–38 (1991)]. Four prion diseases of humans have been identified: (1) kuru, (2) Creutzfeldt-Jakob Disease (CJD), (3) Gerstmann-Strassler-Scheinker Disease (GSS), and (4) fatal familial insomnia (FFI) [Gajdusek, D. C., *Science* 197:943–960 (1977); Medori et al., *N. Engl. J. Med.* 326:444–449 (1992)]. The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene [Hsiao et al., *Neurology* 40:1820–1827 (1990); Goldfarb et al., *Science* 258:806–808 (1992); Kitamoto et al., *Proc. R. Soc. Lond.* 343:391–398. Iatrogenic CJD has been caused by human growth hormone derived from cadaveric pituitaries as well as dura mater grafts [Brown et al., *Lancet* 340:24–27 (1992)]. Despite numerous attempts to link CJD to an infectious source such as the consumption of scrapie infected sheep meat, none has been identified to date [Harries-Jones et al., *J. Neurol. Neurosurg. Psychiatry* 51:1113–1119 (1988)] except in cases of iatrogenically induced disease. On the other hand, kuru, which for many decades devastated the Fore and neighboring tribes of the New Guinea highlands, is believed to have been spread by infection during ritualistic cannibalism [Alpers, M. P., *Slow Transmissible Diseases of the Nervous System,* Vol. 1, S. B. Prusiner and W. J. Hadlow, eds. (New York: Academic Press), pp. 66–90 (1979)].

The initial transmission of CJD to experimental primates has a rich history beginning with William Hadlow's recognition of the similarity between kuru and scrapie. In 1959, Hadlow suggested that extracts prepared from patients dying of kuru be inoculated into nonhuman primates and that the animals be observed for disease that was predicted to occur after a prolonged incubation period [Hadlow, W. J., *Lancet* 2:289–290 (1959)]. Seven years later, Gajdusek, Gibbs and Alpers demonstrated the transmissibility of kuru to chimpanzees after incubation periods ranging form 18 to 21 months [Gajdusek et al., *Nature* 209:794–796 (1966)]. The similarity of the neuropathology of kuru with that of CJD [Klatzo et al., *Lab Invest.* 8:799–847 (1959)] prompted similar experiments with chimpanzees and transmissions of disease were reported in 1968 [Gibbs, Jr. et al., *Science* 161:388–389 (1968)]. Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using nonhuman primates, some cases of human prion disease have been transmitted to rodents but apparently with less regularity [Gibbs, Jr. et al., *Slow Transmissible Diseases of the Nervous System,* Vol. 2, S.B. Prusiner and W. J. Hadlow, eds. (New York: Academic Press), pp. 87–110 (1979); Tateishi et al., *Prion Diseases of Humans and Animals,* Prusiner et al., eds. (London: Ellis Horwood), pp. 129–134 (1992)].

The infrequent transmission of human prion disease to rodents has been cited as an example of the "species barrier" first described by Pattison in his studies of passaging the scrapie agent between sheep and rodents [Pattison, I. H., *NINDB Monograph* 2, D. C. Gajdusek, C. J. Gibbs Jr. and M. P. Alpers, eds. (Washington, D.C.: U.S. Government Printing), pp. 249–257 (1965)]. In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice [Scott et al., *Cell* 59:847–857 (1989)]. SHaPrP differs from MoPrP at 16 positions out of 254 amino acid residues [Basler et al., *Cell* 46:417–428 (1986); Locht et al., *Proc. Natl. Acad. Sci. USA* 83:6372–6376 (1986)]. Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD [Koch et al., *N. Engl. J. Med.* 313:731–733 (1985); Brown et al., *Lancet* 340:24–27 (1992); Fradkin et al., *JAMA* 265:880–884 (1991); Buchanan et al., *Br. Med. J.* 302:824–828 (1991)]. Fortunately, recombinant HGH is now used, although the seemingly remote possibility has been raised that increased expression of wtPrP$^C$ stimulated by high HGH might induce prion disease [Lasmezas et al., *Biochem. Biophys. Res. Commun.* 196:1163–1169 (1993)]. That the HGH prepared from pituitaries was contaminated with prions is supported by the transmission of prion disease to a monkey 66 months after inoculation with a suspect lot of HGH (Gibbs, Jr. et al., *N. Engl. J. Med.* 328:358–359 (1993)]. The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone [Healy et al., *Br. J. Med.* 307:517–518 (1993); Cochius et al., *Aust. N.Z. J. Med.* 20:592–593 (1990); Cochius et al., *J. Neurol. Neurosurg. Psychiatry* 55:1094–1095 (1992)] as well as at least 11 patients receiving dura mater grafts [Nisbet et al., *J. Am. Med. Assoc.* 261:1118 (1989); Thadani et al., *J. Neurosurg.* 69:766–769 (1988); Willison et al., *J. Neurosurg. Psychiatric* 54:940 (1991); Brown et al., *Lancet* 340:24–27 (1992)]. These cases of iatrogenic CJD underscore the need for screening pharmaceuticals that might possibly be contaminated with prions.

Recently, two doctors in France were charged with involuntary manslaughter of a child who had been treated with growth hormones extracted from corpses. The child developed Creutzfeldt-Jakob Disease. (See *New Scientist,* Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist, Nov.* 20, 1993, page 10.) In view of such, there clearly is a need for a convenient, cost-effective assay for testing sample materials for the presence of prions which cause CJD.

Such a method is provided in U.S. Pat. No. 5,565,186, issued Oct. 15, 1996, which provides for inoculating transgenic mice with a sample suspected of containing prions and waiting to see if the mice develop symptoms of prion disease. The present invention provides a protein designated PPMF which has a range of uses including facilitating the speed and sensitivity of assays which use transgenic animals to detect prions.

SUMMARY OF THE INVENTION

Prion Protein Modulator Factor (PPMF) is disclosed which protein is characterized by binding to PrP$^C$ and facilitating a conformation change from PrP$^C$ to PrP$^{Sc}$. The protein PPMF is species specific meaning that PPMF from one species of mammal will only bind to PrP$^C$ of the same or a genetically similar species. PPMF binds to a discontinuous epitope of PrP protein and the epitope is also disclosed in terms of its amino acid sequence but, more importantly, in terms of its 3-dimensional configuration which defines the negative image of the binding surface of PPMF. Using the 3-dimensional coordinates defining the binding surface of both PPMF and the discontinuous epitope of PrP protein, functionally equivalent pharmacophores are disclosed and described as are methods of generating such pharmacophores. PPMF, its binding epitope on PrP protein and functionally equivalent pharmacophores of each are useful in assays and as therapeutic agents. By identifying the PrP$^C$ binding epitope for PPMF, PrP genes can be created which render an animal resistant to prion disease.

An aspect of the invention is the 3-dimensionally defined discontinuous epitope of PrP protein and functional equivalent pharmacophores.

Another aspect of the invention is PPMF and functionally equivalent pharmacophores with a 3-dimensionally defined surface in the negative image of the discontinuous epitope of PrP protein.

Another aspect of the invention is a PrP gene with codon substitutions made at position which encode amino acids of the discontinuous epitope which substitutes are made in a manner which encodes a protein which (1) binds PPMF more readily than native PrP or (2) does not bind PPMF, thereby providing genes which can provide transgenic animals which are resistant to prion infection.

Another aspect of the invention comprises administering PPMF to a transgenic animal with a chimeric artificial PrP gene comprising portions of the host animal e.g., end portions of a host animal and a middle portion of a genetically diverse test animal wherein the middle portion includes a specific alterations designed to match that of a disease state of such a host. The PPMF can be administered to a transgenic animal containing a chimeric gene in order to reduce the time for prion disease to be exhibited.

The artificial gene includes a sequence such that when it is inserted into the genome of an animal (such as a mouse), the animal is rendered susceptible to infection with prions which normally would infect only a specific species of genetically diverse animal (such as a human, cow, sheep, pig, chicken, cat or dog). The artificial PrP gene may be comprised partially or completely of an artificial polynucleotide sequence, i.e. codon sequences not present in any native PrP gene sequence. Alternatively, the artificial gene may be comprised of the codon sequence of a host animal with one or more codon substitutions being made wherein the substitutions are preferably corresponding PrP gene codons from a genetically diverse animal, meaning that PrP gene differs from the PrP gene of the host animal by 20 or more codons. Transgenic animals containing elevated levels of expression of the PrP gene which can be obtained for example, by over expression of the gene with an enhanced promoter and/or with high copy numbers of the natural PrP gene of a genetically diverse animal are also disclosed. Hybrid transgenic animals include animals resulting from a cross between two transgenic animals and in particular a cross between a transgenic animal containing the entire prion protein gene of a genetically diverse animal (e.g., a mouse containing a human prion protein gene) and an animal with its endogenous prion protein gene disrupted (e.g., a mouse with an ablated prion protein gene). Hybrids also specifically include crossing a transgenic animal having a chimeric prion protein gene with an animal with its endogenous prion protein gene ablated.

PPMF or ligands which provides a surface that fits 3-dimensionally defined pharmacophores of the invention can be administered to transgenic animals which due to their genetic make up will develop disease from inoculation with prions which would generally only infect a genetically diverse animal, e.g., a transgenic mouse will consistently become infected with prions which generally will only infect a human and symptoms of the infection will become apparent in a short period e.g., 100 days or less. The PPMF and/or pharmacophores is administered to transgenic animals that are used in assays to test samples of any given material to determine if the material includes prions which would infect another animal (such as a human) if the material were ingested or injected. Standardized prion preparations may be used to inoculate animals to create controls when carrying out an assay of the invention. The standardized prion preparation will always contain prions which will infect a genetically modified animal which animal will develop clinical signs of CNS dysfunction within a set period of time.

An aspect of the invention is a discontinuous epitope of PrP protein which is precisely defined in 3-dimensional space by distances and angles between amino acids making up the surface of the 3-dimensional epitope and functionally equivalent pharmacophores defining the same 3-dimensional space.

Another aspect of the invention is the binding site of PPMF to PrP which binding site is defined by the negative image of the defined 3-dimensional space of the epitope.

An object of the invention is to provide an isolated protein designated Prion Protein Modulator Factor (PPMF) which is characterized by binding to $PrP^C$ and facilitating a conformational change to $PrP^{Sc}$.

Another object of the invention is to provide transgenic animals such as cows and sheep which have their $PrP^C$ gene modified to express $PrP^C$ protein with a modified epitope for binding PPMF in a manner which renders the animal resistant to prion diseases.

Another object is to provide antibodies and pharmacophores which bind to PPMF (or epitopes or $PrP^C$ which binds PPMF) which molecules block PPMF—$PrP^C$ interaction and thereby act as a therapeutic for prion disease.

Another object of the invention is to provide for a method of testing samples for the presence of prions which preferably involves creating two groups of nonhuman mammals which have their genome altered so that they are susceptible to infection with prions which generally only infecting a genetically diverse animal. The first group of animals is infected with a test sample while being given PPMF and the second group is infected with a standardized prion preparation while being given PPMF. Both groups of mammals are observed and the presence of prions in the sample can be deduced if the first group of animals develop symptoms of prion infection. The time needed to develop symptoms is reduced by the PPMF.

An advantage of the invention is that the PPMF and pharmacophores thereof reduce the time needed for and increase the sensitivity of an assay.

A feature of the invention is that the PPMF and pharmacophores thereof do not bind $PrP^{Sc}$.

Another advantage is that the transgenic and hybrid animals injected with PPMF can quickly (100 days or less) detect prions in a sample at very low levels, e.g., 1 part per million, and even as low as 1 part per billion.

Still another advantage is that the transgenic and hybrid animals injected with PPMF can be used for an assay which is highly accurate, i.e., does not provide false positives and consistently determines the presence of prions.

Another object of the invention is to provide an assay whereby a sample is assayed for the presence of a $PrP^{Sc}$ by adding to the sample $PrP^C$ in combination with PPMF, a pharmacophore thereof or an antibody of $PrP^C$ which binds to $PrP^C$ at its $PrP^C$/PPMF binding epitope whereby the assay amplifies the amount of $PrP^{Sc}$ (if any) present in the sample.

These and other objects, advantages, and features of the invention will become apparent to those persons skilled in the art upon reading the details of the chimeric gene, assay method, and transgenic mouse as more fully described below.

BRIEF DESCRIPTION OF THE DRAWINGS

The file of this patent contains at least one drawing executed in color copies of this patent with color drawing(s) will be provided by the Patent and Trademark Office upon request and payment of the necessary fee.

FIG. 3 shows the amino acid sequence of mouse SEQ ID NO:1 PrP along with specific differences between mouse PrP and human SEQ ID NO:2 PrP;

FIG. 4 shows the amino acid sequence of mouse SEQ ID NO:1 PrP and specifically shows differences between mouse PrP and bovine SEQ ID NO:3 (cow) PrP;

FIG. 5 shows the amino acid sequence of mouse SEQ ID NO:1 PrP and specifically shows differences between mouse PrP and ovine SEQ ID NO:4 (sheep) PrP;

FIG. 8 shows a comparison of a number of PrP sequences with a segment of mouse SEQ ID NO:1 PrP showing differences;

In FIGS. 10, 12 and 14, the color scheme is: disulfide between $Cys^{179}$ and $Cys^{214}$, yellow; sites of glycosidation in $PrP^C$, i.e., $Asn^{181}$ and $Asn^{197}$, gold; hydrophobic globule composed of residues 113–126, red; helices, pink; loops, gray; residues 129–134, green, encompassing strand S2; the arrows span residues 129–131 and 161–163, as these show a closer resemblance to β-sheet. The structures were generated with the program DIANA Guntert, et al. J. Mol. Biol. 217,517–530 (1990) followed by energy minimization with AMBER 4.1. Pearlman, et al. AMBER 4.1 (UCSF 1995). Structure generation parameters are as follows: 2401 distance restraints (intraresidue, 858; sequential (i→i+1), 753; i→i+2, 195; i→i+3, 233; i→i+4, 109; and i→i+≧5, 253 for amino acid; hydrogen bond restraints, 44; distance restraints violations >>0.5A per structure, 30; AMBER energy, −1443±111 kcal/mol. Precision of structures: atomic RMSD for all backbone heavy atoms of residues 128–227, <<1.9A. The distance restraint violations and precision in some molecular moieties reflect the conformational heterogeneity of rPrP;

FIG. 12 ia a computer generated structure of the interaction of the hydrophobic globule, with van der Waals rendering the atoms in residues 113–127, with the first β-strand.

FIG. 14 is a computer generated stereoview highlighting in white the residues corresponding to point mutations leading to human prion diseases.

FIGS. 10, 12, 13 and 14 were generated with Midasplus.

Coordinates are deposited with the Brookhaven Protein Data Bank.

FIG. 15 shows the secondary structure diagram for rPrP. (SEQ ID NO:4) NOE connectivities are denoted by lines, where the thickness qualitatively represents the relative intensity (weak, medium or strong) of the NOE cross-peaks, and i designates the residue number for rPrP. $d\alpha_N(i,i+3)$ denotes an NOE between the α-proton of residue i and the amide proton of residue i+3. The long-range NOE line indicates by height the relative number of NOE cross-peaks between residues i→i+≧4. The α-carbon chemical shift index with contiguous up bars designating α-helix and down bars designating β-strand. Regions of secondary structure are depicted by helices for α-helices and broad arrows for β-strands. Hydrogen exchange was calculated from the intensity of proton NOE cross-peak between the amide and water: open circles for slow, filled for fast, and half-filled for medium exchange rate. No circle indicates spectral overlap or proline. The secondary structure diagram was created using the program Vince© (E. La Rosa, A. Stern, J. Hoch, Copyright 1996, Rowland Institute for Science).

Figure 16:
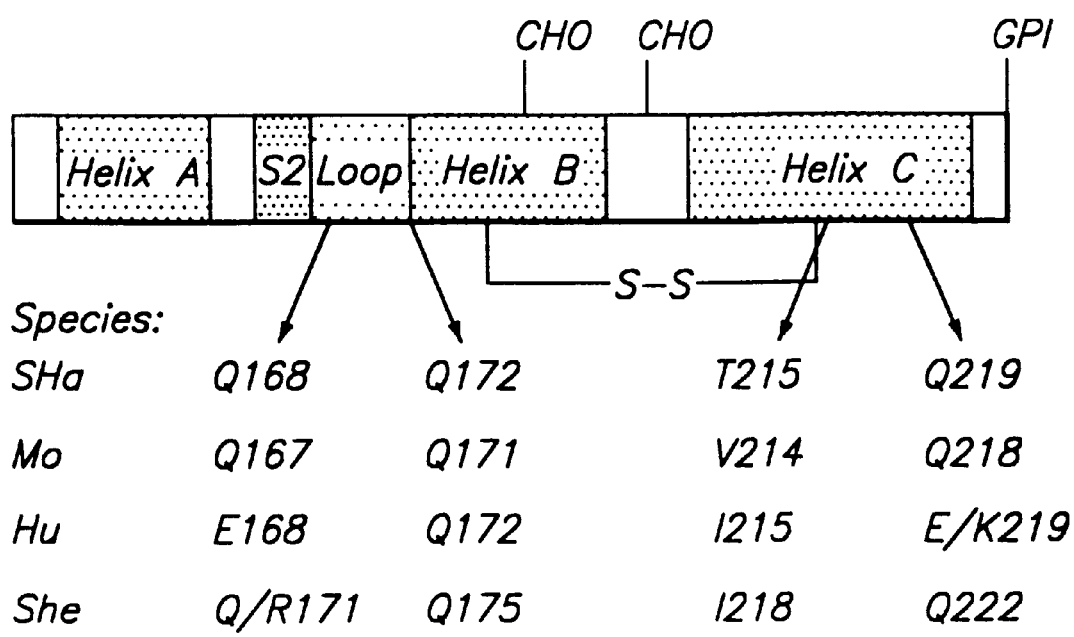

FIG. 16 schematically shows critical epitope positions for hamster, mouse, human and sheep PrP proteins and relates such to their position on the PrP molecule.

DETAILED DESCRIPTION OF PREFERRED EMBODIMENTS

Before the present proteins, pharmacophores, assay methodology, and transgenic and hybrid animals used in the assay are described, it is to be understood that this invention is not limited to particular protein, pharmacophores, assay methods, chimeric and artificial genes, prion preparation or transgenic and hybrid animals described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

The term "PPMF" is used for Prion Protein Modulator Factor which is a protein which can be glycosylated which is characterized by binding to $PrP^C$ and facilitating a conformational change from $PrP^C$ to $PrP^{Sc}$. The term encompasses any PPMF from any animal allowing for species specific differences between different species of animals. The PPMF compounds of the present invention are more particularly characterized herein.

A pharmacophore is a compound that has a specific biochemical activity which activity is obtained by the 3-dimensional physical shape of the compound and the electrochemical properties of the atoms making up the compound. Specific pharmacophores of the invention mimic (1) the discontinuous epitope on $PrP^C$ to which PPMF binds or (2) the surface of PPMF which bind to $PrP^C$. Thus a pharmacophores of the invention have a shape (i.e., the geometric specifications) as defined by FIG. 9 or the negative image thereof. The term mimetic is used here interchangeably with pharmacophore and covers peptides, and small molecules which mimic the shape and spatial positioning of the functional groups on the molecule being mimiced.

The terms "treatment", "treating" and "treat" and the like are used herein to generally mean obtaining a desired pharmacological and/or physiological effect. The effect may be prophylactic in terms of completely or partially preventing a prion disease or symptom thereof and/or may be therapeutic in terms of partially or completely curing a prion disease or adverse effect attributable to the disease. The "treatment" as used herein covers any treatment of a disease in a mammal, particularly a cow, pig, sheep, mouse or human, and includes:

(a) preventing prion disease or symptoms from occurring in a subject which may be predisposed to the disease or symptom or infected with prion particles but has not yet been diagnosed as having a prion disease which can include the use of gene therapy;

(b) inhibiting prion disease symptoms, i.e., arresting the development of prion disease; or (c) relieving a prion disease symptom, i.e., causing regression of prion disease or prion disease symptoms.

The term "isolated" shall mean separated away from its natural environment. An isolated protein is not necessarily separated away from all materials it is normally present with and may remain glycosylated.

The term "corresponding position" means the position of an amino acid in a peptide or the position of a codon in a nucleotide sequence corresponds to the same position in the sequence of a different species. FIGS. 3, 4 and 5 show corresponding positions for PrP proteins for different species. The amino acid sequence of PPMF also has corresponding positions from one species to another and corresponding positions for four different positions on the discontinuous epitope of $PrP^C$ (for five different proteins) are shown in Table 2.

The term "FVB" refers to a mouse strain commonly used in the production of transgenic mice. For purposes of this invention it should be noted that the mouse prion protein (PrP) gene is intact and mouse PrP is therefore expressed at normal levels.

The term "Prnp-% or Prnp-Abl" refers to a transgenic animal which has its PrP gene ablated with the "%" indicating that both alleles are ablated whereas o/+ indicates only one is ablated. Specifically, the animal being referred to is generally a transgenic mouse which has its PrP gene ablated i.e., a PrP knockout mouse. In that the PrP gene is disrupted no mouse PrP protein is expressed.

The term "sporadic CJD" abbreviated as "sCJD" refers to the most common manifestation of Creutzfeldt-Jakob Disease (CJD). This disease occurs spontaneously in individuals with a mean age of approximately 60 at a rate of 1 per million individuals across the earth.

The term "Iatrogenic CJD" abbreviated as "iCJD" refers to disease resulting from accidental infection of people with human prions. The most noted example of such is the accidental infection of children with human prions from contaminated preparations of human growth hormone.

The term "Familial CJD" refers to a form of CJD which occurs rarely in families and is inevitably caused by mutations of the human prion protein gene. The disease results from an autosomal dominant disorder. Family members who inherit the mutations succumb to CJD.

The term "Gerstmann-Strassler-Scheinker Disease" abbreviated as "GSS" refers to a form of inherited human prion disease. The disease occurs from an autosomal dominant disorder. Family members who inherit the mutant gene succumb to GSS.

The term "prion" shall mean an infectious particle known to cause diseases (spongiform encephalopathies) in humans and animals. The term "prion" is a contraction of the words "protein" and "infection" and the particles are comprised largely if not exclusively of $PrP^{Sc}$ molecules encoded by a PrP gene which expresses $PrP^C$ which changes conformation to become $PrP^{Sc}$. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Strassler-Scheinker Disease (GSS), and (4) fatal familial insomnia (FFI). As used herein prion includes all forms of prions causing all or any of these diseases or others in any animals used—and in particular in humans and in domesticated farm animals.

The terms "PrP gene" and "prion protein gene" are used interchangeably herein to describe genetic material which expresses proteins as shown in FIGS. 3–5 and polymorphisms and mutations such as those listed herein under the subheading "Pathogenic Mutations and Polymorphisms." Unless stated otherwise the term refers to the native wild-type gene and not to an artificially altered gene. The PrP gene can be from any animal including the "host" and "test" animals described herein and any and all polymorphisms and mutations thereof, it being recognized that the terms include other such PrP genes that are yet to be discovered. The term "PrP gene" refers generally to any gene of any species which encodes any form of a PrP amino acid sequences including any prion protein. Some commonly known PrP sequences are described in Gabriel et al., *Proc. Natl. Acad. Sci. USA* 89:9097–9101 (1992) which is incorporated herein by reference to disclose and describe such sequences. The sequences of PrP genes varies from species to species and the differences between a human PrP gene and that of a mouse, cow and sheep are shown respectively in FIGS. 3, 4 and 5.

The terms "standardized prion preparation," "prion preparation," "preparation" and the like are used interchangeably herein to describe a composition containing prions which composition is obtained from brain tissue of mammals which contain substantially the same genetic material as relates to PrP proteins, e.g., brain tissue from a set of mammals which exhibit signs of prion disease which mammals may comprise any of (1) a PrP chimeric transgene; (2) have an ablated endogenous PrP gene; (3) have a high copy number of PrP genes from a genetically diverse species; or (4) are hybrids with an ablated endogenous PrP gene and a PrP gene from a genetically diverse species. The mammals from which standardized prion preparations are obtained exhibit clinical signs of CNS dysfunction as a result of inoculation with prions and/or due to developing the disease due to their genetically modified make up, e.g., high copy number of PrP genes.

The term "artificial PrP gene" is used herein to describe a PrP gene which has one or more, preferably two more native codons replaced with different codons wherein the replaced codons are positioned so that, when expressed, form part of the $PrP^{C}$/PPMF binding epitope. The replacement codons preferably express an amino acid different from the native, e.g., basic to acidic, polar to non-polar.

The term "chimeric PrP gene" describes recombinantly constructed genes which when included in the genome of a host animal (e.g., a mouse) will render the mammal susceptible to infection from prions which naturally only infect a genetically diverse test mammal, e.g., human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions which only infect the genetically diverse mammal. Examples of artificial genes are mouse PrP genes encoding the sequence as shown in FIGS. 3, 4 and 5 with one or more different replacement codons selected from the codons shown in these Figures for humans, cows and sheep replacing mouse codons at the same position, with the proviso that not all the mouse codons are replaced with differing human, cow or sheep codons. Artificial PrP genes of the invention can include not only codons of genetically diverse animals but may include codons and codon sequences associated with genetic prion diseases such as CJD and codons and sequences not associated with any native PrP gene but which, when inserted into an animal render the animal susceptible to infection with prions which would normally only infect a genetically diverse animal. In one specific example the chimeric gene is comprised of the starting and terminating sequence (i.e., N- and C- terminal codons) of a PrP gene of a mammal of a host species (e.g. a mouse) and also containing a nucleotide sequence of a corresponding portion of a PrP gene of a test mammal of a second species (e.g. a human). A chimeric gene will, when inserted into the genome of a mammal of the host species, render the mammal susceptible to infection with prions which normally infect only mammals of the second species. A useful chimeric gene is MHu2M which contains the starting and terminating sequence of a mouse PrP gene and a nonterminal sequence region which is replaced with a corresponding human sequence which differs from a mouse PrP gene in a manner such that the protein expressed thereby differs at nine residues.

The term "genetic material related to prions" is intended to cover any genetic material which effects the ability of an animal to become infected with prions. Thus, the term encompasses any "PPMF gene," "PrP gene," "artificial PrP gene," "chimeric PrP gene" or "ablated PrP gene" which terms are defined herein as well as mutations and modifications of such which effect the ability of an animal to become infected with prions. Standardized prion preparations are produced using animals which all have substantially the same genetic material related to prion so that all of the animals will become infected with the same type of prions and will exhibit signs of infection at about the same time.

The terms "host animal" and "host mammal" are used to describe animals which will have their genome genetically and artificially manipulated so as to include genetic material which is not naturally present within the animal. For example, host animals include mice, hamsters and rats which have their endogenous PrP gene altered by the insertion of an artificial gene or by the insertion of a native PrP gene of a genetically diverse test animal.

The terms "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal. This is done by including PrP gene sequences of the test animal into the host animal, administering PPMF and inoculating the host animal with prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 20 or more codons, and most preferably 28–40 codons. Thus, a mouse PrP gene is genetically diverse with respect to the PrP gene of a human, cow or sheep, but is not genetically diverse with respect to the PrP gene of a hamster. In general, prions of a given animal will not infect a genetically diverse animal and PPMF of a given animal will not bind to $PrP^{C}$ of a genetically diverse animal.

The terms "ablated prion protein gene," "disrupted PrP gene," "ablated PrP gene", "$PrP^{0/0}$" and the like are used interchangeably herein to mean an endogenous prion protein gene which has been altered (e.g., add and/or remove nucleotides) in a manner so as to render the gene inoperative. Examples of nonfunctional PrP genes and methods of making such are disclosed in Bueler, H., et al "Normal development of mice lacking the neuronal cell-surface PrP protein" Nature 356, 577–582 (1992) which is incorporated herein by reference. Both alleles of the genes are disrupted.

The terms "hybrid animal," "transgenic hybrid animal" and the like are used interchangeably herein to mean an animal obtained from the cross-breeding of a first animal having an ablated endogenous PrP gene with a second animal which includes either (1) a chimeric gene or artificial PrP gene or (2) a PrP gene from a genetically diverse animal. For example a hybrid mouse is obtained by cross-breeding a mouse with an ablated mouse PrP gene with a mouse containing (1) human PrP genes (which may be present in high copy numbers) or (2) chimeric genes. The term hybrid includes any offspring of a hybrid including inbred offspring of two hybrids provided the resulting offspring is susceptible to infection with prions with normal infect only a genetically diverse species.

The terms "susceptible to infection" and "susceptible to infection by prions" and the like are used interchangeably herein to describe a transgenic or hybrid test animal which develops a prion disease if inoculated with prions which would normally only infect a genetically diverse test animal. The terms are used to describe a transgenic or hybrid animal such as a transgenic mouse Tg(MHu2M) which, without the chimeric PrP gene, would not be susceptible to infection with a human prion (less than 20% chance of infection) but with the chimeric gene is susceptible to infection with human prions (80% to 100% chance of infection).

The terms "resistant to infection", "resistant to infection with prions" and the like mean the animal includes a PrP gene which renders the animal resistant to prion disease when inoculated with an amount and type of prion which would be expected to cause prion disease in the animal. The resistant animals PrP gene includes non-native codons which express amino acids different from those of the native PrP gene which effect the $PrP^{C}$/PPMF binding site.

The term "incubation time" shall mean the time from inoculation of an animal with a prion until the time when the animal first develops detectable symptoms of disease resulting from the infection. A reduced incubation time is six months or less, preferable about 100 days±25 days or less, more preferably about 30 days±10 days or less.

Abbreviations used herein include:

BSE for bovine spongiform encephalopathy;

CJD for Creutzfeldt-Jakob Disease;

CNS for central nervous system;

FFI for fatal familial insomnia;

FVB for a standard inbred strain of mice often used in the production of transgenic mice since eggs of FVB mice are relatively large and tolerate microinjection of exogenous DNA relatively well.

GSS for Gerstmann-Strassler-Scheinker Disease;

Hu for human;

HuPPMF for human Prion Protein Modulator Factor;

HuPrP for a human PrP protein;

MHu2M for a chimeric mouse/human PrP gene wherein a region of the mouse PrP gene is replaced by a corresponding human sequence which differs from mouse PrP at 9 codons; $MHu2MPrP^{Sc}$ for the scrapie isoform of the chimeric human/mouse PrP gene;

Mo for mouse;

MoPPMF for mouse Prion Protein Modulator Factor;

MoPrP for a mouse PrP protein;

$MoPrP^{Sc}$ for the scrapie isoform of the mouse PrP protein;

PPMF for Prion Protein Modulator factor in general, i.e., that protein as in any species;

$Prnp^{0/0}$ for ablation of both alleles of an endogenous PrP protein gene, e.g., the MoPrP gene;

$PrP^{CJD}$ for the CJD isoform of a PrP gene;

$PrP^{Sc}$ for the scrapie isoform of the PrP protein;

SHa for a Syrian hamster;

SHaPrP for a Syrian hamster PrP protein;

Tg for transgenic;

Tg(BovPrP) for transgenic mice containing the complete cow PrP gene;

Tg(HuPrP) for transgenic mice containing the complete human PrP gene;

Tg(HuPrP)/$Prnp^{0/0}$ for a hybrid mouse obtained by crossing a mouse with a human PrP protein gene (HuPrP) with a mouse with both alleles of the endogenous PrP protein gene disrupted;

Tg(MHu2M) mice are transgenic mice of the invention which include the chimeric MHu2M gene;

Tg(MHu2M)/$Prnp^{0/0}$ for a hybrid mouse obtained by crossing a mouse with a chimeric PrP protein gene (MHu2M) with a mouse with both alleles of the endogenous PrP protein gene disrupted;

Tg(SHaPrP) for a transgenic mouse containing the PrP gene of a Syrian hamster;

Tg($SHaPrP^{+/0}$)81/$Prn\text{-}p^{0/0}$ for a particular line (81) of transgenic mice expressing SHaPrP, +/0 indicates heterozygous;

Tg(ShaPrP) for transgenic mice containing the complete sheep PrP gene.

General Aspects of the Invention

An understanding of PrP proteins and their characteristics provides background information to understand the function and characteristics of PPMF and equivalent pharmacophores. When the PrP gene is normally expressed it produces $PrP^C$ which is the protein in its "cellular" non-disease form. In order to develop a prion disease $PrP^C$ must be converted to $PrP^{Sc}$ which is the "scrapie" or disease causing form of the protein. Both $PrP^C$ and $PrP^{Sc}$ have the same amino acid sequence but a different 3-dimensional conformation. $PrP^{Sc}$ is referred to as a prion or infectious protein because when a mammal such as a mouse is inoculated with mouse prions (i.e., mouse $PrP^{Sc}$) the mouse will develop prion disease. However, prions are species specific meaning that if a mouse is inoculated with human or cow prions the mouse will not develop disease.

To begin characterization of PPMF it was noted that a transgenic mouse containing a human PrP gene would not get sick when inoculated with human prions. However, if the mouse PrP gene is ablated and the mouse genome includes the human PrP gene the mouse will get sick when inoculated with human prions. It was also noted that when a transgenic mouse was created with a chimeric (part mouse and part human) PrP gene the mouse would get sick when inoculated with human prions.

The above information was combined with results obtained with murine ScN2a cells showing that human COOH-terminal residues prevented chimeric human/mouse $PrP^C$ from being converted to the $PrP^{Sc}$ form.

Next it was found that by making particular substitutions in a PrP gene it is possible to prevent the conversion of $PrP^C$ to $PrP^{Sc}$. Specifically, it was found that by substituting human residues I215 or E/K219 for mouse V or Q respectively (at a corresponding position) the conversion of mouse $PrP^C$ into $PrP^{Sc}$ was prevented. Further, the substitution of R for Q171 in a mouse PrP gene prevents the formation of $MoPrP^{Sc}$. Substitutions at these relatively remote positions indicated that the $PrP^C$ protein was folded such that these positions were moved together. This was confirmed by producing an NMR image showing residues 170 and 171 in a loop adjacent to residues 214 and 218 on the $PrP^C$ protein (see FIG. 7).

In order for $PrP^C$ to convert to $PrP^{Sc}$ the $PrP^C$ must bind PPMF. Residues in the vicinity of 171 and 215 form a discontinuous epitope to which PPMF binds. If that binding is prevented (or occurs in a manner such that the PPMF is not released) than $PrP^C$ is not converted to $PrP^{Sc}$. By knowing the general area of the discontinuous binding epitope for PPMF on $PrP^C$ it is possible to replace codons (and thus amino acid residues) in that area and thereby effect $PPMF/PrP^C$ binding. However, knowledge of the linear sequences of amino acids in the area of the discontinuous epitope does not completely define the epitope.

Figure 7:
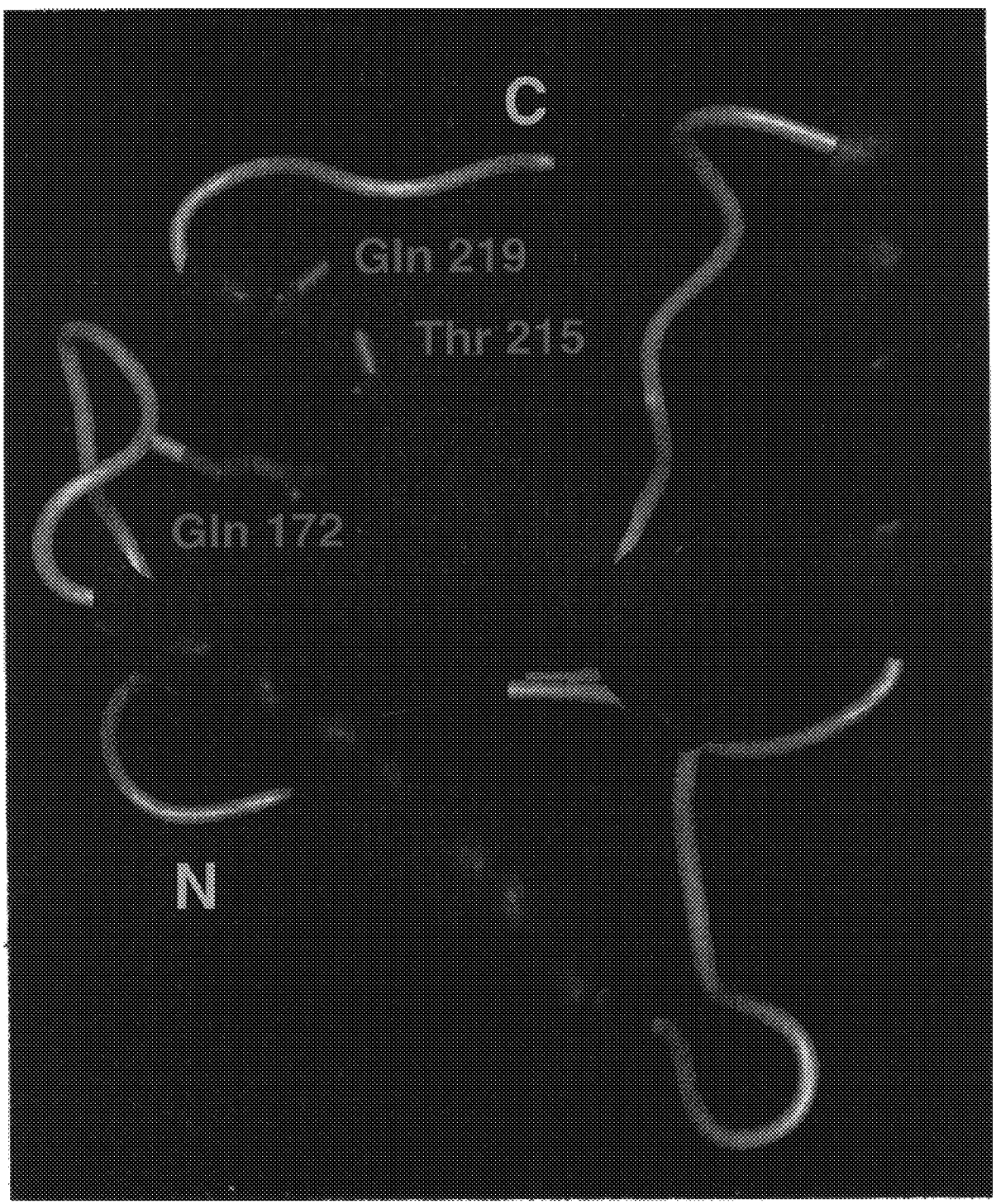
FIG. 7 is a schematic representation of $PrP^C$ showing the binding epitope for PPMF.

FIG. 7 shows the area of the discontinuous epitope on $PrP^C$ for binding of PPMF which area shows that the $PrP^C$ epitope is not a linear binding site. Specifically, FIG. 7 shows that the 215 and Gln 219 are on the outwardly facing surface of the discontinuous epitope as is Gln 172—these positions are for hamster $PrP^C$. The figure shows that due to the loops formed, the residues immediately before and after 215 and 219 are facing away from the surface presented by the $PrP^C$ epitope. Thus, it is not a linear sequence of amino acids which define the binding epitope surface but rather a surface defined in 3-dimensional space by the distances and angles shown in FIG. 9. The negative image of that surface defines the surface of PPMF to which the $PrP^C$ epitope binds.

Characterization PPMF

Prion Protein Modulator Factor (PPMF) is a species specific protein which binds to $PrP^C$ and facilitates a conformational change from $PrP^C$ to $PrP^{Sc}$. PPMF is further characterized by not binding to $PrP^{Sc}$ and acting as rate-limiting component in the conversion of $PrP^C$ to $PrP^{Sc}$. Specific species of PPMF are encoded by specific nucleotide sequences derived from a mammal selected from the group consisting of human, cow, sheep, mouse and hamster. PPMF is further characterized by diminishing the activation energy barrier between $PrP^C$ and $PrP^{Sc}$ thereby facilitating the formation of $PrP^{Sc}$. In addition to these generalized characteristics, PPMF has the following specific identifying characteristics.

Corresponding positions between the residues for different PrP proteins are provided in FIGS. 3, 4 and 5. Corresponding positions for five different PrP proteins are shown in Table 2. PPMF is not affected by a change in residue at position 216, 220, 221 or 222 of human $PrP^C$ or a corresponding position in a different species. As shown in FIG. 7, the position next to a position which affects binding is likely to be facing away from the epitope surface. The binding of PPMF to $PrP^C$ is affected by residues at position 215 and 219 in hamster $PrP^C$ and corresponding positions in the $PrP^C$ protein of different species. Binding of PPMF to $PrP^C$ is affected by the residue at position 172 in sheep $PrP^C$ and the corresponding residue in the $PrP^C$ protein of different species. This would generally not be expected as the position 171 is some distance from the 214–219 region. However, the folding of $PrP^C$ proteins as per FIG. 7 explains this. Finally, PPMF binds to a discontinuous epitope on $PrP^C$ which epitope comprises residues 172, 215 and 219 in the human PrP protein and corresponding residues in the PrP protein of different species.

Use and Operation of PPMF

In order for a mammal to develop a prion disease, $PrP^C$ must be converted to $PrP^{Sc}$, i.e., prions must be formed. In order for prions to be formed, three compounds must be present which are $PrP^C$, $PrP^{Sc}$, and PPMF. Because PPMF is a rate-limiting compound in the formation of prions, (if not recycled) an animal which is infected with prions (i.e. $PrP^{Sc}$) may develop symptoms of prion disease very slowly. This is not desirable when the animal is being used as a test animal in order to determine if the prions are present within a sample. Thus, the administration of PPMF to such test animals can greatly reduce the amount of time necessary for the formation of prions and thereby reduce the amount of time necessary to pass before the observation of the first symptoms of prion disease.

Figure 6:
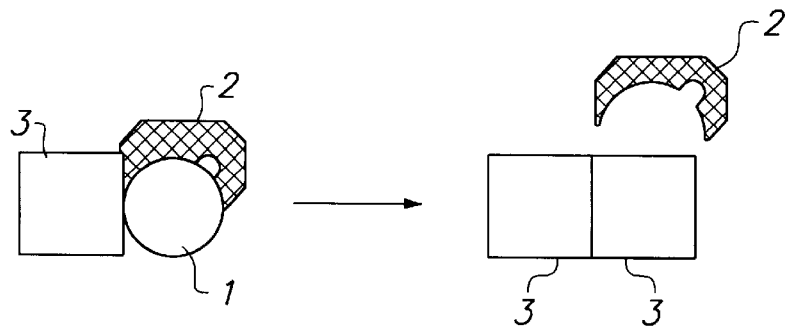
FIG. 6 is a schematic representation of how PPMF converts $PrP^C$ to $PrP^{Sc}$.

FIG. 6 schematically shows how PPMF is involved in the conversion of $PrP^C$ to $PrP^{Sc}$. Specifically, $PrP^C$ is represented by the circle 1 and is present in a non-diseased normal animal as is PPMF represented by the C-shaped molecule 2. When PPMF binds to $PrP^C$ it allows for the formation of a complex which includes $PrP^{Sc}$ represented by the squares 3. After the complex is formed the $PrP^C$ is converted to $PrP^{Sc}$ and the PPMF is released as it does not bind $PrP^{SC}$.

Figure 9:
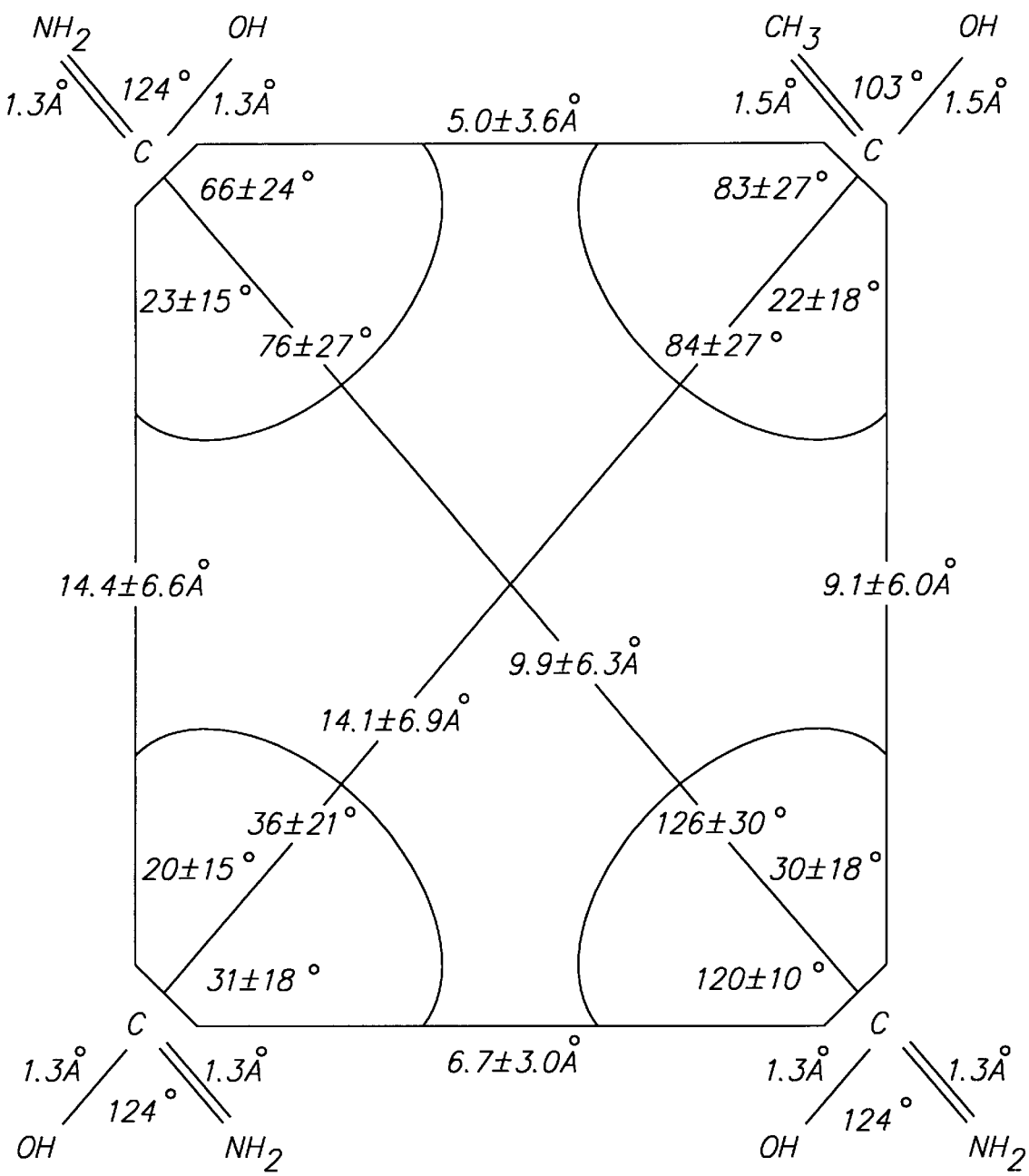
FIG. 9 shows the 3-dimensional geometries of the discontinuous binding site of $PrP^C$.

Based on both an understanding of how $PrP^C$ is converted to $PrP^{Sc}$ as shown in FIG. 6 and the 3-dimensional conformation of the $PrP^C$ binding epitope as shown in FIG. 9 it is possible to construct a variety of therapeutic compounds which allow for the treatment of prion disease. The specific amino acid positions and coordinates of FIG. 9 are provided with respect to hamster $PrP^C$. However, using Table 2 it is possible to substitute the amino acids shown for corresponding positions for human, mouse, cow and sheep and the chimeric PrP protein. With this information it is possible to generate a variety of pharmacophores which mimic the epitope surface of $PrP^C$. Such pharmacophores will bind to the binding surface of PPMF and as such can be used to assay for the presence of PPMF, determine its concentration within a sample, and, more importantly, be used as a therapeutic for the treatment of prion disease.

By knowing the amino acids positioned on the surface of the $PrP^C$ epitope and knowing the precise 3-dimensional position of the residues as shown within FIG. 9, the 3-dimensional surface of the binding surface of PPMF can be generated. The binding surface of PPMF to $PrP^C$ is, of course, the negative image of the epitope binding surface of $PrP^C$. By knowing the negative image of the epitope surface of $PrP^C$ (i.e., the 3-dimensional coordinates of the binding surface of PPMF) it is possible to generate PPMF pharmacophores. The PPMF pharmacophores have a variety of specific uses. Firstly, the pharmacophores of PPMF can be bound to the surface and be used to assay for the presence of $PrP^C$ in that they bind to the $PrP^C$ epitope. Secondly, when the pharmacophores are designed so as to allow for the conversion of $PrP^C$ to $PrP^{Sc}$ they can be administered to two animals such as mice which are being inoculated with a sample in order to test for the presence of prions within the sample. By administering the pharmacophores, the time needed to develop symptoms of prion disease will be greatly reduced provided the sample used for inoculation actually does contain $PrP^{Sc}$ (i.e., contains prions). Perhaps most importantly, the pharmacophores can be designed to bind tightly to the $PrP^C$ epitope so that they are not released from the epitope and do not result in the conversion of $PrP^C$ to $PrP^{Sc}$ and such pharmacophores would be valuable therapeutics for the treatment of prion disease.

PPMF is useful in enhancing the speed and sensitivity of an assay which uses a transgenic animal to detect the presence of $PrP^{Sc}$ (i.e., detect prions) in a sample. Specifically, PPMF is administered to transgenic animals which have been inoculated with a sample which may contain prions. The transgenic animals are genetically designed so that they are susceptible to infection by prions which would normally only infect a genetically diverse species. The animals are observed to determine if they develop symptoms of prion infection which if observed allows the tester to deduce that the sample includes prions. The administration of PPMF enhances the rate of disease development thereby shortening assay time.

Assays

Assays for detecting the presence of $PrP^{Sc}$ in a sample can be facilitated by the use of PPMF, pharmacophores thereof and/or antibodies which bind to $PrP^C$ at its $PrP^C$/PPMF binding site. The sample suspected of containing $PrP^{Sc}$ is obtained and prepared as needed. Then $PrP^C$ and PPMF are added which will facilitate the formation of $PrP^C$/PPMF/$PrP^{Sc}$ complexes if $PrP^{Sc}$ is present in the sample. Once the complex is formed the $PrP^C$ is converted to $PrP^{Sc}$ and the complex breaks up allowing the formation of two more complexes. The reaction proceeds geometrically increasing the number of $PrP^{Sc}$ molecules in the sample i.e., 2, 4, 8, 16, etc., for each $PrP^{Sc}$ molecule present. After the reaction is allowed to sufficiently proceed it can be tested for the presence of $PrP^{Sc}$ using any desired assay such as an assay disclosed in U.S. patent application Ser. No. 08/804,536, filed Feb. 21, 1997, which is incorporated herein by reference.

The assay can be used to test for therapeutics. $PrP^C$ and PPMF are added to a known concentration of $PrP^{Sc}$ and a compound to be tested is added. If the compound prevents the formation of $PrP^{Sc}$ the compound is a potential therapeutic for the treatment of prion diseases. The ability to assay for increasing in the concentration of $PrP^{Sc}$ can be determined using an assay and equation disclosed and described in U.S. patent application Ser. No. 08/804,536, filed Feb. 21, 1997.

Assignment of the Binding Site of PPMF onto the $PrP^C$ Structure by NMR

Based on experiments carried out Mo residues 214 and 218 (corresponding to SHa 215 and 219) were assigned to the NMR structure of recombinant SHa PrP 90–231. These residues form a binding pocket-like structure facing to a plasma membrane to which $PrP^C$ is anchored via GPI anchor (FIG. 7). In this pocket, SHa residues 215 and 219 (214 and 218 in Mo) are located on its surface, whereas SHa residue 217 (216 in Mo) is buried and not exposed as our biochemical data indicated. Interestingly, SHa residues 165–173 (164–173 in Mo) on a loop are also participating in this binding pocket-like formation. Gln/Arg polymorphism at sheep residue 171 (167 Mo) has been reported to determine its susceptibility to sheep natural scrapie as Hu polymorphism at residue 219 (218 in Mo) does. Based on the computer assignment, Lys substitution at Hu residue 219 showed an equivalent effect to Gln to Arg substitution at sheep residue 171 on this pocket formation.

PPMF is further characterized by the information provided in Table 1 below.

TABLE 1

| $PrP^C$ | $PrP^{Sc}$ formation | MHM2 $PrP^{Sc}$ formation when co-transfected | Binding affinity to PPMF |
| --- | --- | --- | --- |
| SHa | ↓↓ | ↓↓ | → |
| MH3 | ↓↓ | ↓↓ | → |
| MH2M | ↓ | ↓ | → |
| MHM2 | → | → | → |
| Mo | → | → | → |
| MH3HuA | (—) | → | (—) |
| MH2HuA | (—) | → | (—) |
| MHMHuA | (—) | → | (—) |
| M3HuA | (—) | → | (—) |
| MHMHuA3 | ↓↓ | → | ↓↓ |
| MHMK218 | (—) | ↓↓ | ↑ |
| MHM1218 | ↓ | → | ↓ |
| MHMA218 | ↓↓ | ↓↓ | ↑ |
| MHMW218 | ↓ | ↓↓ | ↑ |
| MHMP218 | (—) | → ~ ↓ | → ~ ↑ |
| MHMR216 | (—) | ↓↓ | → |
| MHMHuR216 | (—) | → | ↓↓ |
| MHMHuA1 | ↓ | ↓↓ | ↑ |
| MHMK214 | (—) | → | (—) |
| MHME214 | (—) | ↓↓ | ↑ |
| MHMA214 | → | → | → |
| MHMW214 | (—) | ↓↓ | ↑ |
| MHMP214 | (—) | → | (—) |

The data presented here in combination with the previous notions obtained by Tg studies allows the following conclusions regarding $PrP^{Sc}$ formation. Mo $PrP^C$ does not inhibit the MHM2 $PrP^{Sc}$ formation when co-transfected because PPMF can be released from the Mo $PrP^C$ after the $PrP^C$ is converted into $PrP^{Sc}$. PPMF is not able to bind to PrP$^{Sc}$ efficiently. In contrast, SHa or MH3 PrP$^C$ remain in the PrP$^C$ isoform and capture PPMF in PrP$^C$/PrP$^{Sc}$ complexes. This results in the depletion of uncomplexed PPMF. In the case of HuA derivatives, PPMF remains free and unbound since the unconverted PrP$^C$/PrP$^{Sc}$ complexes have no binding site for PPMF regardless of the compatibility at its central region. This shows that PPMF is a less abundant protein and is a rate-limiting substrate if not recycled. This shows that the levels of PPMF must be <50% of the levels of endogenous PrP$^C$ to convert PrP$^C$ to PrP$^{Sc}$ and result in disease. Overexpression of SHa or Mo PrP$^C$ increased the rate of PrP$^{Sc}$ formation indicating that PPMF is not rate-limiting and is recycled.

A Hu polymorphism at residue 219 (corresponding to Mo 218) has been reported in the Japanese population. About 12% of the people have the Lys allele instead of the Glu/Glu allele, but so far none of autopsy-proven Japanese patients with CJD possessed the Lys allele at Hu residue 219. The absence of Lys 219 allele in Japanese patients with CJD is due to an aberrant binding affinity of the PrP$^C$ to PPMF. Even if PrP$^C$ carrying Lys allele is unable to convert into PrP$^{Sc}$, one might think that the counterpart of wt-PrP$^C$ could be a substrate to convert into PrP$^{Sc}$, which means allele frequency must be half (6%) in the Japanese CJD population. However, the Examples provided here also revealed that the Lys allele exhibited even tighter binding to PPMF so that the free uncomplexed PPMF is depleted. This explains why the counterpart of wt-PrP$^C$ does not convert into PrP$^{Sc}$. Another sheep Gln/Arg polymorphism at sheep residue 171 also determines its susceptibility to sheep natural scrapie. Knowing that this site is also participating in the binding pocket-like formation as shown in the NMR structure shows that susceptibility to the sheep natural scrapie is governed by PrP$^C$-PPMF interaction at the residue.

One urgent application from the current findings is for the therapeutic approach in prion disease. PPMF is present in such small amounts (<50% of endogenous PrP$^C$) that it is a rate-limiting factor in the formation of PrP$^{Sc}$ if not recycled. Modifying the PPMF binding site in PrP$^C$ efficiently blocks conversion of its own or co-expressed wt-PrP$^C$ into PrP$^{Sc}$. Thus, it is clear the binding site for PPMF primarily governs the inhibition in PrP$^{Sc}$ formation over a segment of PrP$^C$ including the central region between residues to 96–167 mouse PrP$^C$. Molecules which tightly bind PPMF have therapeutic applications in the treatment of prion disease. Further, both human and sheep polymorphisms at the binding pocket for PPMF regulate susceptibility to prion disease.

Corresponding Amino Acid Positions

Mammals possess a PrP gene which expresses a PrP protein in the "cellular" form, i.e., PrP$^C$. With respect to some mammals such as mice and hamsters, the PrP gene and resulting PrP protein are genetically similar. However, with respect to other species such as mice and humans, the PrP gene is genetically diverse.

When a normal animal is inoculated with prions taken from the same or a genetically similar species, the animal will become sick with prion disease. However, when an animal is inoculated with prions from a genetically diverse species the animal does not become sick with prions. This species barrier relates to the species specificity of PPMF and the binding epitope on PrP$^C$. Although much of the information provided here such as that shown within FIGS. 7 and 9 is specific to hamster PrP$^C$ the information is generally applicable to other species by utilizing the information provided below in Table 2 which shows the corresponding amino acid positions for the four critical residues for human, mice, hamster, cow, sheep and the chimeric human mouse PrP gene. Corresponding positions are shown in FIG. 15 along with their relative positions on the PrP protein structure.

TABLE 2

MUTATIONS IN EPITOPE TAGGED MHM2 PrP INHIBIT PrP$^{Sc}$ FORMATION IN SCN2A CELLS

| Mo Codon Number | PrP Residue: Mouse | Human | Syr Hamster | Sheep | Mutant MHM2 | Type of inhibition of PrP$^{Sc}$ Formation |
|---|---|---|---|---|---|---|
| 167 | Q | E | Q | Q/R | | |
| 170 | N | | | | S | None |
| 171 | Q | Q | Q | Q | R | 2 |
| 214 | V | I | T | I | I | 2 |
| | | | | | K | 1 |
| | | | | | E | 2 |
| | | | | | A | 1 |
| | | | | | W | 2 |
| | | | | | P | 1 |
| 215 | T | T | T | T | Q | None |
| 216 | Q | Q | Q | Q | R | 2 |
| 218 | Q | E/K | Q | Q | E | 1 |
| | | | | | K | 2 |
| | | | | | I | 1 |
| | | | | | A | 2 |
| | | | | | W | 2 |
| | | | | | P | 1 |
| | | | | | F | 1 |
| | | | | | R | 2 |
| | | | | | H | 2 |
| 219 | K | R | K | R | R | None |
| 221 | S | S | S | S | A | None |
| 222 | Q | Q | Q | Q | K | None |

MECHANISMS OF INHIBITION OF PrP$^{Sc}$ FORMATION

| Type of Inhibition | Example | Putative Mechanism | Relative affinity for protein X* |
|---|---|---|---|
| 1 | HuPrP$^C$ (E219) binding to Mo protein X inhibited by MoPrP$^C$ | Competitive | Low |
| 2 | HuPrP$^C$ (K219) prevents MoPrP$^C$ binding to protein X | Non-competitive | High |
| 3 | SHaPrP$^C$ binds to protein X and is not released by MoPrP$^{Sc}$ | Non-competitive | Similar |

*affinity relative to that of MoPrP$^C$ for Mo protein X.

Prion Resistant Animals

Animals resistant to prion disease could be created by (1) ablating the PrP gene; (2) making substitutions in the PrP gene at critical points within the PrP/PPMF binding site or (3) examining the PrP gene of animals and breeding those animals which are found to include codons which encode amino acids at the PrP epitope site which would render the animal resistant to prion disease.

Although ablating the PrP gene might be the simplest route to obtain a prion resistant animal, such has been accomplished only in mice—although others have suggested that the PrP gene could be ablated in other animals (see PCT publication WO93/10227 published May 27, 1993).

FIGS. 3, 4 and 5 show that the sequence of the PrP gene is known for a number of different mammals. PrP genes have been extracted and isolated. Using the site directed recombination (homologous recombination methods), the codons at particular positions can be replaced to create artificial genes of the invention which genes, when operably inserted in the genome of an animal, render the animal resistant to prion infection. Using the information within Table 2 and FIGS. 7 and 15, it is possible to carry out codon substitutions at all or any of the four sites within the PrP epitope which would affect binding of the PrP protein to PPMF. The effect of a number of substitutions are shown in Table 2. After creating the desired recombinant PrP gene, the gene could be injected into a fertilized egg and implanted in a pseudo-pregnant female and allowed to grow to term. If the implanted recombinant PrP gene replaced the native PrP gene, a transgenic animal results which animals is resistant to prion disease.

There are a number of mutations and polymorphisms existing with respect to the PrP gene of a different species. A number of the mutations and polymorphisms are listed in the "Mutation Table" provided below. It is believed that additional mutations and polymorphisms exist in all species within the PrP gene. However, until now one could not determine which sequences might provide for resistance to prion disease. However, by using the information within FIG. 15 along with the information known with respect to PrP gene sequences, it is possible to screen animals with respect to the sequence of their PrP gene. The screening is carried out in order to determine mutations existing at the sites which match the critical sites indicated in FIG. 15 and/or other sites which form part of the $PrP^C$ binding epitope, i.e., the epitope on $PrP^C$ which binds to PPMF. Animals with a PrP gene which is heterozygous at a particular point could be bred with other animals which are heterozygous at that point in order to produce offspring which include those with a homozygous PrP gene of the type desired.

Whether screening or breeding animals or producing recombinant PrP genes, certain factors should be considered. Specifically, it is most desirable to breed for an animal or produce a PrP gene wherein more than 1 of the critical sites as per FIG. 15 is substituted with a new codon which will produce a new amino acid. Secondly, the substitution at the critical site should be with an amino acid which is biochemically quite different from the amino acid at that position which is known to render the animal susceptible to prion infection. Thus, if a basic and/or polar amino acid is present at the critical site that site could be replaced with an acidic and/or nonpolar amino acid. With these criteria in mind some trial and error would be required. However, by knowing the critical positions per Table 2 and FIGS. 7 and 15 and knowing that substitutions should be made to make the amino acid different, the desired results can be obtained. Acidic amino acids should be substituted with basic amino acids and vice versa. Polar amino acids should be substituted with nonpolar amino acids and vice versa.

Prion Protein Modulator Factor (PPMF)

Based on experiments and results described here and deductions made therefrom, the protein PPMF is characterized as follows:
(a) binds to $PrP^C$ and facilitates a conformational change from $PrP^C$ to $PrP^{Sc}$;
(b) the binding is species specific, i.e. PPMF of a given species binds to $PrP^C$ of that species only on a species which is genetically similar in terms of its $PrP^C$ proteins;
(c) does not bind to $PrP^{Sc}$ and as such is released from a $PrP^C$ molecule after it is converted to $PrP^{Sc}$;
(d) acts as a rate limiting component in the conversion of $PrP^C$ to $PrP^{Sc}$;
(e) binding of PPMF to $PrP^C$ is not effected by residues 216, 220, 221 and 222 in human $PrP^C$ protein and the corresponding residues in other species;
(f) PPMF allows for the formation of a $PrP^C/PrP^{Sc}$ complex where the PPMF holds the complex together until $PrP^C$ is converted to $PrP^{Sc}$;
(g) PPMF is released from the $PrP^C/PrP^{Sc}$ complex once $PrP^C$ is converted to $PrP^{Sc}$ as PPMF does not bind to $PrP^{Sc}$;
(h) PPMF decreases the activation energy barrier between $PrP^C$ and $PrP^{Sc}$;
(i) binding of PPMF to $PrP^C$ is effected by residues at position 215 and 219 in hamster $PrP^C$ and corresponding positions in the $PrP^C$ protein of other species;
(j) binding of PPMF to $PrP^C$ is effected by a residue at position 172 in SHa $PrP^C$. and a corresponding position in a different species;
(k) PPMF binds to a discontinuous epitope on $PrP^C$ which epitope comprises residues 172, 215, 219 in human $PrP^C$ and the residues at corresponding positions at the $PrP^C$ protein of other species;
(l) preferred forms of PPMF are encoded by a nucleotide sequence of a species selected from the group consisting of human, cow, sheep, mouse and hamster.

Pharmacophores

The shape that $PrP^C$ adopts at its binding epitope when bound to the biologically active target molecule PPMF, the biological SHape, is an essential component of its biological activity. This shape, and any specific interactions such as hydrogen bonds, can be exploited to derive predictive models used in rational drug design. These can be used to optimize lead compounds, designed de novo compounds, and search databases of existing compounds for novel structures possessing the desired biological activity. In order to aid in the discovery of useful pharmacophores for the $PrP^C$ binding epitope, these models must make useful predictions, relate chemical structures to activity, and confidently extrapolated to chemical classes beyond those used for model derivation.

Pharmacophore models (e.g., BioCAD incorporated herein by reference) model activity in terms of the positions of a small number of atoms of particular functional groups. This overcomes many of the problems of traditional QSAR models. U.S. Pat. No. 5,025,388 to Kramer et al. provides for comparative molecular field analysis (COMFA incorporated herein by reference) methodology. In accordance with this methodology the 3-dimensional structure for each molecule is placed within a 3-dimensional lattice and a probe atom is chosen, placed successively at each lattice intersection and the stearic and electrostatic interaction energies between the probe atom and the molecule are calculated for all lattice intersections. The energies are listed in a 3-dimensional-QSAR table. A field fit procedure is applied by choosing the molecule with the greatest biological activity as the reference in conforming the remaining molecules to it.

The methodology disclosed within U.S. Pat. No. 5,526, 281 (incorporated herein by reference in its entirety) is particularly useful for the generation of pharmacophores using the information provided herein and in particular the 3-dimensional coordinates shown within FIG. 9 which can be applied to the $PrP^C$ protein of other molecules using the information of FIG. 15. This methodology is particularly useful for the generation of pharmacophores of the present invention because in many binding interactions between molecules, not all the characteristics of the molecule considered are of equal importance. As shown within FIG. 7, many of the amino acids within the PrP$^C$ protein are of little importance with respect to the surface of the binding epitope presented for binding PPMF. The approach disclosed within Pat. No. 5,526,281 allows the user to focus on the salient features of the molecule.

The first step in the '281 method for generating pharmacophores involves the selection of a pose. A pose of a molecule is defined by its confirmation (internal torsional angles of the rotatable bonds) and orientation (the rigid rotations and translations). This mathematically defines the pose of a molecule and in connection with the present invention is shown within FIG. 9. FIG. 9 shows the coordinates for a pose for the binding epitope of PrP$^C$. The negative image of the coordinates as shown in FIG. 9 can also be generated and as such represents a pose for the binding epitope of PPMF. The negative image and other possible pharmacophores can be generated using software available such as Catalyst™ from BioCad, Foster City, Calif. and, Batchmin™ available from Columbia University, New York City, N.Y. (both of which are incorporated herein by reference). These programs take into consideration various properties including physical and chemical properties, SHape, electrostatic interaction, salvation and biophysical properties.

Other methods for generating pharmacophores of the present invention are disclosed within U.S. Pat. No. 5,307,287 issued Apr. 26, 1994 and U.S. Pat. No. 5,434,796 issued Jul. 18, 1995 (both of which are incorporated herein by reference in their entirety). Comparative molecular field analysis (COMFA) is an effective computer implemented methodology of 3D-QSAR employing both interactive graphics and statistical techniques for co-relating shapes of molecules with their observed biological properties. For each molecule in a series of known substrates the stearic and electrostatic interaction energies with a probe atom are calculated at spacial coordinates around the molecule. Subsequent analysis of the data table by a partial list square (PLS) cross-validation technique yields a set a coefficients which reflect the relative contribution of the SHape elements of the molecular series to differences in biological activities. Display in three dimensions in an interactive graphics environment of the spacial volumes highly associated with biological activity, and comparison with molecular structures yields an understanding of intermolecular associations. CoMFA will also predict the biological activity of new molecular species such as various pharmacophores of either the PrP$^C$ binding epitope or the surface to which it binds on PPMF.

Test Animal

Although a variety of different test animals could be used for testing for the presence of prions within a sample, preferred host animals are mice and hamsters, with mice being most preferred in that there exists considerable knowledge on the production of transgenic animals. Other possible host animals include those belonging to a genus selected from Mus (e.g. mice), Rattus (e.g. rats), Oryctolagus (e.g. rabbits), and Mesocricetus (e.g. hamsters) and Cavia (e.g., guinea pigs). In general mammals with a normal full grown adult body weight of less than 1 kg which are easy to breed and maintain can be used. The host PrP gene can be changed to include codons from genetically diverse PrP genes from test animals belonging to a genus selected from Bos, Ovis, Sus and Homo. Preferably, a mouse host PrP gene is changed to include codons from a human, cow or sheep PrP gene, with human being most preferred. Humans are preferred because an important object of the invention is to use the animal to test a sample of material to determine if that material has prions which will infect a human and cause a human to develop a CNS disease such as CJD. Preferred transgenic animals are disclosed in U.S. Pat. No. 5,565,186 issued Oct. 15, 1996 and WO 97/04814 published Feb. 13, 1997 which are incorporated herein by reference to disclose transgenic animals and methods of making and using such.

The genetic material which makes up the PrP gene is known for a number of different species of animals (see Gabriel et al., Proc. Natl. Acad. Sci. USA 89:9097–9101 (1992)). Further, there is considerable homology between the PrP genes in different mammals. For example, see the amino acid sequence of mouse PrP compared to human, cow and sheep PrP in FIGS. 3, 4 and 5 wherein only the differences are shown. Further, note that the segment of a PrP gene used to create the MHu2M gene of the present invention will result in encoding of protein which shows a difference between the human and a mouse protein of only nine residues. Although there is considerable genetic homology with respect to PrP genes, the differences are significant in some instances. More specifically, due to small differences in the protein encoded by the PrP gene of different mammals, a prion which will infect one mammal (e.g. a human) will not normally infect a different mammal (e.g. a mouse). Due to this "species barrier," it is not generally possible to use normal animals, (i.e., animal which have not had their genetic material related to prions manipulated) such as mice to determine whether a particular sample contains prions which would normally infect a different species of animal such as a human. The present invention solves this problem in a surprising manner.

Relationships—PrP Genes:Copy Numbers:Genetic Diversity

Commercially useful transgenic animals are referably small and easy to reproduce; thus, host animals such as mice, hamsters, guinea pigs and rats are referred, with mice being most preferred. In order for the transgenic animals to be useful, it is necessary for the animals to be susceptible to infection with prions which normally infect only genetically diverse test animals, and in particular animals of commercial significance for testing, such as humans, cows, horses, sheep, pigs, cats, dogs and chickens, with humans being most preferred. Further, for the transgenic and hybrid animals to be useful in a practical and commercial sense, it is necessary for the animals to demonstrate symptoms of the disease within a relatively short period after inoculation, and for a very high percentage of the animals to demonstrate symptoms of the disease after inoculation. Both criteria are facilitated by the administration of PPMF.

In producing a transgenic animal having the above-described characteristics, we noted a number of relationships of significance.

First, when the entire PrP gene of a test animal (such as a human) is made functional in the host animal (such as a mouse) the resulting transgenic animal (with a low copy number of human PrP genes) is not susceptible to infection with human prions.

Second, we found that infection would occur if the endogenous PrP gene of the host animal is ablated.

Third, when only some of the codons differing between the host and the test animal are switched, the resulting transgenic animal is susceptible to infection with prions which normally only infect the test animal.

Fourth, we noticed that, as the copy number of the artificial gene in the transgenic animal is increased, the incubation time in some cases decreases.

Fifth, we noted that humans with some genetic defects resulting in prion diseases have different genetic defects in their PrP gene and that by matching the defects in any transgenic animal will render that animal more susceptible to infection with prions from the diseased human.

With this knowledge, we deduced that it is possible to produce a transgenic animal wherein all of the PrP gene of the host animal is replaced with the PrP gene of a test animal to obtain a useful transgenic animal which is susceptible to infection with prions which normally only infect the test animal by either (1) administering PPMF and/or (2) substantially increasing the copy number of the test animal's PrP gene in the host animal and preferably also ablating the endogenous PrP gene.

For example, a transgenic mouse which includes the entire PrP gene of a human in a relatively low copy number (e.g. 1 to 4) is not susceptible to infection with human prions (unless the endogenous mouse PrP gene is ablated). However, if the transgenic mouse includes a very high copy number of a human gene (e.g. 30–300 copies), the resulting transgenic animal is susceptible to infection with human prions. Further, when a host animal such as a mouse has only a portion of its PrP gene replaced with a corresponding portion of a test animal such as a human, the resulting transgenic animal is highly susceptible to infection with prions which normally infect only the test animal. This is true even if the chimeric gene is present in the transgenic animal in a relatively low copy number (e.g. 1 to 4 copies) resulting in low expression of MHu2M $PrP^C$.

Lastly, in order to reduce incubation time hybrid mice were created by crossing mice with ablated PrP genes with transgenic mice which (1) included a PrP gene from a genetically diverse animal e.g., a human or (2) include a chimeric or artificial gene of the present invention. The chimeric gene and/or PrP gene from genetically diverse test animal may be present in high copy number. The copy number can be increased in order to reduce incubation time provided the copy number is not increased so far that the animal becomes spontaneously ill, i.e., become ill without inoculation with prions.

Based on the above, it can be understood that the preferred transgenic animals are (1) animals such as mice which include a chimeric PrP gene, i.e., only a portion, but not all, of their PrP gene replaced with a corresponding portion of the PrP gene of a test animal or (2) animals with an ablated endogenous PrP gene and a PrP gene from another animal such as a human most preferable where that human PrP gene has a genetic defect which results in a prion disease when in a human.

Species Barrier Broken

The transmission of human CJD to apes and monkeys 1.5–3 years after intracerebral inoculation provided considerable interest in the causes of neurodegenerative diseases [Gibbs, Jr. et al., Science 161:388–389 (1968)]. Humans are not genetically diverse from apes and monkeys which accounts for the cross-species infectivity, although with a long incubation time. While the high cost of caring for nonhuman primates prevented extensive studies of the human prion diseases, the transmissibility of these diseases stimulated studies of the animal prion analogues in rodents [Manuelidis et al., Proc. Natl. Acad. Sci. USA 75:3422–3436 (1978); Manuelidis et al., Proc. Natl. Acad. Sci. USA 73:223–227 (1976); Tateishi et al., Ann. Neurol. 5:581–584 (1979)].

The present disclosure of PPMF allows assays to be performed relatively rapidly in genetically altered mammals such as Tg(MHu2M) mice that are relatively inexpensive to maintain. Endpoint titrations of prions in multiple human body tissues and fluids can be performed and standard curves constructed for more economical incubation time assays. The information derived from such studies of human prions will be useful in the management of CJD patients who are thought to pose some risk to relatives, physicians, nurses and clinical laboratory technicians [Berger et al., Neurology 43:205–206 (1993); Ridley et al., Lancet 341:641–642 (1993)].

In studies of human prion diseases with apes and monkeys, the use of one or two, or rarely three, animals as recipients for a single inoculum has presented a significant problem in evaluating the transmissibility of a particular inoculum from an individual patient. The transgenic mice contain a chimeric prion protein gene, e.g., Tg(MHu2M) mice, and hybrid mice e.g., Tg(HuPrP)/Prnp$^{0/0}$ described here obviate many of the problems created by using nonhuman primates.

These results demonstrate the "universality" of the MHu2M transgene for transmission studies with other types of transgenic animals and other prion inocula. For example, it may be most efficient to use mice expressing MHu2MPrP transgenes coding for either a methionine or valine at codon 129, and by doing so, match the genotype of the Tg mouse (with respect to codon 129) with the genotype of the individual from which the inoculum is derived. Homozygosity at the codon 129 polymorphism has a profound influence on the incidence of sporadic CJD [Palmer et al., Nature 352:340–342 (1991)]. The MHu2MPrP transgene encodes a Met at codon 129 and the iatrogenic CJD case was homozygous for Met [Collinge et al., Lancet 337:1441–1442 (1991)].

A human PrP gene is polymorphic at codon 129. More specifically, normal human PrP gene can be either homozygous Met/Met or Val/Val or heterozygous Met/Val at codon 129. The codon 129 polymorphism influences the susceptibility of humans to prion disease and specifically to iatrogenic and sporadic CJD. This polymorphic codon is contained in the central region of MHu2MPrP which is derived from human PrP. The DNA sequence used to generate Tg(MHu2M) mice encodes Met at codon 129. The transgenic mice expressing MHu2MPrP with valine at codon 129 can be produced using similar procedures.

To break the species barrier an artificial PrP gene was inserted into a host mammal (such as a mouse) renders that mammal susceptible to infection with prions which normally infect only a genetically diverse test mammal (e.g. a human, cow or sheep). The artificial PrP gene may include the natural PrP gene sequence of the host animal with one or more (preferably less than 40) codon sequences being replaced with other codon sequences such as corresponding codons of a genetically diverse mammal (e.g. a human, cow or sheep).

Figure 1:
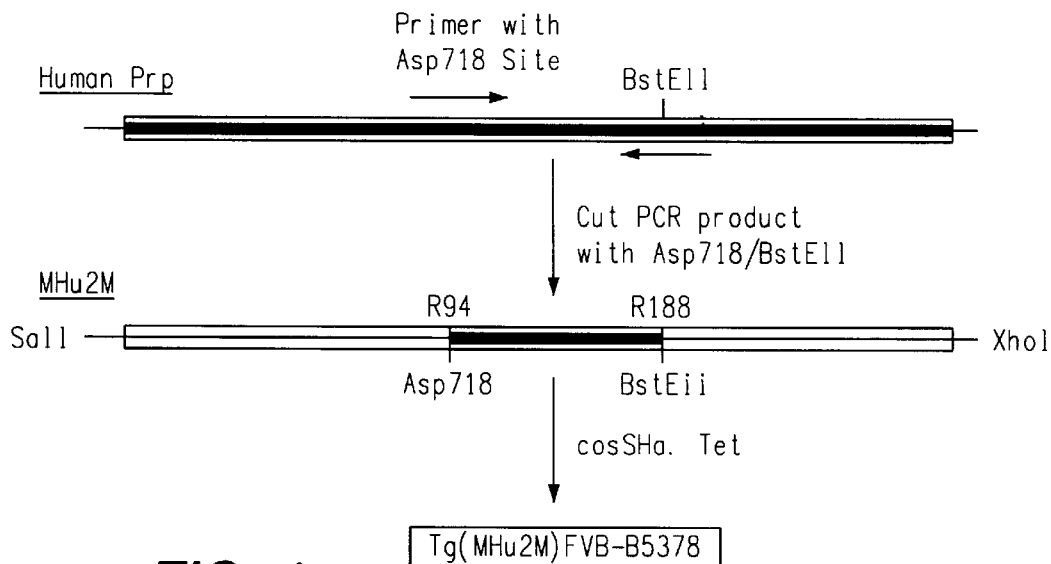
FIG. 1 is a schematic drawing showing the construction of a chimeric MHu2M gene and a transgenic mouse containing same.

The species barrier is broken by inserting into a mammal (a mouse) the chimeric gene (MHu2M) which is shown being assembled schematically in FIG. 1. In order to produce the chimeric gene, it is first necessary to obtain nucleotide sequences which encode human PrP. The human PrP genes are then subjected to the conventional PCR procedures in order to produce large numbers of copies of the gene or portions of the gene. The PCR product is then isolated, specific restriction sites are added and the copied product is subjected to specific endonucleases in order to remove a middle section of the human PrP gene. Specifically, restriction sites are added such that when the PCR product is subjected to endonucleases such as Asp718 as well as BstEII, a section of the gene is cut out. The use of these two endonucleases will remove a center portion of the human PrP gene (codons 94–188) which portion encodes amino acid residues 94 through 188. Endonucleases are also used to remove a corresponding center portion of the mouse PrP gene. The removed center portion of the mouse gene is then discarded and the center portion obtained from the human PrP gene is fused into the mouse gene to produce a chimeric human/mouse gene. Details of how the specific MHu2M gene was produced are described in Example 1 and shown in FIG. 1.

Figure 2:
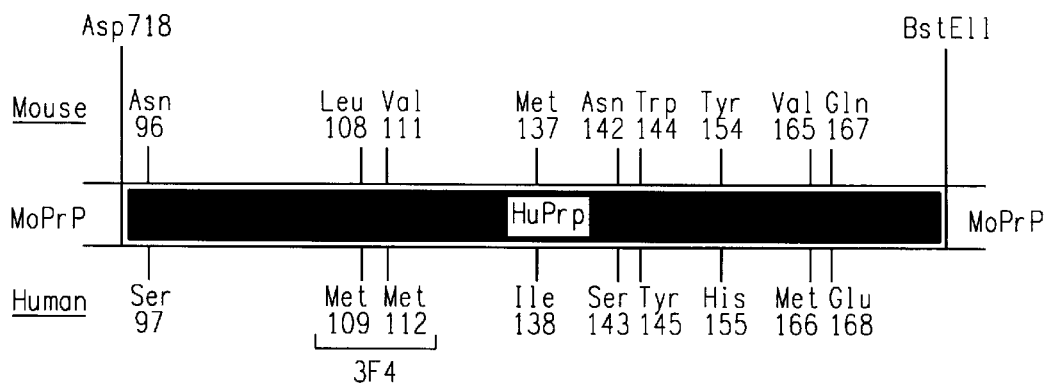
FIG. 2 is a schematic view of a portion of PrP proteins showing the differences between a normal, wild-type human PrP protein and a normal, wild-type mouse PrP protein.

As shown with FIG. 2, there is a high degree of homology between the removed center portion of the human PrP gene and the segment of the mouse PrP gene which is replaced. Specifically, the segments differ at nine codons. Thus, when the genetic material is expressed, the resulting chimeric MHu2M protein will differ from MoPrP at 9 residues. These residues and their positions are shown in FIG. 2. After the chimeric gene is produced, it can be microinjected into a mouse egg using known technology as described within Scott et al., *Cell* 59:847–857 (1989) and Scott et al., *Protein Sci.* 1:986–997 (1992) and see also WO91/19810 published Dec. 22, 1991 as well as other publications relating to the production of transgenic mice cited therein and known to those skilled in the art. The injected mouse egg is then implanted into a mouse using known procedures. Multiple eggs can be implanted into a single mouse and known procedures can be used to determine whether the resulting offspring are transgenic mice which include the chimeric gene within their genome. Details of this procedure are described in Examples 6 and 7.

The "species barrier" is broken by producing a chimeric PrP gene wherein a middle portion of the mouse PrP gene is replaced with a corresponding middle portion of a human PrP gene thereby leaving the C- and N-terminus of the mouse PrP gene intact. However, other segments of the mouse PrP gene can be replaced with other homologous segments of the human PrP gene and obtain a transgenic mouse which is subject to being readily infected with human prions.

Pathogenic Mutations and Polymorphisms

There are a number of known pathogenic mutations in the human PrP gene. Further, there are known polymorphisms in the human, sheep and bovine PrP genes. The following is a list of such mutations and polymorphisms:

MUTATION TABLE

| Pathogenic human mutations | Human Polymorphisms | Sheep Polymorphisms | Bovine Polymorphisms |
|---|---|---|---|
| 2 octarepeat insert | Codon 129 Met/Val | Codon 171 Arg/Gln | 5 or 6 octarepeats |
| 4 octarepeat insert | Codon 219 Glu/Lys | Codon 136 Ala/Val | |
| 5 octarepeat insert | | | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

In order to provide further meaning to the above chart demonstrating the mutations and polymorphisms, one can refer to the published sequences of PrP genes. For example, a chicken, bovine, sheep, rat and mouse PrP gene are disclosed and published within Gabriel et al., *Proc. Natl. Acad. Sci. USA* 89:9097–9101 (1992). The sequence for the Syrian hamster is published in Basler et al., *Cell* 46:417–428 (1986). The PrP gene of sheep is published by Goldmann et al., *Proc. Natl. Acad. Sci. USA* 87:2476–2480 (1990). The PrP gene sequence for bovine is published in Goldmann et al., *J. Gen. Virol.* 72:201–204 (1991). The sequence for chicken PrP gene is published in Harris et al., *Proc. Natl. Acad. Sci. USA* 88:7664–7668 (1991). The PrP gene sequence for mink is published in Kretzschmar et al., *J. Gen. Virol.* 73:2757–2761 (1992). The human PrP gene sequence is published in Kretzschmar et al., *DNA* 5:315–324 (1986). The PrP gene sequence for mouse is published in Locht et al., *Proc. Natl. Acad. Sci. USA* 83:6372–6376 (1986). The PrP gene sequence for sheep is published in Westaway et al., *Genes Dev.* 8:959–969 (1994). These publications are all incorporated herein by reference to disclose and describe the PrP gene and PrP amino acid sequences.

Differences in the Conversion of MHu2MPrP$^C$ and HuPrP$^C$ into the Scrapie Isoform in Mice The fundamental event in prion propagation is the conversion of PrP$^C$, which contains ~43% α-helix and is devoid of β-sheet, into PrP$^{Sc}$ which has ~44% β-sheet [Pan et al., *Proc. Natl. Acad. Sci. USA* 90:10962–10966 (1993)]. From the results of Tg(SHaPrP) mouse studies, this process is thought to involve the formation of a complex between PrP$^{Sc}$ and the homotypic substrate PrP$^C$ [Prusiner et al., *Cell* 63:673–686 (1990)]. Attempts to mix PrP$^{Sc}$ with PrP$^C$ have failed to produce nascent PrP$^{Sc}$ [Raeber et al., *J. Virol.* 66:6155–6163 (1992)], this shows that PPMF is catalyzing the conformational changes that feature in the formation of PrP$^{Sc}$. The difference in susceptibility of Tg(MHu2M) and Tg(HuPrP) mice to Hu prions in mice is due to the fact that mouse PPMF catalyzing the refolding of PrP$^C$ into PrP$^{Sc}$ can recognize MHu2MPrP much more readily than HuPrP.

Standardized Prion Preparation

Standardized prion preparations are produced for use in assays so as to improve the reliability of the assay. Although the preparation can be obtained from any animal it is preferably obtained from a host animal which has brain material containing prions of a test animal. For example, a Tg mouse containing a human prion protein gene can produce human prions and the brain of such a mouse can be used to create a standardized human prion preparation. The preparation can be further standardized by repeating the above process. More specifically, per the above process some prion containing material must be used to inoculate the transgenic mice. The source of that prion containing material may itself be unpredictable and result in infecting transgenic mice in different ways. Thus, if the transgenic mice are infected with a nonstandard material some may develop the symptoms of prion disease at different rates and some may not develop symptoms at all. If a group of mice which develops symptoms of prion disease at the same time are sacrificed and their brains extracted and homogenized such will create a relatively standard prion preparation. This preparation can then be used to inoculate a new group of transgenic animals. This process can be repeated a number of times e.g., 1 to 10 times or until such point as all of the transgenic mice are developing symptoms of prion disease at approximately the same point in time after inoculation with the standardized preparation. Further details of how to produce a standardized preparation are provided below and in Example 8.

In that the preparation is to be a "standard" it is preferably obtained from a battery (e.g., 100; 1,000, or more animals) of substantial identical animals. For example, 100 mice all containing a very high copy number of human PrP genes (all polymorphisms and mutations) would spontaneously develop disease and the brain tissue from each could be combined to make a useful standardized prion preparation.

Standardized prion preparations can be produced using any of the modified host mammals of the present invention. For example, standardized prion preparations could be produced using mice, rats, hamsters, or guinea pigs which are genetically modified per the present invention so that they are susceptible to infection with prions which prions would generally only infect genetically diverse species such as a human, cow, sheep or horse and which modified host mammals will develop clinical signs of CNS dysfunction within a period of time of 350 days or less after inoculation with prions. The most preferred host mammal is a mouse in part because they are inexpensive to use and because a greater amount of experience has been obtained with respect to production of transgenic mice than with respect to the production of other types of host animals.

Once an appropriate type of host is chosen, such as a mouse, the next step is to choose the appropriate type of genetic manipulation to be utilized to produce a standardized prion formulation. For example, the mice may be mice which are genetically modified by the insertion of a chimeric gene of the invention. Within this group the mice might be modified by including high copy numbers of the chimeric gene and/or by the inclusion of multiple promoters in order to increase the level of expression of the chimeric gene. Alternatively, hybrid mice of the invention could be used wherein mice which have the endogenous PrP gene ablated are crossed with mice which have a human PrP gene inserted into their genome. There are, of course, various subcategories of such hybrid mice. For example, the human PrP gene may be inserted in a high copy number an/or used with multiple promoters to enhance expression. In yet another alternative the mice could be produced by inserting multiple different PrP genes into the genome so as to create mice which are susceptible to infection with a variety of different prions, i.e., which generally infect two or more types of test animals. For example, a mouse could be created which included a chimeric gene including part of the sequence of a human, a separate chimeric gene which included part of the sequence of a cow and still another chimeric gene which included part of the sequence of a sheep. If all three different types of chimeric genes were inserted into the genome of the mouse the mouse would be susceptible to infection with prions which generally only infect a human, cow and sheep.

After choosing the appropriate mammal (e.g., a mouse) and the appropriate mode of genetic modification (e.g., inserting a chimeric PrP gene) the next step is to produce a large number of such mammals which are substantially identical in terms of genetic material related to prions. More specifically, each of the mice produced will include an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time e.g., within ±30 days of each other.

Once a large group e.g., 50 or more, more preferably 100 or more, still more preferably 500 or more of such mice are produced. The next step is to inoculate the mice with prions which generally only infect a genetically diverse mammal e.g., prions from a human, sheep, cow or horse. The amounts given to different groups of mammals could be varied. After inoculating the mammals with the prions the mammals are observed until the mammals exhibit symptoms of prion infection e.g., clinical signs of CNS dysfunction. After exhibiting the symptoms of prion infection the brain or at least a portion of the brain tissue of each of the mammals is extracted. The extracted brain tissue is homogenized which provides the standardized prion preparation.

As an alternative to inoculating the group of transgenic mice with prions from a genetically diverse animal it is possible to produce mice which spontaneously develop prion related diseases. This can be done, for example, by including extremely high copy numbers of a human PrP gene into a mouse genome. When the copy number is raised to, for example, 100 or more copies, the mouse will spontaneously develop clinical signs of CNS dysfunction and have, within its brain tissue, prions which are capable of infecting humans. The brains of these animals or portions of the brain tissue of these animals can be extracted and homogenized to produce a standardized prion preparation.

The standardized prion preparations can be used directly or can be diluted and tittered in a manner so as to provide for a variety of different positive controls. More specifically, various known amounts of such standardized preparation can be used to inoculate a first set of transgenic control mice. A second set of substantially identical mice are inoculated with a material to be tested i.e., a material which may contain prions. A third group of substantially identical mice are not injected with any material. The three groups are then observed. The third group, should, of course not become ill in that the mice are not injected with any material. If such mice do become ill the assay is not accurate probably due to the result of producing mice which spontaneously develop disease. If the first group, injected with a standardized preparation, do not become ill the assay is also inaccurate probably because the mice have not been correctly created so as to become ill when inoculated with prions which generally only infect a genetically diverse mammal. However, if the first group does become ill and the third group does not become ill the assay can be presumed to be accurate. Thus, if the second group does not become ill the test material does not contain prions and if the second group does become ill the test material does contain prions.

Figure 10:
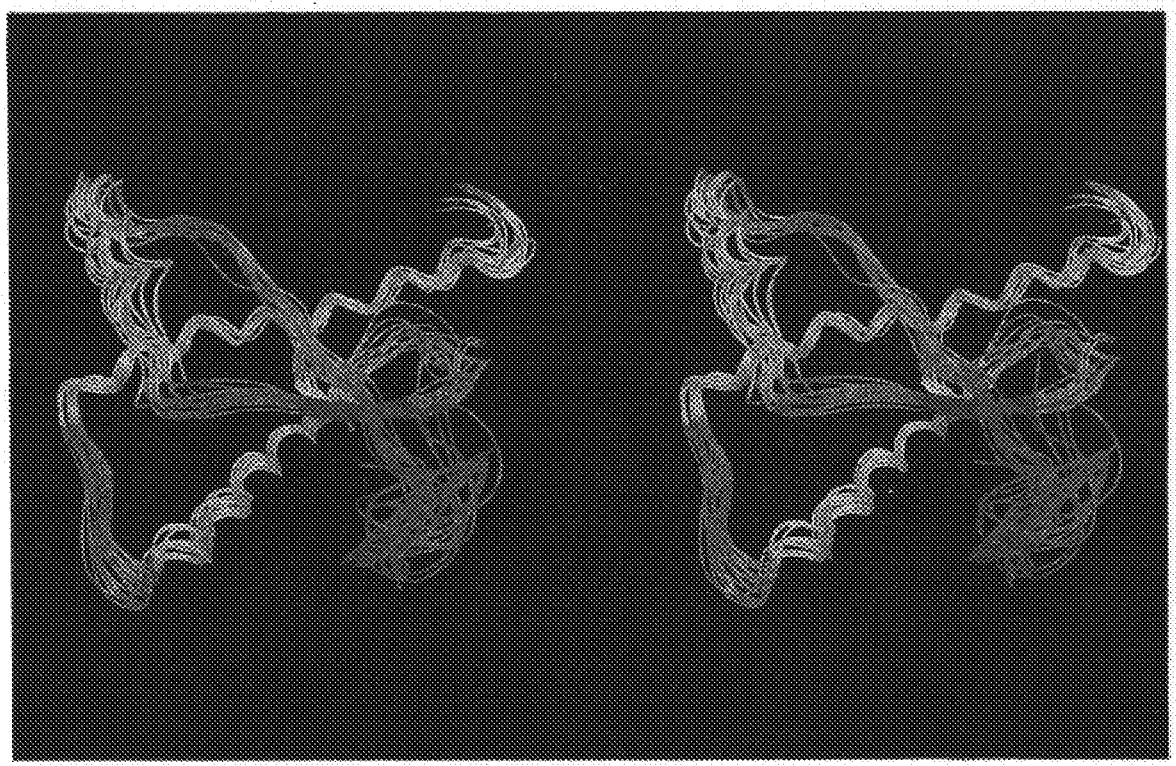
FIG. 10 is a computer generated comparison of the ten best-scoring structures of rPrP shown with a best-fit superposition of backbone atoms for residues 113–227 (stereoview).

By using standardized prion preparations it is possible to create extremely dilute compositions containing the prions. For example, a composition containing one part per million or less or even one part per billion or less can be created. Such a composition can be used to test the sensitivity of the transgenic mice of the invention in detecting the presence of prions in the sample.

Prion preparations are desirable in that they will include a constant amount of prions and are extracted from an isogeneic background. Accordingly, contaminates in the preparations will be constant and controllable. Standardized prion preparations will be useful in the carrying out of bioassays in order to determine the presence, if any, of prions in various pharmaceuticals, whole blood, blood fractions, foods, cosmetics, organs and in particular any material which is derived from an animal (living or dead) such as organs, blood and products thereof derived from living or dead humans. Thus, standardized prion preparations will be valuable in validating purification protocols where preparations are spiked and reductions in teeter measured for a particular process.

Measuring Levels of Prions

PPMF can be administered to transgenic mice to determine the concentration of prions (which generally only infect a genetically diverse animal) within a given sample. The transgenic mice make it possible to test for the positive presence of prions within a sample. The mice are capable of detecting the presence of prions in a concentration as low as 1 ppm or even 1 ppb or less and administering PPMF reduces the time needed for the mice to show signs of disease. The procedure for doing such will be apparent to those skilled in the art upon a review of the present disclosure in combination with an article entitled "Measurement Of The Scrapie Agent Using An Incubation Time Interval Assay," published by Prusiner, et al, *Annals. of Neurology* 11:353–358 (1982) which is incorporated herein by reference to disclose such a method of measurement. See also U.S. Pat. No. 5,565,186, issued Oct. 15, 1996. In general, the method is carried out by determining the titer of the prions by carrying out measurements of time intervals from inoculation to onset of symptoms and from inoculation to death. The intervals are inversely proportioned to the size of the dose injected intracerebrally. The logarithms of the time intervals minus a time factor are linear functions of the logarithms of the inoculum size.

Evidence of Disease $PrP^{Sc}$ has been found in the brains of affected Tg(MHu2M) mice after inoculation with Hu(CJD) or Mo(RML) prions. Brain homogenates of Tg(MHu2M) were either left undigested or digested with proteinase K (BMB) at a final concentration of 20 $\mu$g/ml for 1 hour at 37° C. (even numbered lanes). Samples were resolved by SDSPAGE and then analyzed by Western blot.

The distribution of $PrP^C$ and $PrP^{Sc}$ in clinically sick Tg(MHu2M) mice inoculated with Mo(RML) and Hu(CJD) prions were detected by the histoblot method. The histoblots included those of coronal sections through the region of the hippocampus and thalamus. Differences are observed between: (A) $PrP^C$ in Mo(RML) infected mouse; (B) $PrP^C$ in sporadic CJD RG-infected mouse; (C) $PrP^{Sc}$ in Mo(RML) infected mouse; (D) $PrP^{Sc}$ in sporadic CJD RG-infected mouse; (E) $PrP^{Sc}$ in sporadic CJD EC-infected mouse; and (F) $PrP^{Sc}$ in iatrogenic CJD (#364)-infected mouse.

Structural Analysis of $PrP^C$

To investigate the basis of the PrP structural transitions, recombinant PrP protein, termed rPrP, was prepared using the SHaPrP sequence corresponding to residues 90–231 of PrP 27–30. The rPrP was uniformly labeled with $^{15}N$ or with both $^{13}C$ and $^{15}N$; it was refolded into a conformer that resembles $PrP^C$ based on optical spectroscopic and immunochemical measurements. The pH of the rPrP solution was found to be critical: N-terminal epitopes (residues 90–112) in rPrP were observed to be partially buried at pH 5.2–8.0 by ELISA using N-terminal rFabs. These epitopes became completely exposed at pH 4.8 or lower. Whether this conformational transition, detected by rFabs, modified the NMR structure of MoPrP (121–231) determined at pH 4.5 (3) remains to be established. When rPrP (0.9 mM) was poised in the middle of this structural transition at pH 5.0 in 20 mM acetate and 0.005% Na azide, its $\alpha$-hellical state was stable for at least 15 days at temperatures from 4–30° C. as judged by circular dichroism (CD); however, even one day at 35° C. led to a significant loss of $\alpha$-helix. This apparent acquisition of $\beta$-sheet was concentration-dependent: at 35° C., increasing the concentration from 0.03 mM incrementally to 0.75 mM revealed that increasing the protein concentration steadily increased the rate of the conversion.

Multidimensional heteronuclear NMR studies were performed with rPrP. Signal linewidths and spectral dispersion indicated that most of the protein is well-structured with the concentration (ca. 1 mM) and solution conditions employed: 20 mM sodium acetate, pH 5.2, 30° C. Analytical sedimentation confirmed that the protein was essentially monomeric; samples reached equilibrium after 15 h and did not change between 15 and 40 h at 25° C. The three sets of data fit well with a monomeric molecular weight of 16, 242 kDa with small residuals. Assuming a monomer-dimer equilibrium, the association equilibrium constant was calculated to be $5.4 \times 10^{-5} M^1$. These findings indicate that refolded rPrP is predominantly monomeric under the conditions of the NMR experiments.

Resonance assignments were made using samples of uniformly $^{15}N$- and $^{13}C$, $^{15}N$-labeled rPrP, primarily via scalar-coupling-based three-dimensional NMR spectra, including total correlated spectroscopy (TOCSY). There are essentially three parts to the protein readily reflected in simple spectral features: residues 90–112 are characterized by relatively narrow $^{15}N$ HSQC spectral signals and many NOE cross-peaks; residues 113–126 have relatively narrow $^{15}N$ HSQC spectral signals and many NOE cross-peaks; and most of the remaining residues exhibit ca. 6z broader HSQC signals and numerous NOE cross-peaks.

The $\alpha$-proton and $\alpha$-carbon chemical shift indices, as well as the proton NOE connectivities evidence in nuclear Overhauser effect spectra (NOESY) consistently indicate that rPrP contains three $\alpha$-helical regions. The locations of these correspond largely, but not entirely, to those found for MoPrP (121–231) under similar solution conditions (0.8 mM protein, pH 4.5, no buffer, 20° C.) and to two of the four helices predicted for the entire sequence.

From the NOE cross-peaks, 2401 experimental distance restraints were used to generate low-resolution structures via the program DIANA, followed by minimization with AMBER 4.1. A best-fit superposition of backbone atoms for residues 113–228 of rPrP is shown in FIG. 10. The helices and β-sheet are fairly well-defined, and loop regions can also be defined, although with less precision. To distinguish the α-helices found in rPrP by NMR from those predicted by molecular modeling, these were provisionally designated helices A, B and C. Helix A spans residues 144–157 with the last turn being quite distorted, corresponding to helix 144–154 found for MoPrP (121–231). Helix B spans residues 172–193, with the first turn being irregular at the present state of structure refinement. This is about two turns longer than the 179–193 helix found for MoPrP (121–231) which agrees well with predicted helix H3 (179–191). Helix C extends from residue 200 to 227 with the 225–227 turn being irregular, which is about three turns longer than the helix corresponding to residues 200–217 in MoPrP (121–231). It is notable that predicted helix H4 (residues 202–218) corresponds well with that found in MoPrP (121–231). Two four-residue β-strands (128–131 and 161–164) were identified in the MoPrP (121–231) structure. A similar antiparallel β-sheet was found, with S2 spanning residues 161–163 and S1 spanning 129–131 possessing β-sheet characteristics, but the two strands do not manifest standard β-sheet geometry. In fact, a β-bridge occurs only between $Leu^{130}$ and $Tyr^{162}$, and there are extensive cross-strand connectivities of residues in segment 129–134 with proximate residues on the antiparallel segment 159–165.

Figure 11A:
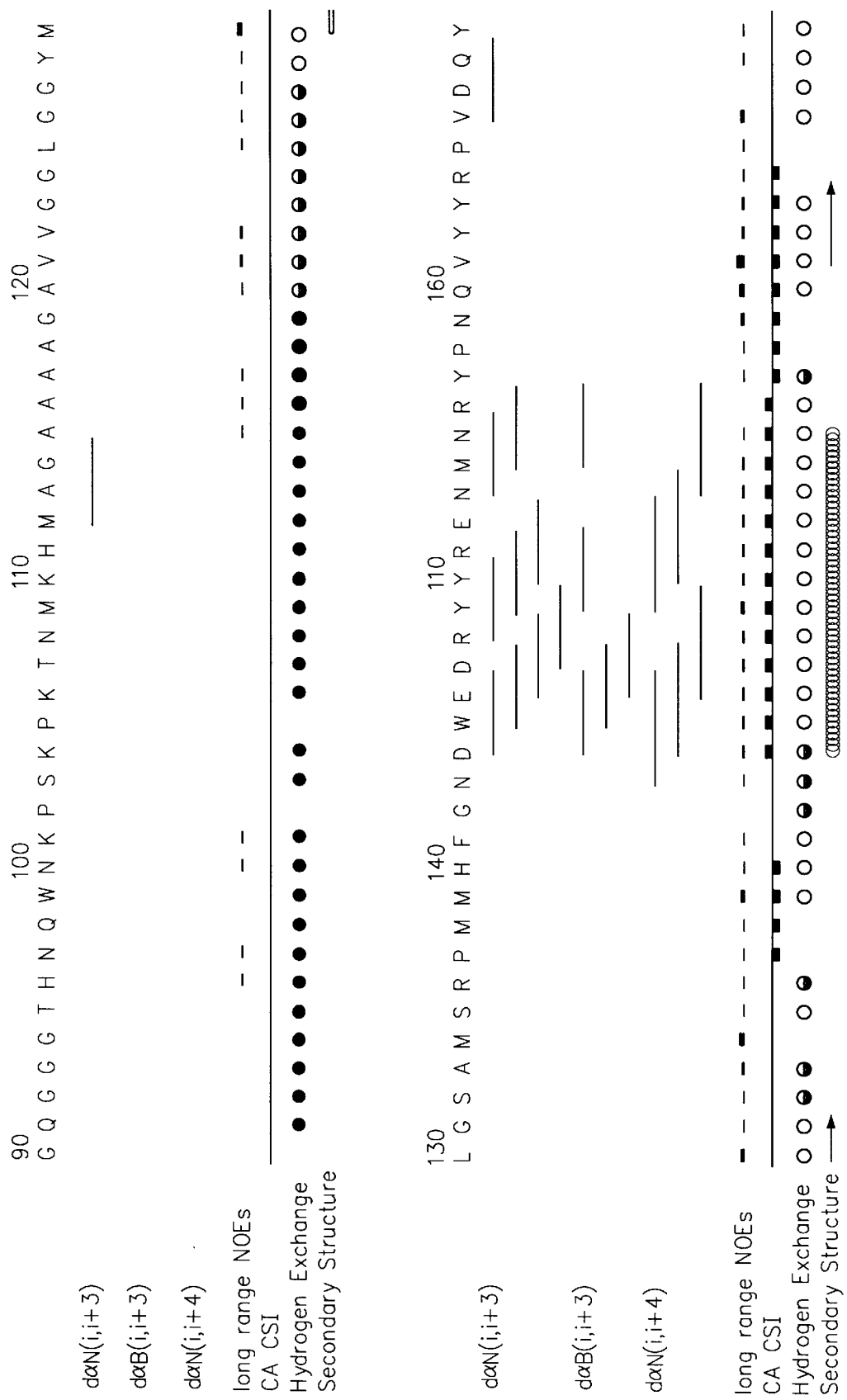
FIG. 11 (SEQ ID NOS:1 and 2) shows a portion of the 3D $^{13}$C-NOESY spectrum corresponding to $^{13}$C planes of the unresolved $Val^{166}$ methyl resonances and the $Ser^{222}$ resonances. The diagonal peaks and mirrored cross-peaks for each $^1H$—$^1H$ connectivity is shown. The solid lines connecting peaks designate NOE connectivities.
Figures 11, 11B:
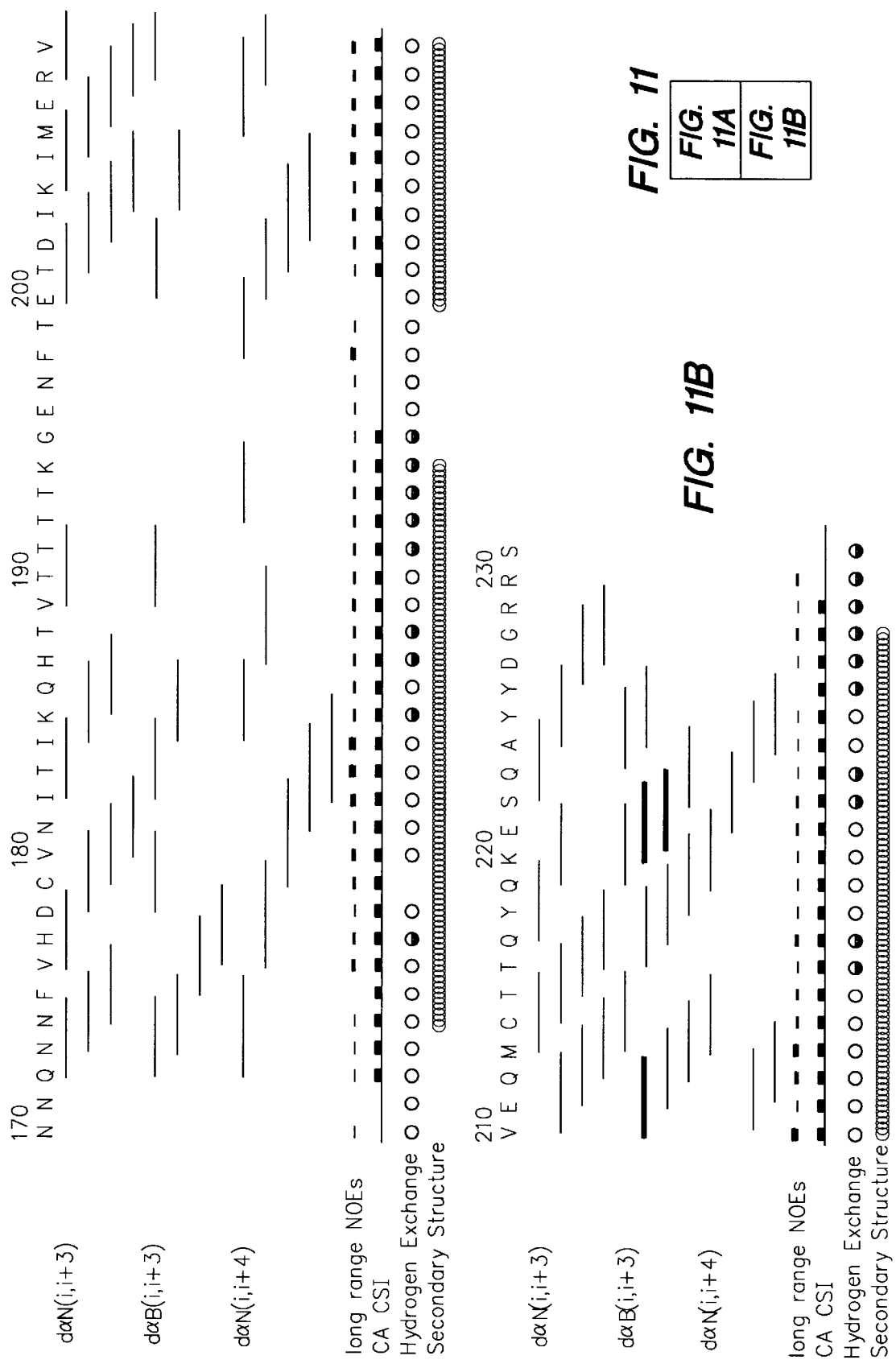

The loop between S2 and helix B (i.e., residues 165–71) yields resonances clearly exhibiting long-range as well as medium-range restraints in contrast to the absence of resonances for the backbone atoms of residues 167–176 in the shorter MoPrP (121–231). These results indicate that the loop is reasonably ordered, whereas it was concluded that this region is disordered in MoPrP (121–231). FIG. 11 shows only one example: $^1H$—$^1H$ cross-peaks between the unresolved methyl protons of $Val^{166}$ in that loop with $Ser^{222}$. However, the methyl protons of $Val^{166}$ also exhibit 15 long-range cross-peaks with protons in the same loop, e.g., $Tyr^{169}$, and in the extension of helix C, e.g., $Tyr^{218}$ and $Tyr^{22}$, which are on the same side of the helix. Connectivities of $Val^{166}$ to residues two turns apart on helix C suggest that the loop exits in multiple discrete conformations. In this contact, it is noteworthy that the loop is not under-defined; indeed, the multiple observed connectivities over-define the loop. Apparently, the interaction of the 165–171 loop with the helix C extension is important in stabilizing the structure.

FIG. 10 illustrates the relationship of the loop to helix C.

The α-proton and α-carbon chemical shifts for residues 90–127 are consistent with the region having substantial α-helical content, but the extent of the chemical shifts relative to that of random coil values was generally not enough to indicate the α-helix formation via tripartite chemical shift indices. There are also insufficient NOE connectivities to conclude α-helix is formed. The few medium-range connectivities in the segment 90–112 demonstrate sparse elements of structure. For example, for residues 95–100, results have so far identified 9 nonsequential NOE connectivities which imply that significant structure exists at least transiently. The small number of long-range connectivities for the N-terminal segment 90–112 imply that it is largely disordered.

Results obtained have identified 36 long-range NOE cross-peaks involving sidechain resonances for the hydrophobic residues in the segment 113–125. An uncommon combination of glycines and hydrophobic residues leads to an unusual, and dynamic, structural feature. Most of the NOE connectivities indicate that these residues form a hydrophobic globule with substantial backbone reversals permitted by the many glycines; indeed $Val^{121}$, $Val^{122}$, and $Leu^{125}$ each exhibit 10±3 long-range connectivities. As seen in FIG. 10, the backbone for this globule is not well-defined in spite of any connectivities. This may reflect the true dynamic nature of such a hydrophobic globule, as the $^{15}N$ HSQC spectral linewidths for these residues were also about 6 Hz smaller than for the core of the protein (ca. 18 vs. 24–25 Hz). Apparently, the combination of glycines with hydrophobic residues permits many alternative conformations with comparable free energies.

Figure 12:
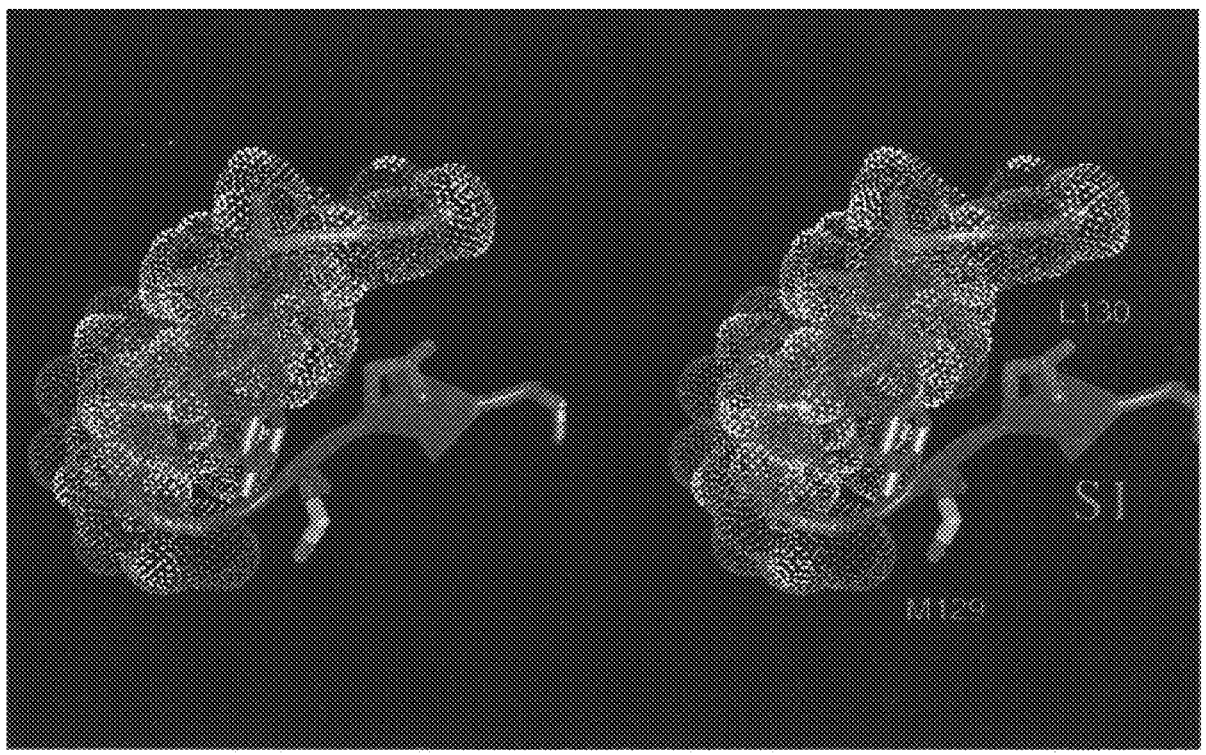

Some long-range connectivities place the hydrophobic globule adjacent to the β-sheet in contact with the S1 strand FIG. 12. The weak, broadened $^{15}N$ HSQC spectral signals for S1 residues $Met^{129}$ (32 Hz), $Leu^{130}$ (32 Hz) and $Gly^{131}$ (44 Hz) as well as S2 residues $Tyr^{162}$ (33 Hz) and $Arg^{164}$ (33 Hz) may well reflect conformational exchange effects in the interacting hydrophobic globule pervading the adjacent irregular β-sheet. Taken together, these results suggest that the hydrophobic globule and adjacent β-strands constitute a domain with marginally stable polymorphic structure.

The apparent conformational heterogeneity of the N-terminal region of rPrP may reflect the process by which $PrP^C$ is converted into $PrP^{Sc}$. Transgenetic studies also show that $PrP^{Sc}$ formation requires the substrate $PrP^C$ to bind the product $PrP^{Sc}$ at an intermediate stage of the conversion process. $PrP^C$ is thought to be in equilibrium with a metastable intermediate, designated PrP*, which binds to $PrP^{Sc}$ in the conversion process. In fact, destabilization of $PrP^C$ has been shown to be necessary for it to bind to $PrP^{Sc}$ in vitro. Further evidence for the conformational plasticity of PrP comes from unfolding studies of rPrP using guanidinium chloride (GdnHCl). The free energy difference $\Delta G_2$ of 6.5±1.2 kcal/mole between an intermediate state and the unfolded state was found to be comparable to literature values (5–15 kcal/mole) for protein unfolding. However, the completely refolded rPrP, as used for the present NMR studies, is only marginally more stable ($\Delta G_1$=1.9±0.4 kcal/mole) than the folding intermediate. This is consistent with the extensive conformational flexibility evident in the current NMR studies for part of the protein. The results also show another α-helical form of rPrP, formed by refolding at pH2, which exhibits NMR features characteristic of an acid-denatured molten globule but one that largely converts to the isoform studied here upon sitting for a few days at pD5.4 (corresponding to a pH meter reading of 5.0 measured in $H_2O$.

Figure 13:
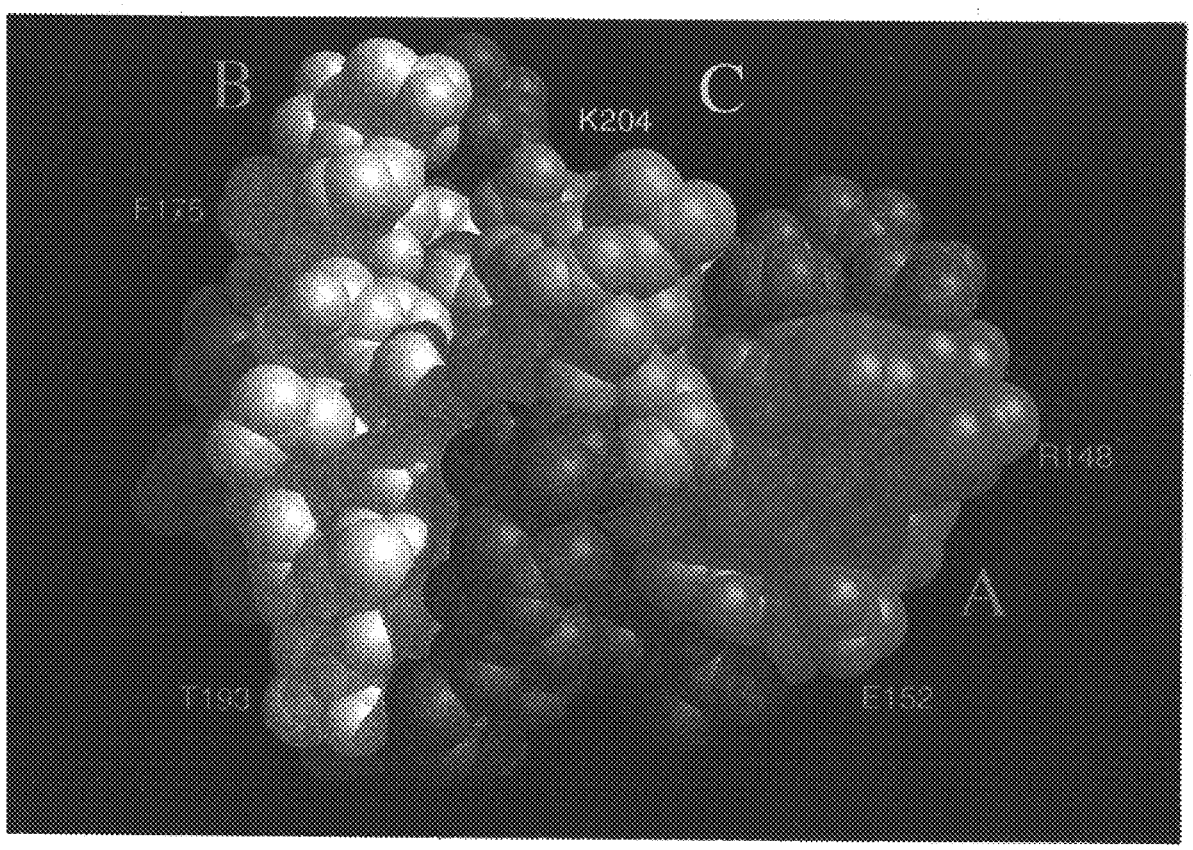
FIG. 13 is a computer generated structure showing Van der Waals surface of rPrP turned 90 from FIG. 10, illustrating the interaction of helix A with helix C. Helices A, B and C are respectively colored magenta, white and gold.
Figure 14:
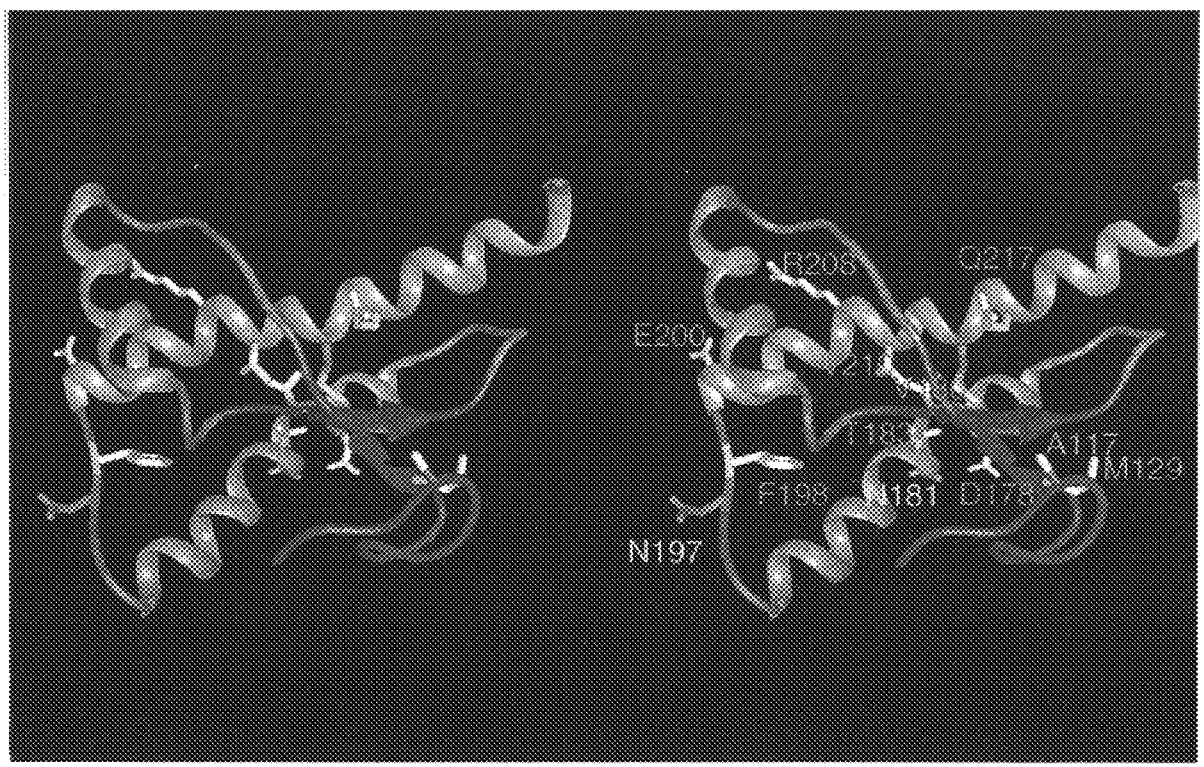

The NMR results for rPrP, compared to the structure reported for MoPrP, support the notion that the core of the $PrP^C$ structure is formed by parts of helices B and C, corresponding largely to the predicted H3 and H4 regions, and stabilized by the disulfide which is essential for α-helical folding. As seen in FIGS. 13 and 14, helices B and C essentially form one side of the protein structure. This core is further stabilized by helix A, which lies across helix C with sidechains between the two helices interacting (FIG. 13). Strand S2 also lies on this side of the protein and interacts predominantly with helices B and C as well as S1. With or without S2 and S1, we presume this relatively stable folding core is associated with the second unfolding transition. Attempts to prepare MoPrP (108–231) resulted in proteolytic cleavage producing MoPrP (121–131), indicative of a stable core beginning with residue 121. Conclusions about the "stable core" of PrP, however, must be considered within the context of a mutagenesis studies of a PrP with residues 23–89 and 141–176 deleted, i.e. removing helix A and strand S2; the resulting 106-residue PrP could be converted to a protease-resistant form.

Presence of the additional 31 N-terminal residues of rPrP, relative to MoPrP (121–231), induces substantial changes in the structure of PrP including alterations in the C-terminus. Helix C is extended by at least nine residues, helix B is up to seven residues longer, and the loop compromising residues 165–173 is sufficiently ordered that many long-range restraints can be observed.

The hydrophobic globule (residues 113–125) predominantly interacts with S1 in the β-sheet (FIG. 13). This may serve to stabilize the observed extension of helix B from 179 in MoPrP (121–231) to 172 in rPrP. Stability may also be conferred by hydrophobic interactions of $Tyr^{128}$ with $Tyr^{163}$ in the β-sheet which, in turn, interacts with $Val^{176}$. The relative stability of the 165–171 loop and the three additional helical turns in helix C are presumably connected to stabilization of the other structural elements.

Within the hydrophobic globule is a palindromic sequence, $A^{113}GAAAAGA$, that is conserved in all species examined to date, as are the surrounding residues. In humans the A117V mutation causes GSS, while an artificial set of mutations consisting of A113V, A115V, and A118V in Tg mice causes spontaneous neurodegeneration, promotes β-sheet formation in recombinant PrP, and generates prion infectivity de novo.

Strains of prions exhibit different incubation times before symptoms of disease appear and different patterns of $PrP^{Sc}$ accumulation. Recent work indicates that the properties of prion strains might be manifestations of different conformers of $PrP^{Sc}$. See Telling, et al, Science, December 1996. Studies on the transmission of human prions to transgenic mice also show that a species-specific PPMF, functions as a molecular chaperon in $PrP^{Sc}$ formation. These results show that PPMF forms a transient complex with the metastable intermediate PrP, diminishing the activation energy barrier between $PrP^{C}$ and $PrP^{Sc}$ and facilitating formation of $PrP^{Sc}$. An analysis comparing the three-turn extension of helix C to residue 227 in rPrP with the helix termination at $Gln^{217}$ in MoPrP (121–231) is consistent with this concept. SHa residues $Tyr215$ and $Gln^{219}$ are at the site of PPMF binding and the glycosylation sites, $Asn^{181}$, and $Asn^{197}$, are not very near this binding site (FIG. 14). In this context, the stability and length of helix C become an important issue. Interestingly, comparison of rPrP with MoPrP (121–231) suggests that omission of residues 90–120 destabilizes helix C resulting in its truncation as noted above and consequent disordering of residues 167–176. FIG. 7 shows that $Tyr^{215}$ and $Gln^{219}$ lie in register one turn apart on helix C and interact with the 165–173 loop residues. Residue 171 is a Gln in most species. When Suffolk sheep in the United States were studied, codon 171 was found to be polymorphic, encoding either Gln or Arg. All Suffolk sheep with scrapie were found to be Gln/Gln indicating that Arg conferred resistance. This observation along with the results shown here show that the basic sidechain of Arg prevents natural scrapie by either preventing binding of $PrP^{C}$ (R171) to PPMF or by increasing the affinity for PPMF such that $PrP^{C}$ is not readily released from the complex. The latter seems likely since heterozygous Arg/Gln sheep are also resistant to scrapie. Susceptibility to scrapie in other breeds of sheep is also determined largely by the nature of residue 171. Equally important is the observation that ~12% of the Japanese population encode Lys instead of Glu at position 219. No cases of CJD have been found in people with $Lys^{219}$ which, like Arg, is basic. These observation combined with the results shown here show that PPMF binds to a discontinuous epitope including residues 172, 215 and 219.

Residues where point mutations lead to human diseases are highlighted in FIG. 14. A point mutation in the PrP gene encoding $Asp^{178}$ leading to $Asn^{178}$ causes fatal familial insomnia if residue 129 is Met; the double mutation with $Met^{129}$ mutated to Val as well results in a subtype of CJD instead. Residue 178, which is in the extension of helix B seen in rPrP but not in MoPrP (121–231), and residue 129 are located opposite one another with strand S2 partially intervening (FIG. 14). If the mutation D178N destabilizes the structure, part of helix B could unravel. This part of helix B is near $Arg^{164}$ in S2, which in turn is adjacent to $Met^{129}$. Depending upon the identity of residue 129, the structure (or, in light of its stability, structural ensemble) resulting from this destabilization may differ.

Our structural studies of rPrP underscore the conformational plasticity evident in the N-terminal region and defines important structural features not evident in a smaller C-terminal fragment. Prior studies, including most recently with rFabs, indicate that the region corresponding to the N-terminal 30–40 residues of rPrP change conformation during formation of $PrP^{Sc}$.

EXAMPLES

The following examples are put forth so as to provide those of ordinary skill in the art with a complete disclosure and description of how to make and use the the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Binding Site in $PrP^{C}$ for PPMF

An examination of the amino acids which distinguish Hu PrP from Mo PrP shows only seven residues at the C-terminus (168–231) that are different. FIG. 8 is a comparison of sequences showing the differences. Four of these residues are close to the glycophosphatidylinosytol (GPI) anchor attached to Ser231 while the remaining three residues were within or near the C-terminus of a postulated α-helix which has been conformed by NMR structural studies. To identify the critical binding site within $PrP^{C}$ for PPMF the seven residues were divided into two groups: those at the C-terminal end of the last α-helix (HuA) and those at the extreme C-terminus (HuB) (FIG. 8). The Mo residues were replaced with Hu counterparts in positions that were critical for binding of $PrP^{C}$ to Mo PPMF to determine the effect of such on inhibiting the formation of recombinant $PrP^{Sc}$. Recombinant $PrP^{Sc}$ was distinguished from endogenous wild-type (wt) Mo $PrP^{Sc}$ by using the SHa/Mo chimeric PrP designated MHM2 that contains a binding site for the anti-SHa PrP 3F4 monoclonal antibody (mAb).

Three chimeric constructs, denoted as MHMHuA (Mo residues 214, 218 and 219 were replaced with the corresponding human residue), MHMHuB (Mo residues 226 through 230 replaced with Hu), and MHMHu(A+B) (combined replacements), were transiently transfected into scrapie infected Mo neuroblastoma (ScN2a) cells (FIG. 8). Neither MHMHu(A+B) nor MHMHuA was converted into $PrP^{Sc}$ as judged by the acquisition of protease resistance. By contrast, MHMHuB was converted into PrP$^{Sc}$ as efficiently as the control MHM2. These results indicate that Mo PPMF did not bind to MHMHu(A+B) or to MHMuA but did bind to MHMHuB and MHM2, both of which were converted into PrP$^{Sc}$.

Example 2

Example 1 identifies the HuA region which prevents conversion of modified PrP$^C$ into PrP$^{Sc}$. Additional constructs were then produced with Mo residue 214 replaced by its Hu counterpart (MHMHuA1), 218 and 219 replaced by the Hu homologues (MHMHuA2), Mo 218 replaced by its Hu counterpart (MHMHuA3), Mo 219 replaced by the Hu one (MHMHuA4), and Mo 214 and 218 replaced by the Hu homologues (MHMHuA5) (FIG. 8). Neither MHMHuA2, MHMHuA3 nor MHMHuA5 were converted into PrP$^{Sc}$, while MHMHuA1 was converted but at a reduced level compared to MHMHuA4 and MHMHuB. It should be noted that longer film exposure revealed what appeared to be a trace amount of PrP$^{Sc}$ formation in MHMHuA2 and MHM-HuA3 but not in MHMHuA5.

The experiments described above show that substitution of the Hu encoded Glu residue for Gln in Mo PrP$^C$ at position 218 prevented its conversion into PrP$^{Sc}$. In addition, substitution of the Hu encoded Ile residue for Val in Mo PrP$^C$ at position 214 ameliorated this inhibition. These data argue that the region of PrP$^C$ around the segment bounded by residues 214 and 218 participates in the formation of PrP$^{Sc}$. There is no known metal, protein, or DNA binding motif in this region. Experiments with phosphatidylinositolphospholiphase C (PIPLC) revealed no topological changes in these chimeric constructs.

Example 3

Artificial Mutations At Mo Residues 214 and 218

A Hu polymorphism at residue 219 (corresponding to Mo 218) has been reported in the Japanese population where about 12% of the people have the Lys allele instead of the Glu/Glu allele. Experiments were carried out to investigate the influence of the polymorphism by introducing Lys at Mo residue 218 into MHM2 PrP$^C$ (MHMK 218, FIG. 8). The results obtained show that Lys at Mo 218 completely abolished the PrP$^{Sc}$ formation (Table 1). This result indicates that the Lys allele at Mo 218 has an aberrant affinity to Mo PPMF and subsequently exhibits no PrP$^{Sc}$ formation. To further investigate the effect of amino acid substitutions at the residue 218, four artificial mutations were introduced; Ile (MHM1218), Ala (MHMA218), Trp (MHMW218), Pro (MHMP218) (FIG. 8). MHM1218 and MHMW218 converted into PrP$^{Sc}$ but much less efficiently, whereas neither MHMA218 not MHMP218 showed conversion to PrP$^{Sc}$.

Mutations at residue 214 hindered the formation of recombinant PrP$^{Sc}$ but in a different manner. In addition to MHMHuA1 (Ile at 214), MHMA214 (Ala at 214) was converted, albeit less efficiently, into MHMA214 PrP$^{Sc}$ however MHMK214 (Lys at 214), MHME214 (Glu at 214) MHMW214 (Trp at 214), nor MHMP214 (Pro at 214) were not converted (Table 1). These experiments show that amino acid 214 is on the periphery of the binding interface between PrP$^C$ and PPMF while residue 218 occupies a more central region of that binding interface.

Example 4

Binding Characteristics of PPMF to PrP$^C$ in PrP$^{Sc}$ Formation

In order to determine how residue 218 provides species specific binding to PPMF, mutants of PrP$^C$ were serially co-transfected into ScN2a cells to analyze any interactions between the different PrP$^C$ and Mo PrP$^{Sc}$ under conditions where the concentration of PPMF can be limiting. In this regime, inhibition is observed between Mo and SHa PrP in ScN2a cells in a manner similar to that observed in Tg mice showing significantly reduced Mo PrP$^{Sc}$ following Mo prion inoculation in the presence of heterologous expression of SHa PrP$^C$. Since neither SHa nor MH3 PrP$^C$ (FIG. 8) could be efficiently converted into PrP$^{Sc}$, MHM2 PrP$^{Sc}$ formation was dramatically reduced when co-transfected. MH2M PrP$^C$ (FIG. 8) was less efficiently converted into PrP$^{Sc}$ with an intermediate amount of inhibition on MHM2PrP$^{Sc}$ formation when co-transfected. On the other hand, co-expression of Mo PrP$^C$ (FIG. 8), which was efficiently converted into PrP$^{Sc}$ (3F4 does not recognize Mo PrP$^{Sc}$), did not affect MHM2 PrP$^{Sc}$ formation when co-transfected.

Neither MH3HuA, MH2HuA PrP, nor M3HuA PrP exhibited any inhibition on MHM2 PrP$^{Sc}$ formation when co-transfected even if they did not convert into PrP$^{Sc}$ (Table 1) in marked contrast to SHa or MH3 PrP$^C$. When the HuA sequence was introduced into MH3 PrP$^C$ (MH3HuA), the inhibition with SHa derivatives was abolished. This indicates that the HuA region primarily governs the inhibition in the PrP$^{Sc}$ formation over the PrP$^C$-PrP$^{Sc}$ interaction determined by the central region.

Mutant PrP$^C$ failed to efficiently convert into the PrP$^{Sc}$ isoform, indicating that mutations at Mo residue 218 might produce a tightly associating complex between PPMF and PrP$^C$ thereby eliminating subsequent PrP$^{Sc}$ formation. To confirm such constructs carrying each mutation at residue 218 were co-transfected with MHM2 PrP$^C$. The higher the binding affinity between PPMF and the mutant protein the more unbound PPMF is depleted resulting in supression of the conversion of co-expressed PrP$^C$ into PrP$^{Sc}$. In addition, MHMHuA derivatives (Glu at 218), MHM1218 as well as MHMP218 demonstrated no significant inhibition on the formation of MHM2 PrP$^{Sc}$ when co-transfected. On the other hand, MHMA218 as well as MHMW218 exhibited remarkable inhibition (Table 1). These results indicate that MHMK218, MHMA218 and MHMW218 bind to PPMF even tighter than wt-MHM2 (Gln at 218) does.

At residue 214, MHM1214, MHME214 and MHMW214 exhibited competitive inhibition on the conversion of MHM2 PrP$^C$ into PrP$^{Sc}$ when co-transfected, whereas MHMK214, MHMA214 and MHMP214 did not (Table 1). At the Mo residue 214, MHM1214, MHIE214, and MHMW214 have tighter binding to PPMF than MHM2-PrP$^C$ does.

Example 5

Mutations at Mo Residue 216

A Swedish family with GSS has been reported with a mutation of Gln 217 Arg (216 in Mo). Brain samples in this GSS family showed no infectivity or protease resistant PrP$^{Sc}$ on Western blots. To determine binding affinity to PPMF, Arg was introduced at Mo residue 216 in MHM2 PrP carrying either the Mo (MHMR216) or Hu sequence at residue 218 (MHMHuR216). Neither MHMR216 nor MHMHuR216 produced any PrP$^{Sc}$ on Western blots (Table 1). When co-transfected with MHM2 PrP$^C$, however, MHMR216 (Gln at 218) inhibited formation of the MHM2 PrP$^{Sc}$, while MHMHuR216 (Glu at 218)did not (Table 1). This limited set of mutations at Mo residue 216 shows that binding of PPMF to PrP$^C$ is independent of residue 216. This is consistent with the quite distinct orientations of side chains of residue 216 and 218 on the C-terminal α-helix of PrP$^C$.

Materials and Methods

Cultured Cells

N2a cells were obtained from American Tissue Culture Collection (Rockville, Md.). ScN2a cells are the persistently infected clones as described [Butler, et al., *J. Virol.* 62:1558–1564 (1988)]. All the cells were grown and maintained at 37° C. in MEM supplemented with 10% FBS. In some cases, cells were treated with PIPLC. Cells grown on 60 mm dishes were rinsed with ice-cold PBS, then incubated with 0.5 U PIPLC in 1 ml of OptiMEM at 37° C. for 4 h with swirling.

Antibodies

α-PrP 3F4 is a mAb raised against SHa PrP27–30 [Kascsak, et al., *J. Virol.* 61:3688–3693 (1987)]. To distinguish the signals of MHM2-constructs from endogenous Mo $PrP^{Sc}$, 3F4 mAb was used since this antibody exclusively recognizes SHa, MHM2 PrP, MH2M, and MH3 PrP derivatives at $Met_{109}$-$Met_{112}$ [Rogers, *Glycobiology* 1:101–109 (1990)]. R073 is an antiserum raised in a rabbit against SDS-PAGE purified SHa PrP 27–30 reacts with SHa MH3, MH2M, M3H, Mo, and MHM2 PrP derivatives [Serban, et al., *Neurology* 40:110–117 (1990)].

Recombinant Gene Construction

MHM2 PrP was constructed as described [Scott, et al., *Protein Sci.* 1:986–997 (1992)]. MHM2 PrP in pSPOX was digested with BstEll and Hindlll, then the 1.4 kbp fragment was ligated into BstEll-Hindlll double digested Hu PrP in pSPOX, yielding MHM2Hu(A+B). MHMHu(A+B) in pSP72 was digested with Xhol and Stul, then either the 2.4 kbp or the 880 bp fragment was ligated to MHM2 in pSP72, yielding MHMHuA or MHMHuB, which were then introduced into the expression plasmid pSPOX.

MH2M or Mo PrP in pSPOX was digested with BstEll and Hindlll, then 1.4 kbp fragment was ligated into BstEll-Hindlll double digested MHMHuA PrP in pSPOX, yielding MH2HuA and M3HuA. BstEll and Xhol restriction sites were introduced in the MHM2 by using the mismatched (underlined) BstH (5' ATC AAG CAG CAC ACG GTC ACC ACC ACC AAG GGG GAG AAC TTC ACC GAG ACC GAT ATC AAG ATA ATG) SEQ ID NO:01 resulting in the mutations $Val_{202}$→lle and $Met_{204}$→lle, coupled with Xho (5' CAC TAT AGA ACT CGA GCA GCC TCC CT) SEQ ID NO:02. After the PCR, amplified fragments were digested with restriction enzymes as described above, then ligated into the MHM2 PrP in pSPOX vector, yielding MH3HuA.

BstEll and Stul restriction sites were introduced in the MHM2 by using the mismatched (underlined) HuA1 (5' ATA GGC CTG GGA CTC CTT CTG GTA CTG GGT GAT GCA) SEQ ID NO:03 resulting in the mutation $Val_{214}$→lle; HuA2 (5' ATA GGC CTG GGA CTC CCT CTC GTA CT) SEQ ID NO:04, $Gln_{218}$→Glu and $Lys_{219}$→Arg; HuA3 (5' ATA GGC CTG GGA CTC CTT CTC GTA CT) SEQ ID NO:05, $Gln_{218}$→Glu; HuA4 (5' ATA GGC CTG GGA CTC CCT CTG GTA CT) SEQ ID NO:06, $Lys_{219}$→Arg; HuA5 (5' ATA GGC CTG GGA CTC CCT CTG GTA CTG GGT GAT GCA) SEQ ID NO:07 $Val_{214}$→lle and $Gln_{218}$→Glu; K218 (5' ATA GGC CTG GGA CTC CTT TTT GTA CT) SEQ ID NO:08 resulting in the mutation $Gln_{218}$→Lys; 1218 (5' ATA GGC CTG GGA CTC CTT GAT GTA CT) SEQ ID NO:09, $Gln_{218}$→lle; A218 (5' ATA GGC CTG GGA CTC CTT CCG GTA CT) SEQ ID NO:10, $Gln_{218}$→Ala; W218 (5' ATA GGC CTG GGA CTC CTT CCA GTA CT) SEQ ID NO:11, $Gln_{218}$→Trp; P218 (5' ATA GGC CTG GGA CTC CTT CGG GTA CT) SEQ ID NO:12, $Gln_{218}$→Pro; R216 (5' ATA GGC CTG GGA CTC CTT CTG GTA CCG GGT GAC GCA) SEQ ID NO:13, $Gln_{216}$→Arg; HuR216 (5' ATA GGC CTG GGA CTC CTT CTC GTA CCG GGT GAC GCA) SEQ ID NO:14, $Gln_{216}$→Arg and $Gln_{218}$→Glu; K214 (5' ATA GGC CTG GGA CTC CTT CTG GTA CTG GGT CTT GCA) SEQ ID NO:15 resulting in the mutation $Val_{214}$→Lys; E214 (5' ATA GGC CTG GGA CTC CTT CTG GTA CTG GGT CTC GCA) SEQ ID NO:16, $Val_{214}$→Glu; A214 (5' ATA GGC CTG GGA CTC CTT CTG GTA CTG GGT GGC GCA) SEQ ID NO:17, $Val_{214}$→Ala; WA214 (5' ATA GGC CTG GGA CTC CTT CTG GTA CTG GGT CCA GCA) SEQ ID NO:18 $Val_{214}$→Trp; or P214 (5' ATA GGC CTG GGA CTC CTT CTG GTA CTG GGT GGG GCA) SEQ ID NO:19 $Val_{214}$→Pro, coupled with Bst (5' ATC AAG CAG CAC ACG GTC ACC ACC A) SEQ ID NO:20. After polymerase chain reaction (PCR), amplified fragments were digested with restriction enzymes as described above, then ligated into the MHM2 PrP in pSP72 vector, yielding MHMHuA1 through MHMHuA5, MHMK218, MHM1218, MHMA218, MHMW218, MHMP218, MHMR216, MHMHuR216, MHMK214, MHME214, MHMA214, MHMW214, or MHMP214, which were then introduced into the expression plasmid pSPOX.

Transfection and Western Blots

ScN2a cells were transiently transfected with each construct using a DNA transfection kit (DOTAP, Boehringer Mannheim, Indianapolis, Ind.). Cell lysis and Western blots were performed as described previously [Scott, et al., *Protein Sci.* 1:986–997 (1992)].

Co-transfection in which ScN2a cells were exposed simultaneously to two different genes showed that transfected cells co-expressed the two genes at an extremely high frequency (>85%) in 10–15% of total ScN2a cells in which the transfection was successfully proceeded (data not shown). When equal amounts of two different DNAs cloned into pSPOX were applied for the transfection as in the current experiments, the expression levels of each molecule were equal by Western blotting. In the ScN2a cell culture system, the expression levels of transfectants were significantly higher than that of endogenous Mo PrP since Western blotting stained with polyclonal R073 still represented the same original patterns on the pre PK-digested samples as with 3F4 mAb.

Example 6

Construction of Chimeric Gene (MHu2M)

The source of the HuPrP ORF for construction of an expression cassette has been described [Hsiao et al., *Nature* 338:342–345 (1989)]. The construction of the MHu2M gene is described in connection with the description of FIG. 1. All PrP ORF cassettes were flanked by Sall and Xhol, which cleave immediately adjacent to the PrP initiation and termination codons of the PrP ORF respectively, allowing for convenient subcloning into the cos.SHaTet cosmid expression vector [Scott et al., *Cell* 73:979–988 (1993)]. The isolation and screening of recombinant cosmid clones was achieved by methods which have been previously described [Scott et al., *Cell* 73:979–988 (1993)].

Example 7

Producing Transgenic Mice/Tg(MHu2M)

The nucleotide sequences of the HuPrP and MHu2MPrP ORFs of Example 6 were verified. The cosmid Notl fragments, recovered from large-scale DNA preparations, were used for microinjection into the pronuclei of fertilized C57BL/6 X SJL or FVB/N oocytes as previously described [Scott et al., Cell 59:847–857 (1989); Scott et al., Protein Sci. 1:986–997 (1992)]. Genomic DNA isolated from tail tissue of weaning animals was screened for the presence of incorporated transgenes using a probe that hybridizes to the 3'-untranslated region of the SHaPrP gene contained in the cosSHa.Tet vector [Scott et al., Protein Sci. 1:986–997 (1992)]. The offspring obtained were tested and it was confirmed that the chimeric MHu2M gene was integrated into the genome of these offspring. As shown in Example 10 below, these mice were found to be susceptible to infection with human prions 100% of the time.

Example 8

Preparation of Brain Homogenates

A 10% [w/v] homogenate of a sample of thawed human brain tissue was prepared in phosphate buffered saline lacking calcium and magnesium ions. The tissue was initially dissociated using a sterile disposable homogenizer, and this suspension was subjected to repeated extrusion through an 18 gauge syringe needle followed by a 22 gauge needle. Samples for inoculation into test animals were diluted 10-fold. Homogenates of clinically sick Tg and non-Tg mouse brains were prepared in the same way except for the omission of the initial dissociation step.

Example 9

Sources of Prion Inocula

Human inocula were derived from frozen brain tissues of patients in which the clinical diagnosis of CJD or GSS had been confirmed by histopathological examination of brain tissues and, in most cases, by prion protein analysis. In some cases, the PrP gene was amplified by PCR of DNA isolated from patient blood and the PrP sequence determined by DNA sequence analysis. No HuPrP mutations were detected in cases of sporadic or iatrogenic CJD. The RML isolate was obtained from Swiss mice [Chandler, R. L., Lancet 1:1378–1379 (1961)] from a closed colony at the Rocky Mountain Laboratory or in Swiss CD-1 mice obtained from Charles River Laboratories.

Example 10

Determination of Scrapie Incubation Periods

Transgenic mice as per Example 7 were inoculated intracerebrally with 30 μl of brain extract using a 27 gauge needle inserted into the right parietal lobe. The preparation of inocula and criteria for diagnosis of scrapie in mice have been described [Carlson et al., Cell 46:503–511 (1986)]. Beginning 50 days after inoculation, the mice were examined for neurologic dysfunction every 3 days. When clinical signs of scrapie appeared, the mice were examined daily. When some animals whose death was obviously imminent were identified, their brains were taken for histopathologic studies (as per the procedures of Example 8) and confirmation of the diagnosis of scrapie.

Example 11

Immunoblot Analysis

For the determination of the relative levels of PrP expression in Tg mouse and human brains, protein concentrations were determined by bicinchoninic acid assay and immuno dots blots as previously described [Scott et al., Cell 73:979–988 (1993)]. Samples for Western blot analysis were prepared and western blots were performed as described previously [Towbin et al., Proc. Natl. Acad. Sci. USA 76:4350–4354 (1979)], except that an enhanced chemiluminescent (ECL) detection method (Amersham) was used. The blot was exposed to X-ray film for 5–60 seconds. α-PrP R073 rabbit antiserum was used at a final dilution of 1:5000 and 3F4 monoclonal antibody was also employed [Serban et al., Neurology 40:110–117 (1990)].

Example 12

Creating Mammals which Express PPMF

Identifying the amino acid sequence(s) in MoPrP responsible for the binding of mouse PPMF and construct a modified MoPrP gene in which the sequence for this binding site is mutated. Such a benign MoPrP molecule will not interfere with human prion propagation in transgenic mice expressing HuPrP because PPMF is not sequestered by the mutant MoPrP. Following the above-described procedures in which the MoPrP gene is replaced with HuPrP or modified MoPrP genes, it is possible to create transgenic mice expressing HuPrP using these new genetic backgrounds either by genetic crosses or by direct microinjection of a vector capable of directing expression of HuPrP into fertilized embryos from these newly-created transgenic mouse lines.

Example 13

Mutant PrP Conversion into PrP$^{Sc}$

Three chimeric constructs, denoted as MHMHuA (Mo residues 214, 218 and 219 replaced with Hu), MHMHuB (Mo residues 226 through 230 replaced with Hu), and MHMHu(A+B) (combined replacements), were transfected transiently into scrapie infected Mo neuroblastoma (ScN2a) cells (Table 3). Neither MHMHu(A+B) nor MHMHuA was converted into PrP$^{Sc}$ as judged by the acquisition of protease resistance. In contrast, MHMHuB was converted into PrP$^{Sc}$ as efficiently as the control MHM2. We interpreted these results as indicating that Mo PPMF did not bind to MHMHu (A+B) or MHMHuA but did recognize MHMHuB and MHM2, both of which were converted into PrP$^{Sc}$. The mutant PrP molecules were all expressed at about the same level, and no inhibition of wt MoPrP$^{Sc}$ formation could be detected.

Having identified the HuA region which prevents conversion of modified PrP$^C$ into PrP$^{Sc}$, we produced additional constructs with Mo residues 214, 218 and 219 replaced by their Hu counterparts (FIG. 15). To test the replacement of these residues either alone or in combination, we generated five constructs which were expressed then in ScN2a cells. Substitution of Hu residue 218 abolished PrP$^{Sc}$ while substitution of Hu residue 219 was not inhibitory. Substitution of Hu residue 214 was partially inhibitory.

These results show that substitution of the Hu encoded Glu residue for Gln in Mo PrP$^C$ at position 218 prevented its conversion into PrP$^{Sc}$. In addition, substitution of the Hu encoded Ile residue for Val in Mo PrP$^C$ at position 214 was also inhibitory. These data argue that the region of PrP$^C$ around the segment bounded by Mo residues 214 and 218 participates in the formation of PrP$^{Sc}$. Since Mo residues 214 and 218 lie one turn apart with the C-terminal α-helix of PrP, their side chains protrude from the same surface. These data argue that the region of PrP$^C$ around the segment bounded by Mo residues 214 and 218 participates in the formation of PrP$^{Sc}$. There is no known metal, protein, or DNA binding motif in this region. Since the GPI anchor of PrP$^C$ targets to caveolae where PrP$^{Sc}$ formation seems to occur. An inquiry was made as to whether any of these amino acid substitutions prevented GPI anchor addition and transport of PrP$^C$ to the cell surface. Studies of chimeric PrP$^C$ released from the cell surface with phosphatidylinositophospholipase C (PIPLC) digestion revealed no topological changes.

Example 14

Specificity of PrP Mutations at Mo Residues 214 and 218

Since substitution of the negatively charged Hu Glu residue for Mo Gln at position 218 inhibited conversion of this mutant PrP into PrP$^{Sc}$ experiments were carried out to determine if other amino acids would exhibit a similar effect. In humans, position 219 corresponding to mouse 218 is polymorphic: in Caucasians only Glu at this residue has been reported, whereas about 12% of Japanese people have the Lys allele. The substitution of Lys at Mo residue 218 abolished the PrP$^{Sc}$ formation. To examine the specificity of amino acid substitutions at position 218, an examination was made of the effect of amino acid substitutions at the residue 218, by introducing 7 artificial mutations, Ile, Ala, Trp, Pro, Phe, Arg, or His (See FIG. 8). The constructs expressing Ala, Pro, Phe, Arg, or His at position 218 were not converted into PrP$^{Sc}$, whereas, low amounts of PrP$^{Sc}$ were made with the Ile or Trp at residue 218.

Substitution of Hu Ile at residue 214 diminished but did not completely abolish PrP$^{Sc}$ formation. Similarly, modest PrP$^{Sc}$ formation was observed with Ala. No PrP$^{Sc}$ was observed when Lys, Glu, Trp or Pro were substituted at position 214. The mutant PrP molecules were all expressed at about the same level except when Pro was substituted at position 218, Arg at 216 or Pro 214. Substitutions of Pro in the C-terminal α-helix are expected to destabilize this secondary structure and may result in the increased liability of the protein. No inhibition of wt MoPrP$^{Sc}$ formation by the mutant PrP molecules could be detected.

Example 15

Mutant PrPs and Conversion of Wt PrP into PrP$^{Sc}$

Since only a minority of the ScN2a cells express the mutant PrPs in these transient transfection experiments, it was not possible to assess the effect of expressing mutant PrP conversion of wt MoPrP into PrP$^{Sc}$. To measure the influence of mutant PrP on the conversion of wt PrP into PrP$^{Sc}$ cotransfection studies were performed. In these experiments, epitope tagged MHM2 PrP without (wt) or with a mutation were transfected together into ScN2a cells. Several studies have established that the trensfecting DNAs are generally taken up together and coexpressed.

Substitution of Glu, Ile, Pro or Phe at residue 218 did not inhibit conversion of epitope tagged wt MHM2 PrP$^C$ into PrP$^{Sc}$. In contrast, Lys, Ala, Trp, Arg or His at position 218 inhibited wt PrP$^{Sc}$ formation. These results show that the MHM2 PrP carrying Lys, Ala, Trp, Arg or His at residue 218 binds to PPMF with a greater affinity than does wt MHM2 with Gln at 218. These findings also contend that the two polymorphic Hu residues Glu and Lys interact very differently with Mo PPMF. Mutant MHM2 PrP(E218) binds more weakly to Mo PPMF than does wt MHM2 PrP(Q218) which results in MHM2 PrP(E218) not being converted into PrP$^{Sc}$ and no inhibition of the conversion of wt MHM2 PrP$^C$ into PrP$^{Sc}$. In contrast, mutant MHM2 PrP(K218) binds more tightly to Mo PPMF than does wt MHM2 PrP(Q218) which results in both MHM2 PrP(K218) not being converted into PrP$^{Sc}$ and inhibition of the conversion of wt MHM2 PrP$^C$ into PrP$^{Sc}$.

The substitution of Lys, Ala or Pro at residue 214 did not inhibit conversion of epitope tagged wt MHM2 PrP$^C$ into PrP$^{Sc}$. In contrast, Ile, Glu or Trp at position 214 inhibited wt PrP$^{Sc}$ formation. These results argue that the MHM2 PrP carrying Ile, Glu or Trp at position 214 binds to PPMF with a greater affinity than does wt MHM2 with Val at 218.

Example 16

Mutation at Mo Residue 216

MoPrP codon 216 which encodes a Gln residue in both Mo and Hu PrP was mutagenized because the side chain of this residue protrudes from the opposite face of the C-terminal α-helix at positions 214 and 218 and a mutation causes inherited prion disease. A Swedish family with GSS has been reported with a Q→R mutation, Hu codon 217 corresponds to Mo codon 216. Although brain sections showed PrP amyloid plaques, extracts showed neither infectivity nor protease resistant PrP$^{Sc}$ on Western blots.

Arg was introduced at residue 216 in MHM2 PrP and MHM2 PrP(E218) which contains the Hu Glu residue at 218. Neither of these mutant PrPs acquired resistance when expressed in ScN2a cells. The Arg substitution at residue 216 inhibited conversion of epitope tagged wt MHM2 PrP$^C$ into PrP$^{Sc}$. Whereas, no inhibition was observed if both residues 216 and 218 were mutated. These findings show that the Q→R mutation destabilizes the structure of PrP$^C$ leading to inherited prion disease and prevents folding into a protease resistant PrP$^{Sc}$ molecule. The Mo Gln residue at 218 allows MHM2 PrP(R216) to compete with wt MHM2 PrP for binding to PPMF whereas the Hu Glu residue decreases the affinity of this protein for PPMF. With the Hu Glu residue, no inhibition of the conversion of wt MHM2 PrP into PrP$^{Sc}$ was observed.

Example 17

Mutations At Mo Residues 215, 221 and 222

Substitution of Gln for Thr at MoPrP residue 215, Ala for Ser at Mo 221 or Lys for Gln at Mo 222 did not inhibit conversion of these epitope tagged MHM2 PrP molecules into PrP$^{Sc}$ when expressed into PrP$^{Sc}$ when expressed in ScN2a cells (Table 1). Co-expression of these mutant MHM2 PrPs with wt MHM2 PrP did not inhibit wt PrP$^{Sc}$ formation. When the V214D mutation was introduced into MHM2 PrP(S221A), the protein was not converted into PrP$^{Sc}$ suggesting that the V214D mutation prevented binding to PPMF.

Example 18

Mutation At Mo Residue 171

Results obtained show that mutations of Mo residues 214 and 218 inhibit PrP$^{Sc}$ formation, showing that the surface of the C-terminal α-helix with the side chains of these residues is the binding site for PPMF. The NMR structure of SHa rPrP90–231 shows a loop composed of residues 165–173 immediately adjacent to the PPMF binding site on the helix raising the possibility that one or more of these residues also participates in the binding to PPMF. To explore this possibility, we constructed mutant MHM2 PrP(N170S) and MHM2 PrP(Q171R) and transfected the DNAs into ScN2a cells. MHM2 PrP(N170S) was converted into PrP$^{Sc}$ whereas MHM2 PrP(Q171R) was not. The Ser substiutution at Mo residue 170 did not inhibit conversion of epitope tagged wt MHM2 PrP$^C$ into PrP$^{Sc}$, whereas the Arg substitution inhibited PrP$^{Sc}$ formation. These findings argue that Q171 in MoPrP forms a discontinuous epitope with V214 and Q218 to which PPMF binds.

Example 19

SHaPrP Inhibits Conversion MHM2 into PrP$^{Sc}$

The level of SHaPrP$^C$ expression in Tg(SHaPrP)Prnp$^{+/+}$ mice was directly proportional to the length of the incubation time after inoculation with Mo prions. To simulate these conditions in ScN2a cells, epitope-tagged MHM2 PrP was coexpressed with SHaPrP or chimeric SHa/MoPrP. SHaPrP and chimeric MH3 PrP inhibited conversion of MHM2 PrP into PrP$^{Sc}$ but this inhibition was relieved by substitution of Hu residues at positions 214, 218 and 219 designated HuA. As described above mutant PrP molecules with Hu residues at 214 and 218 were not converted into PrP$^{Sc}$ in ScN2a cells and did not inhibit the transformation of MHM2 PrP into PrP$^{Sc}$.

While neither SHa nor MH3 PrP$^C$ could be efficiently converted into PrP$^{Sc}$ in ScN2a cells reducing the extent of SHaPrP sequence resulted in a progressive increase in PrP$^{Sc}$ formation. MH2M PrP was converted into PrP$^{Sc}$ at a level intermediate between MH3 PrP and MHM2 PrP. Expression of MH2M PrP with MHM2 PrP decreased the level of conversion of MHM2 into PrP$^{Sc}$. Expression of MoPrP with MHM2 PrP did not inhibit the formation of PrP$^{Sc}$ from MHM2 PrP.

The foregoing findings help define the order of addition during formation of the PPMF PrP$^C$/PrP$^{Sc}$ complex as well as the limits of central domain of PrP where PrP$^C$ and PrP$^{Sc}$ interact. When Hu residues at 214, 218 and 219 (HuA) were introduced into MH2M or MH3 PrP, these chimeric PrPs no longer inhibited the conversion of MHM2 PrP into PrP$^{Sc}$. The HuA substitutions relieve inhibition by preventing the binding of the chimeric MH3HuA PrP. This shows that the lack of conversion of SHaPrP or MH3 PrP into PrP$^{Sc}$ is not due to a low affinity for PPMF. Instead, MoPrP$^{Sc}$ does not stimulate conversion of SHaPrP or MH3 PrP into PrP$^{Sc}$ even though these molecules are bound to PPMF. This contention is supported by the ability of SHaPrP$^{Sc}$ to stimulate conversion of SHaPrP$^C$ into PrP$^{Sc}$ in Tg(SHaPrP)PrP$^{+/+}$ mice when MoPrP$^C$ is coexpressed. These data show that PrP$^C$ binds first to PPMF and the protein PPMF/PrP$^C$ complex then binds to PrP$^{Sc}$.

The introduction of the HuA sequences into MH3 relieved the inhibition of MHM2 PrP conversion into PrP$^{Sc}$. This shows that the PPMF binding site does not include SHa residues 203 and 205. Instead, these residues are part of the central domain where PrP$^C$ and PrP$^{Sc}$ interact because lack of conversion of MH3 into PrP$^{Sc}$ by MoPrP$^{Sc}$ in ScN2a cells could be partially overcome by changing the two SHaPrP and MH3 PrP are not converted into PrP$^{Sc}$, they are not released from PPMF which in turn prevents MHM2 PrP from binding and being converted.

The methods and materials are the same as those described for Example 5 above.

We claim:

1. An isolated nucleic acid encoding a PrP protein characterized by having a native wild type codon replaced with a non-native codon at a position which encodes an amino acid making up a portion of a discontinuous binding epitope to prion protein modulator factor (PPMF), wherein the replaced codon encodes an amino acid selected from the group consisting of amino acids 160–180 and amino acids 210–225 and the nucleic acid encodes a protein that hinders PrP$^{Sc}$ formation.

2. The isolated nucleic acid of claim 1, wherein the nucleic acid encodes a PrP protein that hinders PrP$^{Sc}$ formation by binding PPMF more tightly than native PrP binds PPMF to the extent that PrP$^{Sc}$ formation is blocked.

3. The isolated nucleic acid of claim 1, wherein the nucleic acid encodes a PrP protein that hinders PrP$^{Sc}$ formation by not binding PPMF sufficiently to allow for the formation of PrP$^{Sc}$.

4. The isolated nucleic acid of claim 1, wherein the nucleic acid encodes a cow PrP protein and the wild type codon replaced is from a position selected from the group consisting of 171, 175, 218 and 222.

5. The isolated nucleic acid of claim 1, wherein the nucleic acid encodes a sheep PrP protein and the wild type codon replaced is from a position selected from the group consisting of 171, 175, 218 and 222.

6. The isolated nucleic acid of claim 1, wherein the nucleic acid encodes a mouse PrP protein and the wild-type codon replaced is from a position selected from the group consisting of 167, 171, 214 and 218.

7. The isolated nucleic gene of claim 1, wherein the nucleic acid encodes a human PrP protein and the wild-type codon replaced is from a position selected from the group consisting of 167, 171, 214 and 218.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
      (A) LENGTH: 66 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:1:

ATCAAGCAGC ACACGGTCAC CACCACCAAG GGGGAGAACT TCACCGAGAC CGATATCAAG      60

ATAATG      66

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:2:

CACTATAGAA CTCGAGCAGC CTCCCT      26

(2) INFORMATION FOR SEQ ID NO:3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

ATAGGCCTGG GACTCCTTCT GGTACTGGGT GATGCA                                 36

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

ATAGGCCTGG GACTCCCTCT CGTACT                                              26

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

ATAGGCCTGG GACTCCTTCT CGTACT                                              26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

ATAGGCCTGG GACTCCCTCT GGTACT                                              26

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

ATAGGCCTGG GACTCCCTCT GGTACTGGGT GATGCA                                 36

(2) INFORMATION FOR SEQ ID NO:8:

(i) SEQUENCE CHARACTERISTICS:

```
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

ATAGGCCTGG GACTCCTTTT TGTACT                                              26

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

ATAGGCCTGG GACTCCTTGA TGTACT                                              26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

ATAGGCCTGG GACTCCTTCC GGTACT                                              26

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

ATAGGCCTGG GACTCCCAGT ACT                                                 23

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

ATAGGCCTGG GACTCCTTCG GGTACT                                              26

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear
```

(ii) MOLECULE TYPE: Other (xi) SEQUENCE DESCRIPTION: SEQ ID NO:13:

ATAGGCCTGG GACTCCTTCT GGTACCGGGT GACGCA                                36

(2) INFORMATION FOR SEQ ID NO:14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:14:

ATAGGCCTGG GACTCCTTCT CGTACCGGGT GACGCA                                36

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:15:

ATAGGCCTGG GACTCCTTCT GGTACTGCTT GCA                                   33

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:16:

ATAGGCCTGG GACTCCTTCT GGTACTGGGT CTCGCA                                36

(2) INFORMATION FOR SEQ ID NO:17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:17:

ATAGGCCTGG GACTCCTTCT GGTACTGGGT GGCGCA                                36

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:18:

ATAGGCCTGG GACTCCTTCT GGTACTGGGT CCAGCA                                36

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:19:

ATAGGCCTGG GACTCCTTCT GGTACTGGGT GGGGCA                             36

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:20:

ATCAAGCAGC ACACGGTCAC CACCA                                         25

(2) INFORMATION FOR SEQ ID NO:21:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: MOUSE PRION PROTEIN, MoPrP (xi) SEQUENCE DESCRIPTION: SEQ ID NO:21:

```
Met Ala Asn Leu Gly Tyr Trp Leu Leu Ala Leu Phe Val Thr Met Trp
 1               5                  10                  15

Thr Asp Val Gly Leu Cys Lys Lys Arg Pro Lys Pro Gly Gly Trp Asn
             20                  25                  30

Thr Gly Gly Ser Arg Tyr Pro Gly Gln Gly Ser Pro Gly Gly Asn Arg
         35                  40                  45

Tyr Pro Pro Gln Gly Gly Thr Trp Gly Gln Pro His Gly Gly Gly Trp
     50                  55                  60

Gly Gln Pro His Gly Gly Ser Trp Gly Gln Pro His Gly Gly Ser Trp
 65                  70                  75                  80

Gly Gln Pro His Gly Gly Gly Trp Gly Gln Gly Gly Thr His Asn
                 85                  90                  95

Gln Trp Asn Lys Pro Ser Lys Pro Lys Thr Asn Leu Lys His Val Ala
                100                 105                 110

Gly Ala Ala Ala Ala Gly Ala Val Val Gly Gly Leu Gly Gly Tyr Met
            115                 120                 125

Leu Gly Ser Ala Met Ser Arg Pro Met Ile His Phe Gly Asn Asp Trp
        130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175
```

Asp Cys Val Asn Ile Thr Ile Lys Gln His Thr Val Thr Thr Thr Thr
                180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu Ser Gln Ala Tyr
210                 215                 220

Tyr Asp Gly Arg Arg Ser Ser Thr Val Leu Phe Ser Ser Pro Pro
225                 230                 235                 240

Val Ile Leu Leu Ile Ser Phe Leu Ile Phe Leu Ile Val Gly
                245                 250

(2) INFORMATION FOR SEQ ID NO:22:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN PRION PROTEIN, HuPrP (xi) SEQUENCE DESCRIPTION: SEQ ID NO:22:

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

(2) INFORMATION FOR SEQ ID NO:23:

(i) SEQUENCE CHARACTERISTICS:
        (A) LENGTH: 263 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: BOVINE PRION PROTEIN, BoPrP (xi) SEQUENCE DESCRIPTION: SEQ ID NO:23:

```
Met Val Lys Ser His Ile Gly Ser Trp Ile Leu Val Leu Phe Val Ala
1               5                  10                  15

Met Trp Ser Asp Val Gly Leu Cys Lys Lys Arg Pro Lys Pro Gly Gly
            20                  25                  30

Trp Asn Thr Gly Gly Ser Arg Tyr Pro Gly Gln Gly Ser Pro Gly Gly
            35                  40              45

Asn Arg Tyr Pro Pro Gln Gly Gly Gly Trp Gly Gln Pro His Gly
    50                  55                  60

Gly Gly Trp Gly Gln Pro His Gly Gly Gly Trp Gly Gln Pro His Gly
65                  70                  75                  80

Gly Gly Trp Gly Gln Pro His Gly Gly Gly Trp Gly Gln Pro His Gly
                85                  90                  95

Gly Gly Gly Trp Gly Gln Gly Gly Thr His Gly Gln Trp Asn Lys Pro
                100                 105                 110

Ser Lys Pro Lys Thr Asn Met Lys His Val Ala Gly Ala Ala Ala Ala
        115                 120                 125

Gly Ala Val Val Gly Gly Leu Gly Gly Tyr Met Leu Gly Ser Ala Met
    130                 135                 140

Ser Arg Pro Leu Ile His Phe Gly Ser Asp Tyr Glu Asp Arg Tyr Tyr
145                 150                 155                 160

Arg Glu Asn Met His Arg Tyr Pro Asn Gln Val Tyr Tyr Arg Pro Val
                165                 170                 175

Asp Gln Tyr Ser Asn Gln Asn Asn Phe Val His Asp Cys Val Asn Ile
            180                 185                 190

Thr Val Lys Glu His Thr Val Thr Thr Thr Lys Gly Glu Asn Phe
        195                 200                 205

Thr Glu Thr Asp Ile Lys Met Met Glu Arg Val Val Glu Gln Met Cys
210                 215                 220

Val Thr Gln Tyr Gln Lys Glu Ser Gln Ala Tyr Tyr Asp Gly Ala
225                 230                 235                 240

Ser Val Ile Leu Phe Ser Ser Pro Pro Val Ile Leu Leu Ile Ser Phe
                245                 250                 255

Leu Ile Phe Leu Ile Val Gly
            260
```

(2) INFORMATION FOR SEQ ID NO:24:

(i) SEQUENCE CHARACTERISTICS:
        (A) LENGTH: 255 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: SHEEP PRION PROTEIN, ShPrP (xi) SEQUENCE DESCRIPTION: SEQ ID NO:24:

```
Met Val Lys Ser His Ile Gly Ser Trp Ile Leu Val Leu Phe Val Ala
 1               5                  10                  15
Met Trp Ser Asp Val Gly Leu Cys Lys Lys Arg Pro Lys Pro Gly Gly
                20                  25                  30
Trp Asn Thr Gly Gly Ser Arg Tyr Pro Gly Gln Gly Ser Pro Gly Gly
                35                  40                  45
Asn Arg Tyr Pro Pro Gln Gly Gly Gly Trp Gly Gln Pro His Gly
 50                  55                  60
Gly Gly Trp Gly Gln Pro His Gly Gly Gly Trp Gly Gln Pro His Gly
 65                  70                  75                  80
Gly Ser Trp Gly Gln Pro His Gly Gly Gly Trp Gly Gln Gly Gly
                85                  90                  95
Ser His Ser Gln Trp Asn Lys Pro Ser Lys Pro Lys Thr Asn Met Lys
                100                 105                 110
His Val Ala Gly Ala Ala Ala Gly Ala Val Val Gly Gly Leu Gly
                115                 120                 125
Gly Tyr Met Leu Gly Ser Ala Met Ser Arg Pro Leu Ile His Phe Gly
 130                 135                 140
Asn Asp Tyr Glu Asp Arg Tyr Tyr Arg Glu Asn Met Tyr Arg Tyr Pro
 145                 150                 155                 160
Asn Gln Val Tyr Tyr Arg Pro Val Asp Gln Tyr Ser Asn Gln Asn Asn
                165                 170                 175
Phe Val His Asp Cys Val Asn Ile Thr Val Lys Gln His Thr Val Thr
                180                 185                 190
Thr Thr Thr Lys Gly Glu Asn Phe Thr Glu Thr Asp Ile Lys Ile Met
                195                 200                 205
Glu Arg Val Val Glu Gln Met Cys Ile Thr Gln Tyr Gln Arg Glu Ser
                210                 215                 220
Gln Ala Tyr Tyr Gln Arg Gly Ala Ser Val Ile Leu Phe Ser Ser Pro
 225                 230                 235                 240
Pro Val Ile Leu Leu Ile Ser Phe Leu Ile Phe Leu Ile Val Gly
                245                 250                 255
```